United States Patent [19]
Bläckberg et al.

[11] Patent Number: 5,827,683
[45] Date of Patent: Oct. 27, 1998

[54] NUCLEIC ACIDS ENCODING BSSL VARIANTS

[75] Inventors: Lars Gustav Bläckberg; Michael Edlund; Stig Lennart Hansson; Olle Carl Edward Hernell, all of Umeå; Lennart Gustav Lundberg, Billdal; Mats Olof Strömqvist, Umeå; Jan Birger Fredrik Törnell, Västra Frölunda, all of Sweden

[73] Assignee: Astra Aktiebolag, Sodertalje, Sweden

[21] Appl. No.: 204,691

[22] Filed: Mar. 1, 1994

[30] Foreign Application Priority Data

Mar. 1, 1993 [SE] Sweden .................................. 9300686
Mar. 4, 1993 [SE] Sweden .................................. 9300722

[51] Int. Cl.$^6$ .............................. C07H 21/04; C12N 5/00; C12N 15/12; C12P 21/00
[52] U.S. Cl. ...................... 435/69.1; 435/69.7; 435/70.1; 435/70.3; 435/71.1; 435/172.3; 435/200; 435/243; 435/320.1; 435/325; 536/23.1; 536/23.2; 536/23.5; 935/66
[58] Field of Search ........................... 530/350; 536/24.1, 536/24.21, 23.5, 23.2, 23.1; 435/69.1, 69.7, 172.1, 172.3, 183, 240.21, 252.3, 320.1, 70.1, 70.3, 71.1, 200, 243, 325; 424/192.1, 94.6; 935/66

[56] References Cited

U.S. PATENT DOCUMENTS 5,200,183  4/1993  Tang et al. .............................. 424/94.6

FOREIGN PATENT DOCUMENTS

WO91 15234  10/1991  WIPO .
WO91 18923  12/1991  WIPO .

OTHER PUBLICATIONS

Bläckberg, *Eur. J. Biochem.*, 192, pp. 543–550, (1990).

Baba et al. "Structure of Human . . ." Biochemistry 30 (1991) 500–510.

DiPersio et al. "Identification of the Active Site" J. Bio. Chemistry 265 (1990) 16801–16806.

DiPersio et al., "Site–specific mutagenesis of an essential histidine residue . . . " J. Biol. Chemistry 266 (1991) 4033–6.

DiPersio et al. "Apartic acid 320 is required . . . " J. Bio. Chemistry R68 (1993) 300–304.

Rieger et al., EDS. in "Glossary of Genetics and Cytogenetics" Springer–Verlag, Berlin, 1976, p. 282.

*Primary Examiner*—Brian R. Stanton
*Attorney, Agent, or Firm*—White & Case L.L.P.

[57] ABSTRACT

The invention discloses nucleic acids encoding variant Bile Salt Stimulated Lipase (BSSL; EC 3.1.1.1). The encoded variant BSSL enzymes maintain catalytic activity but contain fewer glycosylation sites that full-length BSSL. This reduced glycosylation facilitates purification and characterization of recombinant BSSL proteins.

15 Claims, 18 Drawing Sheets

| PRIMER | SEQUENCE (5'-3') |
|---|---|
| 5'-PRIMER | CTGTGTGGCAAGAAGGAAGTGTTGT |
| 3'-PRIMER | CAACTCCTGACCTCAAGTGATC |

NUCLEIC ACIDS ENCODING BSSL VARIANTS

TECHNICAL FIELD

The present invention relates to novel polypeptides which are variants of Bile Salt-Stimulated Lipase (BSSL; EC 3.1.1.1). It also relates to DNA molecules encoding the said polypeptides, and to subproducts comprising the said DNA molecules. The invention further relates to processes for producing the said BSSL variants and for producing transgenic non-human mammals capable of expressing the BSSL variants. Furthermore the invention relates to such transgenic animals as well as to infant formulas comprising milk from such transgenic animals. The invention also relates to pharmaceutical compositions comprising the said polypeptides; and the use of the said polypeptides and DNA molecules for the manufacture of medicaments.

BACKGROUND ART

Hydrolysis of dietary lipids

Dietary lipids are an important source of energy. The energy-rich triacylglycerols constitute more than 95% of these lipids. Some of the lipids, e.g. certain fatty acids and the fat-soluble vitamins, are essential dietary constituents. Before gastro-intestinal absorption the triacylglycerols as well as the minor components, i.e. esterified fat-soluble vitamins and cholesterol, and diacylphosphatidylglycerols, require hydrolysis of the ester bonds to give rise to less hydrophobic, absorbable products. These reactions are catalyzed by a specific group of enzymes called lipases.

In the human, the essential lipases involved are considered to be Gastric Lipase, Pancreatic Colipase-Dependent Lipase (hydrolysis of tri- and diacylglycerols), Pancreatic Phospholipase A2 (hydrolysis of diacylphosphatidylglycerols) and Carboxylic Ester Hydrolase (CEH) (hydrolysis of cholesteryl- and fat soluble vitamin esters, but also tri-, di-, and monoacylglycerols). In the breast-fed newborn, Bile Salt-Stimulated Lipase (BSSL) plays an essential part in the hydrolysis of several of the above mentioned lipids. Together with bile salts the products of lipid digestion form mixed micelles or unilamellar vesicles (Hernell et al., 1990) from which absorption occurs.

Bile Salt-Stimulated Lipase

Bile Salt-Stimulated Lipase (BSSL) is a constituent of milk in a limited number of species, e.g. humans, gorillas, cats and dogs (Hernell et al., 1989, Hamosh et al., 1986). When mixed with bile in upper small intestinal contents, BSSL is specifically activated by primary bile salts (Hernell, 1975). BSSL, which accounts for approximately 1% of total milk protein (Bläckberg & Hernell, 1981), is not degraded during passage with the milk through the stomach, and in duodenal contents it is protected by bile salts from inactivation by pancreatic proteases such as trypsin and chymotrypsin.

Heat treatment of human milk (pasteurization at 62.5° C., 30 min), which inactivates BSSL completely (Björksten et al., 1980), reduces the coefficient of fat absorption by approximately ⅓ in preterm infants (Williamson et al., 1978, Atkinson et al., 1981). Hence, the superior utilization of fresh human milk triacylglycerol compared to that of infant formulas of similar fat composition is due to BSSL (Hernell et al., 1991, Chapell et al., 1986).

BSSL is a non-specific lipase (EC 3.1.1.1) in as much as it hydrolyses not only triacylglycerol but also di- and monoacylglycerol, cholesteryl esters and fat-soluble vitamin esters (Bläckberg & Hernell, 1983). Thus, after activation, BSSL has the potential to hydrolyze most human milk lipids by itself, albeit the most efficient utilization of human milk triacylglycerol requires the synergistic action of gastric lipase (EC 3.1.1.3), colipase-dependent pancreatic lipase (EC 3.1.1.3), and BSSL (Bernbäck et al., 1990).

Recent studies suggest that the milk enzyme is of particular importance for the utilization of long-chain polyunsaturated fatty acids by the newborn infant (Hernell et al. 1993). These fatty acids are important precursors of eicosanoids and for the neuro-development. Newborn infants, particularly if born before term, have a limited capacity for synthesis of these fatty acids from their precursors. Hence, they are considered essential for an as yet not defined period of time after birth.

In recent studies from several laboratories the cDNA structures from both the milk lipase and the pancreas Carboxylic Ester Hydrolase (CEH) (E.C. 3.1.1.1) have been characterized (Baba et al., 1991; Hui et al., 1991; Nilsson et al., 1990; Reue et al., 1991) and the conclusion is that the milk enzyme and the pancreas enzyme are products of the same gene. The cDNA sequence and deduced amino acid sequence of the BSSL/CEH gene (SEQ ID NO: 1) are disclosed also in WO 91/15234 (Oklahoma Medical Research Foundation) and in WO 91/18923 (Aktiebolaget Astra).

BSSL is a single-chain glycoprotein. The deduced protein (SEQ ID NO: 3) contains 722 amino acid residues and is highly glycosylated (Abouakil et al., 1989). The N-terminal half of the protein shows a striking homology to acetyl cholinesterase and some other esterases (Nilsson et al., 1990).

A tentative active site serine residue is located at serine-194; the sequence around this serine accords with the consensus active-site sequence of serine hydrolases. The single tentative N-glycosylation site is positioned only seven residues N-terminal of the active site serine (Nilsson et al., 1990).

The BSSL sequence contains in its C-terminal part 16 proline-rich repeats of 11 amino acid residues each. A variation in number of repeats seems to be a major explanation for differences in molecular size and amino acid composition between corresponding enzymes from different species (Han et al., 1987, Fontaine et al., 1991, Kyger et al., 1989). These repeats carry most of the 15–20% carbohydrate of the protein (Baba et al., 1991, Abouakil et al., 1989).

The unique structural difference between BSSL and typical esterases resides in the C-terminal part of the polypeptide chain, i.e. the 16 proline-rich repeats of 11 amino acid residues. The corresponding pancreatic enzymes from cow and rat have only 3 and 4 repeats, respectively (Han et al., 1987, Kyger et al., 1989). A likely hypothesis has therefore been that the C-terminal part, or at least part of it, is indispensable for lipase activity, i.e. activity against emulsified long-chain triacylglycerol.

Lipid malabsorption

Common causes of lipid malabsorption, and hence malnutrition, are reduced intraluminal levels of Pancreatic Colipase-Dependent Lipase and/or bile salts. Typical examples of such lipase deficiency are patients suffering from cystic fibrosis, a common genetic disorder resulting in a life-long deficiency in 80% of the patients, and chronic pancreatitis, often due to chronic alcoholism.

The present treatment of patients suffering from a deficiency of pancreatic lipase is the oral administration of very large doses of a crude preparation of porcine pancreatic enzymes. However, Colipase-Dependent Pancreatic Lipase is inactivated by the low pH prevalent in the stomach. This effect cannot be completely overcome by the use of large doses of enzyme. Thus the large doses administered are inadequate for most patients, and moreover the preparations are impure and unpalatable.

Certain tablets have been formulated which pass through the acid regions of the stomach and discharge the enzyme only in the relatively alkaline environment of the jejunum. However, many patients suffering from pancreatic disorders have an abnormally acid jejunum and in those cases the tablets may fail to discharge the enzyme.

Moreover, since the preparations presently on the market are of a non-human source there is a risk of immunoreactions that may cause harmful effects to the patients or result in reduced therapy efficiency. A further drawback with the present preparations is that their content of other lipolytic activities than Colipase-Dependent Lipase are not stated. In fact, most of them contain very low levels of BSSL/CEH activity. This may be one reason why many patients, suffering from cystic fibrosis in spite of supplementation therapy, suffer from deficiencies of fat soluble vitamins and essential fatty acids.

Thus, there is a great need for products with properties and structure derived from human lipases and with a broad substrate specificity, which products may be orally administered to patients suffering from deficiency of one or several of the pancreatic lipolytic enzymes. Products that can be derived from the use of the present invention fulfil this need by themselves, or in combination with preparations containing other lipases.

SHORT DESCRIPTION OF THE INVENTIVE CONCEPT

Recombinant BSSL variants according to the invention, have maintained catalytic activity, but contain less glycosylation sites than full-length BSSL, and are thus produced with a potentially reduced degree of carbohydrate heterogeneity. This reduced complexity facilitates purification and characterization of the recombinant protein, which will result in a more cost-effective production of polypeptides having BSSL activity.

In another aspect, the reduced degree of glycosylation is less demanding for the host and allows higher production in several host cells. In yet another aspect, the reduced number of glycosylation sites in a BSSL variant allows efficient production in lower eukaryotes and restricts the potential risk of abberrant glycosylation, which may raise immunological reactions. The reduced size and less complex glycosylation also implies that the host range is broader than for a protein having very complex and heavy carbohydrate moieties.

Therapeutic use of a BSSL variant which is smaller in size but is equally active, means that the weight of the substance needed for supplementation is reduced. A further possible advantage with a recombinant BSSL variant lacking most or all of the O-glycosylated repeats is a reduced risk for an immunological response in the recipient individual. This is due to the fact that the O-linked sugar may be very heterogenous depending on the cell in which it is produced.

There are indications in the scientific literature that native BSSL binds to, and is taken up by, the intestinal mucosa. A BSSL variant which is selected for having a reduced uptake, will be active on the dietary lipid substrates for a longer period of time, leading to a more efficient intraluminal digestion. Examples of such variants are molecules with reduced glycosylation.

As mentioned above, BSSL has been suggested to be of particular importance for the utilization of long-chain polyunsaturated fatty acids (Hernell et al., 1993), which are of great importance for neuro-development of the newborn infant, and of vitamin A. A BSSL variant according to the invention, which is more effective in these respects, can be selected by known methods. A truncated, or shortened, enzyme is likely to be different with regard to conformation which may affect the specificity against different lipid substrates.

DISCLOSURE OF THE INVENTION

In one aspect, the invention relates to a nucleic acid molecule encoding a polypeptide which is a BSSL variant shorter than 722 amino acids, said BSSL variant comprising part of the amino acid sequence shown as residues 536–722 in SEQ ID NO: 3.

The term "part of the amino acid sequence" is to be understood as comprising one single amino acid as well as a sequence of several amino acids or several such sequences combined.

The term "BSSL variant" is to be understood as a polypeptide having BSSL activity and comprising a part of the amino acid sequence of human BSSL shown as SEQ ID NO: 3 in the Sequence Listing.

The term "polypeptide having BSSL activity" is to be understood as a polypeptide comprising at least the properties (a) suitable for oral administration;
(b) activated by specific bile salts;
(c) acting as a nonspecific lipase in the contents of the small intestines, i.e. being able to hydrolyze lipids relatively independent of their chemical structure and physical state (emulsified, micellar, soluble);

and optionally one or more of the properties (d) ability to hydrolyze triacylglycerols with fatty aids of different chain-length and different degree of unsaturation;
(e) ability to hydrolyze also diacylglycerol, monoacylglycerol, cholesteryl esters, lysophospatidylacylglycerol, and retinyl and other fat soluble vitamin-esters;
(f) ability to hydrolyze not only the sn-1(3) ester bonds in a triacylglycerol but also the sn-2 ester bond;
(g) ability to interact with not only primary but also secondary bile salts;
(h) dependent on bile salts for optimal activity;
(i) stable in the sence that gastric contents will not affect the catalytical efficiency to any substantial degree;
(j) stable against inactivation by pancreatic proteases, e.g. trypsin, provided bile salts are present;
(k) ability to bind to heparin and heparin derivatives, e.g. heparan sulphate;
(l) ability to bind to lipid-water interphases;
(m) stable enough to permit lyophilization;
(n) stable when mixed with food constituents such as in human milk, or milk formula.

In further aspects, the invention relates to a nucleic acid molecule according to above, wherein the said BSSL variant has a phenylalanine residue in its C-terminal position, or comprises the sequence Gln-Met-Pro in its C-terminal part, alternatively comprises the amino acid sequence shown as residues 712–722 in SEQ ID NO: 3 in its C-terminal part.

In the present context, the term "C-terminal position" designates the position of the final C-terminal residue, while the term "C-terminal part" is to be understood as the approximately 50 amino acid residues which constitute the C-terminal end of the BSSL variant.

The invention further relates to a nucleic acid molecule according to above, wherein the said BSSL variant comprises less than 16 repeat units. In the present context the term "repeat unit" designates one of the repeated units of 33 nucleotides each which are indicated in SEQ ID NO: 1 in the Sequence Listing.

In further aspects, the invention relates to a nucleic acid molecule according to above which encodes a polypeptide, the amino acid sequence of which is at least 90% homologous with the amino acid sequence shown as SEQ ID NO: 5, 6 or 9 in the Sequence Listing, as well as a nucleic acid molecule which encodes a polypeptide, the amino acid sequence of which is at least 90% homologous with the amino acid sequence shown as SEQ ID NO: 7 in the Sequence Listing, with the exception for those nucleic acid molecules which encode polypeptides which have an asparagine residue at position 187.

The invention also relates to a polypeptide shown as SEQ ID NO: 5, 6, 7 or 9 in the Sequence Listing, as well as a polypeptide encoded by a nucleic acid sequence according to above.

The invention further relates to a hybrid gene comprising a nucleic acid molecule according to above, a replicable expression vector comprising such a hybrid gene, and a cell harbouring such a hybrid gene. This cell may be a prokaryotic cell, a unicellular eukaryotic organism or a cell derived from a multicellular organism, e.g. a mammal.

In the present context the term "hybrid gene" denotes a nucleic acid sequence comprising on the one hand a nucleic acid sequence encoding a BSSL variant as defined above and on the other hand a nucleic acid sequence of the gene which is capable of mediating the expression of the hybrid gene product. The term "gene" denotes an entire gene as well as a subsequence thereof capable of mediating and targeting the expression of the hybrid gene to the tissue of interest. Normally, said subsequence is one which at least harbours one or more of a promoter region, a transcriptional start site, 3' and 5' non-coding regions and structural sequences.

The hybrid gene is preferably formed by inserting in vitro the nucleic acid sequence encoding the BSSL variant into the gene capable of mediating expression by use of techniques known in the art. Alternatively, the nucleic acid sequence encoding the BSSL variant can be inserted in vivo by homologous recombination.

In the present context, the term "replicable" means that the vector is able to replicate in a given type of host cell into which it has been introduced. Immediately upstream of the nucleic acid sequence there may be provided a sequence coding for a signal peptide, the presence of which ensures secretion of the BSSL variant expressed by host cells harbouring the vector. The signal sequence may be the one naturally associated with the nucleic acid sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. Examples of suitable vectors are a bacterial expression vector and a yeast expression vector. The vector of the invention may carry any of the nucleic acid sequences of the invention as defined above.

In another aspect, the invention relates to a process for the production of a recombinant polypeptide, said process comprising (i) inserting a nucleic acid molecule according to above in a hybrid gene which is able to replicate in a specific host cell or organism; (ii) introducing the resulting recombinant hybrid gene into a host cell or organism; (iii) growing the resulting cell in or on a culture medium, or identifying and reproducing an organism, for expression of the polypeptide; and (iv) recovering the polypeptide.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant human BSSL variant expressed by the cells may be secreted, i.e. exported through the cell membrane, dependent on the type of cell and the composition of the vector.

If the BSSL variant is produced intracellularly by the recombinant host, that is, is not secreted by the cell, it may be recovered by standard procedures comprising cell disrupture by mechanical means, e.g. sonication or homogenization, or by enzymatic or chemical means followed by purification.

In order to be secreted, the DNA sequence encoding the BSSL variant should be preceded by a sequence coding for a signal peptide, the presence of which ensures secretion of the BSSL variant from the cells so that at least a significant proportion of the BSSL variant expressed is secreted into the culture medium and recovered. The invention also relates to an expression system, comprising a hybrid gene which is expressible in a host cell or organism harbouring said hybrid gene, so that a recombinant polypeptide is produced when the hybrid gene is expressed, said hybrid gene being produced by inserting a nucleic acid sequence according above into a gene capable of mediating expression of the said hybrid gene.

A possible process for producing a recombinant BSSL variant of the invention is by use of transgenic non-human mammals capable of excreting the BSSL variant into their milk. The use of transgenic non-human mammals has the advantage that large yields of the recombinant BSSL variant are obtainable at reasonable costs and, especially when the non-human mammal is a cow, that the recombinant BSSL variant is produced in milk which is the normal constituent of, e.g., infant formulae so that no extensive purification is needed when the recombinant BSSL variant is to be used as a nutrient supplement in milk-based products.

Furthermore, production in a higher organism such as a non-human mammal normally leads to the correct processing of the mammalian protein, e.g. with respect to post-translational processing as discussed above and proper folding. Also large quantities of a substantially pure BSSL variant may be obtained.

Accordingly, the expression system referred to above may be a mammalian expression system comprising a DNA sequence encoding a BSSL variant inserted into a gene encoding a milk protein of a non-human mammal, so as to form a hybrid gene which is expressible in the mammary gland of an adult female of a mammal harbouring said hybrid gene.

The mammary gland as a tissue of expression and genes encoding milk proteins are generally considered to be particularly suitable for use in the production of heterologous proteins in transgenic non-human mammals, as milk proteins are naturally produced at high expression levels in the mammary gland. Also, milk is readily collected and available in large quantities. In the present connection, the use of milk protein genes in the production of a recombinant BSSL variant has the further advantage that it is produced under conditions similar to the its natural production conditions in terms of regulation of expression and production location (the mammary gland).

When used in a transgenic mammal, the hybrid gene referred to above preferably comprises a sequence encoding a signal peptide so as to enable the hybrid gene product to be secreted correctly into the mammary gland. The signal peptide will typically be the one normally found in the milk protein gene in question or one associated with the DNA sequence encoding the BSSL variant. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding the BSSL variant. In the hybrid gene, the DNA sequence encoding the BSSL variant will normally comprise its stop codon, but not its own message cleavance and polyadenylation site. Downstream of the DNA sequence encoding the BSSL variant, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding the BSSL variant in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

The milk protein gene to be used may be derived from the same species as the one in which the expression system is to be inserted, or it may be derived from another species. In this connection it has been shown that the regulatory elements that target gene expression to the mammary gland are functional across species boundaries, which may be due to a possible common ancestor (Hennighausen et al., 1990).

Examples of suitable genes encoding a milk protein or effective subsequences thereof to be used in the construction of an expression system of the invention, are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of a BSSL variant, e.g. bovine αS1-casein and rabbit β-casein. The presently preferred gene is a murine WAP gene as this has been found to be capable of providing a high level of expression of a number of foreign human proteins in milk of different transgenic animals (Hennighausen et al, 1990).

Another sequence preferably associated with the expression system of the invention is a so-called expression stabilizing sequence capable of mediating high-level expression. Strong indications exist that such stabilizing sequences are found in the vicinity of and upstreams of milk protein genes.

Included in the invention is also a process of producing a transgenic non-human mammal capable of expressing a BSSL variant, comprising (a) introducing an expression system according to above into a fertilized egg or a cell of an embryo of a non-human mammal so as to incorporate the expression system into the germline of the mammal and (b) developing the resulting introduced fertilized egg or embryo into an adult female non-human mammal.

The incorporation of the expression system into the germline of the mammal may be performed using any suitable technique, e.g. as described in "Manipulating the Mouse Embryo"; A Laboratory Manual, Cold Spring Harbor Laboratory Press, 1986. For instance, a few hundred molecules of the expression system may be directly injected into a fertilized egg, e.g. a fertilized one cell egg or a pro-nucleus thereof, or an embryo of the mammal of choice, and the microinjected eggs may then be transferred into the oviducts of pseudopregnant foster mothers and allowed to develop.

The process of producing a transgenic non-human mammal capable of expressing a BSSL variant, can also comprise a process wherein the said mammal is substantially incapable of expressing BSSL from the mammal itself. Such a process comprises (a) destroying the BSSL expressing capability of the mammal so that substantially no mammalian BSSL is expressed and inserting an expression system according to above into the germline of the mammal in such a manner that a BSSL variant is expressed in the mammal; and/or (b) replacing the mammalian BSSL gene or part thereof with an expression system as defined above.

The mammalian BSSL expressing capability can conveniently be destroyed by introduction of mutations in the DNA sequence responsible for the expression of BSSL. Such mutations may comprise mutations which make the DNA sequence out of frame, introduction of a stop codon, or a deletion of one or more nucleotides of the DNA sequence.

The mammalian BSSL gene or a part thereof may be replaced with an expression system as defined above or with a DNA sequence encoding the BSSL variant by use of the well known principles of homologous recombination.

In a further important aspect, the invention relates to a transgenic non-human mammal harbouring in its genome a DNA sequence according to above. The said DNA sequence can preferably be present in the germline of the mammal, and in a milk protein gene of the mammal. The transgenic non-human mammal can preferably be selected from the group consisting of mice, rats, rabbits, sheep, pigs and cattle.

Included in the invention are also progeny of a transgenic non-human mammal according to above as well as milk obtained from such a transgenic non-human mammal.

The invention further relates to an infant formula comprising milk according to above, and an infant formula comprising a BSSL variant as defined above. The infant formula may be prepared using conventional procedures and contain any necessary additives such as minerals, vitamins etc.

In further aspects, the invention relates to a pharmaceutical composition comprising a BSSL variant as defined above, as well as such a BSSL variant for use in therapy.

In yet further aspects, the invention relates to the use of a BSSL variant as defined above for the manufacture of a medicament for the treatment of a pathological condition related to exocrine pancreatic insufficiency; cystic fibrosis; chronic pancreatitis; fat malabsorption; malabsorption of fat soluble vitamins; fat malabsorption due to physiological reasons. The invention also relates to the use of a BSSL variant for the manufacture of a medicament for the improvement of the utilization of dietary lipids, particularly in preterm born infants.

EXAMPLES
1. EXPRESSION OF RECOMBINANT BSSL IN EUKARYOTIC AND PROKARYOTIC CELLS
1.1. EXPERIMENTAL PROCEDURES
1.1.1. Recombinant plasmids The plasmid pS146 containing the 2.3 kb human BSSL cDNA (Nilsson et al., 1990) cloned into pUC19 was digested with HindIII and SalI and the BSSL cDNA was introduced into a bovine papilloma virus (BPV) expression vector, pS147 (FIG. 1). This vector contains the human BSSL cDNA under control of the murine metallothioneine 1 (mMT-1) enhancer and promoter element (Pavlakis & Hamer, 1983). The mRNA processing signals are provided by a genomic fragment containing part of exon II, intron II, exon III and downstream elements of the rabbit β-globin gene. This transcriptional unit was cloned into a vector containing the entire BPV genome. Transcription was unidirectional for BPV and the BSSL transcriptional unit. For propagation of the vector in *E.coli* the vector also contains pML2d, a pBR322 derivative (Sarver et al., 1982).

The expression vector pS147 was co-transfected with a vector encoding the neomycin resistance gene driven by the Harvey Sarcoma virus 5'-Long terminal repeat and Simian virus 40 polyadenylation signals (Lusky & Botchan, 1984).

For expression of BSSL in *E.coli*, the BSSL cDNA was subcloned as a NdeI-BamHI fragment from plasmid pT7-7 (Ausubel et al., 1992) into plasmid pGEMEX-1 (Promega, Madison, Wis., USA) (Studier & Moffat, 1986). By this cloning procedure the T7 gene 10 encoding sequence was replaced by the BSSL gene coding for the mature protein preceded by a start codon. The final expression vector, pGEMEX/BSSL, was verified by DNA sequencing using specific BSSL internal primers.

1.1.2. Mutagenesis

Nucleotide number 1 was assigned to the A in the initiation codon ATG. For amino acid numbering the first methionine in the signal peptide is -23 and the first amino acid residue of the mature protein, an alanine, is assigned number 1.

For the construction of the deletion variant A (SEQ ID NO: 4), two PCR primers were synthesized, PCR-1 and PCR-2 (Table 1). The HindIII, SalI and BamHI sites were created for cloning into different plasmids. The BclI site was generated in the BSSL sequence without altering the amino acid sequence. This was done to facilitate addition of synthetic DNA to obtain the other variants. The primer PCR-2 contains two synthetic stop codons. The resulting PCR fragments were digested with BamHI and HindIII and cloned into pUC18 for sequence analysis. This plasmid was designated pS157. The correct PCR fragment was inserted into the BPV expression vector by fusion to the BSSL sequence at the unique Asp700 site (position 1405 in the BSSL cDNA) and the SalI site in front of the β-globin gene fragment, resulting in pS257.

The B-variant construction (SEQ ID NO: 5) was done using oligonucleotides number 3,4,7 and 8 (Table 1). The annealed oligonucleotides encodes the very C-terminal amino acid sequence, representing lysine 712 to phenylalanine 722 in the full-length protein. This fragment was fused to glutamine 535. A translational stop was inserted directly after the last phenylalanine. This fragment contains a BclI site in the 5'-end and a SalI site in the 3'-end, allowing introduction into pS157. The resulting plasmid was digested with Asp700 and SalI and the 313 bp fragment was introduced into the expression vector as described above. The resulting plasmid was designated pS258.

TABLE 1

Synthetic oligonucleotides used for construction of the BSSL variants. Nucleotides of restriction sites are underlined. Translational stop signals are indicated by bold letters. The altered codon in variant N is indicated in PCR-3 by bold letters and an asterisk.

| Oligo-nucleotide | Sequence (5'-3') |
|---|---|
| PCR-1 (SEQ ID NO: 10) | CGGGATCCGAAGCCCTTCGCCACCCCCACG |
| PCR-2 (SEQ ID NO: 11) | CGAAGCTTGTCGACTTACTACTGATCAGTCACTGTGGGCAGCGCCAG |
| PCR-3 (SEQ ID NO: 12) | GGGAATTCTGGCCATTGCTTGGGTGAAGAGGAATATCGCGGCCTTCGG GGGGGACCCCAACCAGATCACGCTCTTCGGGGAGTCT<br>                      * |
| PCR-4 (SEQ ID NO: 13) | CGGGATCCCACATAGTGCAGCATGGGGTACTCCAGGCC |
| 1 (SEQ ID NO: 14) | GATCAGGGGGCCCCCCCCGTGCCGCCCACGGGTGACTCCGGG |
| 2 (SEQ ID NO: 15) | GCCCCCCCGTGCCGCCCACGGGTGACTCCAAGGAAGCTCAGA |
| 3 (SEQ ID NO: 16) | TGCCTGCAGTCATTAGGTTTTAGTAAGTCGACA |
| 4 (SEQ ID NO: 17) | AGCTTGTCGACTTACTAAAACCTAATGACTG |
| 5 (SEQ ID NO: 18) | CAGGCATCTGAGCTTCCTTGGAGTCACCCGTGGGCGGCACGGGGGGGG CCCCGGA |
| 6 (SEQ ID NO: 19) | GTCACCCGTGGGCGGCACGGGGGGGGCCCCCT |
| 7 (SEQ ID NO: 20) | GATCAGAAGGAAGCTCAGA |
| 8 (SEQ ID NO: 21) | CAGGCATCTGAGCTTCCTTCT |

In order to construct the gene encoding the C-variant (SEQ ID NO: 6), oligonucleotides 1 to 6 (Table 1) were used. The annealed DNA fragment contains two repetitions, encoding eleven amino acids, identical to consensus (Nilsson et al., 1990), inserted between glutamine 535 and the lysine 712 to phenylalanine 722 sequence. This fragment also contains a BclI site in the 5'-end and a SalI site in the 3'-end, allowing the same cloning strategy as above. The resulting plasmid was designated pS259.

For the construction of variant N (non-N-glycosylated variant, SEQ ID NO: 7), two PCR primers (PCR-3 and PCR-4 in Table 1), were synthesized. The EcoRI and BamHI sites were created for cloning of the 360 bp PCR product into pUC19 for sequence analysis. The potential N-linked glycosylation site at asparagine 187, was changed to a glutamine. The modified sequence was isolated as a BalI-HindIII fragment and cloned into SacI and HindIII digested pUC19 together with a SacI and BalI fragment containing the mMT-1 promoter and 5'-end of BSSL cDNA. An approximately 1.2 kb SacI-DraIII fragment was isolated from this plasmid and inserted in the mMT-1 element and BSSL cDNA sequence, respectively, within the expression vector. The resulting plasmid was designated pS299.

1.1.3. Mammalian cell culture and transfections

The vectors were co-transfected into the murine cell line C127 (ATCC CRL 1616) according to the calcium-phosphate precipitation method (Graham & Van der Eb, 1973).

The C127 cells were cultured in Ham's F12-Dulbecco's Modified Eagle's medium (DMEM) (1:1) supplemented with 10% fetal calf serum. Neomycin resistant cell clones were selected with 1.5 mg$\times$ml$^{-1}$ of G418 and after 10–15 days resistant cell clones were isolated from the master plates and passaged for analysis.

1.1.4. Bacterial strains and culture conditions

For expression experiments the vector pGEMEX/BSSL was transformed into E.coli strains JM109(DE3) and BL21 (DE3)pLysS. The expression experiments were carried out as described by Studier et al. (1986). After harvesting of bacteria, the cells were pelleted by centrifugation (5,000$\times$g for 10 min at 4° C.). For preparation of periplasm- and cytoplasm fractions, the pellet was resuspended in 4 ml 20 mM Tris-Cl/20% sucrose, pH 8.0, 200 $\mu$l 0.1 M EDTA and 40 $\mu$l lysozyme (15 mg/ml in water) per gram of pellet. The suspension was incubated on ice for 40 minutes. 160 $\mu$l 0.5 M MgCl$_2$ per gram of pellet was added, whereafter the suspension was centrifuged for 20 min at 12,000$\times$g. The resulting supernatant contains periplasmic proteins and the pellet represents the cytoplasmic fraction. Alternatively, for preparation of soluble proteins, the cells were suspended in 40 mM Tris-Cl, 0.1 mM EDTA, 0.5 mM phenylmethylsulphonylfluoride, pH 8.2, freeze-thawed and sonicated several times to lyse. The cell lysate was centrifuged (30,000$\times$g for 30 min at 25° C.).

1.1.5. Nucleic acid analysis

RNA and DNA were prepared from isolated mammalian cell lines or E.coli cells (Ausubel et al., 1992). The RNA or DNA were fractionated on agarose gels and blotted onto GeneScreen Plus (New England Nuclear) and hybridized according to the supplier's instructions.

1.1.6. Preparation of native enzyme

Bile salt-stimulated lipase was purified from human milk as previously described (Bläckberg & Hernell, 1981). The purified preparation was homogenous as judged by SDS-PAGE and had a specific activity of 100 $\mu$mol fatty acid released $\times$ min$^{-1}$ and mg$^{-1}$ when assayed with long-chain triacylglycerol as substrate.

1.1.7. Enzyme assay The enzyme assay was as described (Bläckberg & Hernell, 1981) using triolein emulsified with gum arabic as substrate. The incubations were carried out with 10 mM sodium cholate as activating bile salt. When the bile salt dependency was tested bile salts (sodium cholate or sodium deoxycholate, Sigma Chem. Co.) were added to the concentrations given in FIG. 3.

1.1.8. Western blotting

In order to obtain significant reactions in the blotting experiments the conditioned media were concentrated by chromatography on Blue Sepharose (Pharmacia LKB Biotechnology). The respective media were mixed with Blue Sepharose (approx 10 ml of medium per ml of gel). The gel was washed with (10 ml per ml of gel) with 0.5 M Tris-Cl buffer, pH 7.4, containing 0.1 M KCl. The enzyme activity was eluted with 1.5 M KCl in the same buffer. By this procedure a 25–30-fold concentration was obtained as well as a 3–5-fold purification. SDS-PAGE was performed on 10% polyacrylamide gels essentially according to Laemmli (1970). After transfer to nitrocellulose membranes and incubation with a polyclonal rabbit antiserum to purified BSSL detection was made using goat anti-rabbit IgG conjugated with alkaline phosphatase and a developing kit from Bio-Rad.

1.1.9. Treatment with N-glycosidase F

To 10 $\mu$l of variant B, containing a BSSL activity of 2.5 $\mu$mol fatty acid released$\times$min$^{-1}$, 1 $\mu$l of 1 M $\beta$-mercaptoethanol and 0.5 $\mu$l of 10% (w/v) SDS was added. After boiling for 5 min, 10 $\mu$l 0.1 M Na-phosphate buffer, pH 8.0, 6 $\mu$l 0.1 M EDTA, 4 $\mu$l 7.5% (w/v) Nonidet P 40 and 5 $\mu$l (1U) N-glycosidase F (Boehringer Mannheim) were added. As a control the same amount of variant B was treated identically except that no glycosidase was added. After an overnight incubation at 37° C., the samples were run on SDS-PAGE and blotted using the polyclonal rabbit BSSL antiserum.

1.2. RESULTS 1.2.1. Construction of the BSSL variants

The modifications of the BSSL variants in relation to the full-length BSSL are summarized in Table 2 and FIG. 1. The strategies used for generation of these variants are described in Section 1.1. For variant A (SEQ ID NO: 4), a stop codon was introduced after glutamine at position 535 thereby removing the last 187 amino acids of the full-length protein. For variant B (SEQ ID NO: 5) the domain encoding the 11 very C-terminal amino acids and the original translational stop was fused to glutamine-535. Hence, this variant lacks all the repeats. For variant C (SEQ ID NO: 6) a fragment containing two repeats having a sequence identical to consensus (Nilsson et al., 1990) were inserted between glutamine-535 and the lysine-712 to phenylalanine-722 sequence.

To analyze the importance of the only tentative N-linked carbohydrate structure, positioned dose to the active site serine-194, a variant was constructed. Variant N (SEQ ID NO: 7) was obtained by altering the potential N-glycosylation site at asparagine-187 to a glutamine.

TABLE 2

The amino acid sequence of the BSSL variants in relation to that of human BSSL.

| Variant | Deleted residues | Changed residues |
| --- | --- | --- |
| A (SEQ ID NO: 4) | 536–722 | |
| B (SEQ ID NO: 5) | 536–711 | |
| C (SEQ ID NO: 6) | 536–568, 591–711 | |
| N (SEQ ID NO: 7) | | Asn 187 → Gln |

1.2.2. Characterization of recombinant DNA in the mammalian cell lines

DNA samples were prepared from the cell lines transfected with the expression vectors encoding the different BSSL variants. The prepared DNA was digested with BamHI, fractionated on agarose gels and transferred to membranes for hybridization. The probe used was $^{32}$P-labelled BSSL cDNA. The hybridization results confirmed the presence of the recombinant genes and also that the vector copy number was approximately equal in the different cell lines (FIG. 2). The positions of the hybridizing fragments reflected the different lengths of the various BSSL sequences and were in agreement with the expected sizes. The positions were also similar to the bacteria derived DNA used in the transfection experiment, indicating that no major rearrangement of vector DNA had occurred in the cell lines (FIG. 2). The upper hybridization signals in the DNA sample representing variant A were probably due to partial digestion.

1.2.3. Expression of mRNA for full-length and mutated BSSL in mammalian cells To analyze the expression of the different recombinant BSSL genes RNA was prepared from the isolated cell lines. Northern blot experiments and hybridization with $^{32}$P-labelled BSSL cDNA showed that recombinant mRNA was detectable in all cell lines harboring a BSSL vector (FIG. 3). No hybridization was found in the control sample derived from a cell line containing an identical vector except for BSSL cDNA (FIG. 3).

The different lengths of the hybridizing mRNAs were in accordance with the modifications of the cDNAs. The steady state levels of recombinant BSSL mRNA variants in the different samples were about the same except for variant A (FIG. 3). The reason for the reduced accumulation of variant A mRNA is not known, but it was observed with two populations of cell lines as well as with isolated clones. The presence of equal amounts of RNA in the different samples was confirmed by hybridization to a murine β-actin probe (FIG. 3, lower panel).

1.2.4. Production of full-length and variants of BSSL in mammalian cells

Media from individual clones of the C127-cells, transfected with full-length BSSL and the different mutated forms, were collected and assayed for BSSL activity (FIG. 4). For the full-length molecule and variants N, B and C the activities in the clones with the highest expression ranged from 0.7 to 2.3 $\mu$mol fatty acid released×min$^{-1}$×ml of medium$^{-1}$. With a specific activity comparable to that of the native milk BSSL this would correspond to expression levels of 7–23 $\mu$g×ml medium$^{-1}$. For variant A all the analyzed clones had activities below 0.05 $\mu$mol fatty acid released× min$^{-1}$ and ml of medium$^{-1}$. Concentration on Blue-Sepharose and lyophilization of the done showing the highest activity revealed that an active enzyme indeed was expressed, albeit at very low levels. The possibility that the low activity obtained with variant A in part could be explained by a considerably lower specific activity could not be ruled out.

Western blots from clones of the different transfection experiments are shown in FIG. 5A. The apparent M$_r$ of the BSSL variants were as expected. It should be noted, however, that for full-length BSSL as well as for variants B and C a double band was obtained. Because all three have the single N-glycosylation site intact whereas variant N, which showed no double band, lacks that site, a likely explanation was that the double band resulted from differences in N-glycosylation. Therefore variant B was subjected to digestion with N-glycosidase F. As shown in FIG. 5B, only trace amounts of the upper band remained while the lower band increased in strength indicating that only part of the expressed variant was N-glycosylated.

One of the characteristics of BSSL is its specific activation by primary bile salts, e.g. cholate (Hernell, 1975). All the different recombinant forms of BSSL showed the same concentration dependency for cholate activation (FIG. 6). A maximal activity was obtained at about 10 mM in the assay system used. When cholate was exchanged for deoxycholate (a secondary bile salt) no such activation occurred. Thus, the recombinant full-length as well as the different variants showed the same specificity regarding bile salt activation.

1.2.5. Expression and biochemical characterization of full-length BSSL in E.coli Two *E.coli* strains JM109(DE3) and BL21(DE3)pLysS (Studier et al., 1986) were transformed with the expression vector pGEMEX/BSSL containing the human BSSL cDNA under control of the T7 promoter. Transformants from both strains were identified, cultured and induced with IPTG for about 90 min (Studier et al., 1986). Analysis of total mRNA by Northern blot using the BSSL cDNA as a $^{32}$P-labeled probe demonstrated that expression was efficiently induced in both strains and that the transcription was tightly regulated (FIG. 7A). The apparent size of the recombinant BSSL mRNA, appoximately 2.4 kb, is in agreement with the expected length. SDS-PAGE separation of protein samples and immunodetection with anti-BSSL antibodies showed that full-length BSSL was efficiently produced in *E.coli* (FIG. 7B). More of the protein was secreted to the periplasm in the BL21(DE3)pLysS strain than in JM109(DE3) (FIG. 7B).

IPTG-induced *E.coli* cultures contained active soluble BSSL corresponding to 0.5–4 $\mu$g of BSSL protein/ml culture. Western blotting showed that between 20 and 60% of the reactive material was in the insoluble pellet. Uninduced bacteria did not contain any significant BSSL activity.

The lipase activity from cultured bacteria showed the same bile salt dependence as native milk BSSL.

2. PURIFICATION AND CHARACTERIZATION OF RECOMBINANT FULL-LENGTH AND MUTATED FORMS OF BILE SALT-STIMUATED LIPASE

2.1. EXPERIMENTAL PROCEDURES

2.1.1. Enzymes and enzyme variants

Recombinant full-length BSSL and BSSL variants B, C and N were constructed and expressed as previously described. Compared to the native enzyme Variant B (SEQ ID NO: 5) lacks all 16 unique, O-glycosylated, proline-rich, C-terminal repeats (aa 536–711) but with the most C-terminal fragment (aa 712–722) fused to glutamine-535. Variant C (SEQ ID NO: 6) contains the same C-terminal fragment and two repeats of 11 residues between glutamine-535 and lysine-712. In variant N (non-N-glycosylated variant, SEQ ID NO: 7) the asparagine-187 responsible for the only N-linked sugar was exchanged for a glutamine residue.

Native BSSL was purified from human milk as described (Bläckberg & Hernell, 1981).

2.1.2. Enzyme assay

Lipase activity was assayed as described (Bläckberg & Hernell, 1981) using triolein emulsified in gum arabic as substrate. Sodium cholate (10 mM) was used as activating bile salt. Different modifications of the assay are given in legends to figures.

2.1.3. Preparation of immunosorbent

Purified milk BSSL (5 mg) was coupled to Sepharose using CNBr as described by the manufacturer. 40 ml of a polyclonal antiserum raised in rabbit against purified milk BSSL was passed over the column. Specific antibodies were eluted with 0.1 M glycine-HCl, pH 2.5. The pH was immediately adjusted to approx 8 with solid Tris. After desalting and lyophilization 6 mg of the affinity purified antibodies was coupled to Sepharose as described above.

2.1.4. Purification procedure

Conditioned culture media containing 5–25 μg of recombinant expressed BSSL or BSSL variant was mixed Blue Sepharose (Pharmacia, Sweden) 10 ml media per ml of settled gel. After end-to-end mixing for 30 min the gel was rinsed with 0.05 M Tris-Cl, pH 7.0, 0.05 M KCl and the lipase activity eluted with 0.05 M Tris-Cl, pH 7.0, 1.5 M KCl. The activity peak was pooled and dialyzed against 5 mM sodium veronal, pH 7.4, 0.05 M NaCl. The dialyzate was applied to a heparin-Sepharose column. The column was eluted with a gradient 0.05 to 1.0 M NaCl in 5 mM sodium veronal buffer, pH 7.4. Fractions containing lipase activity were pooled and applied to an immunosorbent column. After rinsing with 0.05 M Tris-Cl, pH 7.5, 0.15 M NaCl lipase bound was eluted with 0.1 M glycin-HCl, pH 2.5. The pH of the fractions was immediately adjusted to approx 8 with solid Tris.

2.1.5. Electrophoresis

Sodium dodecyl sulphate polyacrylamide gel electrophoresis (SDS-PAGE) was performed essentially according to Laemmli (1970). Proteins were stained with Commassie Brilliant Blue.

2.1.6. N-terminal sequence analysis

Amino acid sequence analysis were performed on an Applied Biosystems Inc. 477A pulsed liquid-phase sequencer and an on-line phenylthiohydantoin 120A analyzer with regular cycle programs and chemicals from the manufacturer. Calculated from a sequenced standard protein (β-lactoglobulin) initial and repetitive yields were 47% and 97%, respectively.

2.2. RESULTS 2.2.1. Purification of recombinant BSSL and BSSL variants.

Chromatography on Blue Sepharose of conditioned media was primarilly used to as a concentrating step. The subsequent chromatography on heparin-Sepharose gave an initial purification mainly by removing most of the albumin present in the culture medium. This step also showed that the recombinant BSSL molecules all retained the heparin binding. After the immunosorbent all BSSL variants appeared more than 90% pure, as judged by SDS-PAGE (FIG. 8). The full-length enzyme as well as variant B and C migrated as a doublet. The apparent $M_r$ of the different variants are shown in Table 3. N-terminal sequence analysis gave a single sequence for all variants for 8 cycles: Ala-Lys-Leu-Gly-Ala-Val-Tyr-Thr-.

2.2.2. Lipase activity

In Table 3 the apparent molecular weight of the different preparations is shown. The specific activities of the preparations ranged from 75 to 120 μmol free fatty acid released per min and mg protein. Consequently no significant difference in activity between full-length BSSL and the BSSL variants could be observed.

The preparations all showed an absolute requirement for primary bile salt (sodium cholate) for activity against emulsified long-chain triacylglycerol (FIG. 9A). Sodium deoxocholate did render any of the variants active (data not shown). However, when combining the different bile salts deoxycholate had two effects (FIG. 9B and C). Firstly, it lowered the concentration of cholate needed for activation, and secondly it inhibited enzyme activity at higher bile salt concentration.

TABLE 3

Apparent $M_r$ of recombinant full-length BSSL and BSSL variants.

| Enzyme | $M_r$ (kDa) Determined by SDS-PAGE |
| --- | --- |
| Full-length | 105, 107 |
| Variant B | 63, 65 |
| Variant C | 60, 62 |
| Variant N | 95 |

2.2.3. Stability of recombinant BSSL and BSSL variants

Recombinant BSSL as well as the BSSL variants showed the same pH-stability as native milk BSSL (FIG. 10). An inactivation occured in all cases at a pH around 2.5–3. Above pH 3 all variants were completely stable provided the protein concentration was high enough. This was acomplished by adding bovine serum albumin or ovalbumin (data not shown). Diluted samples were less stable at all tested pH but the threshold remained the same (data not shown). FIG. 11 shows the heat stability of the recombinant enzymes compared to the native milk enzyme. At a temperature of 37–40° C. the activity starts to decrease. The variants (B, C, N) appears to be somewhat less stable than the full-length recombinant enzyme and the milk enzyme. However, if the protein concentration was raised by adding bovine serum albumin all variants was stable also at 40° C. (FIG. 11).

Native milk BSSL and all the recombinant variants were all sensitive to trypsin. A time dependent inactivation was obtained (FIG. 12). If, however, bile salts, i.e. cholate, was included in the buffer the lipase variants were protected and lipase activity retained (FIG. 12).

Thus, with regard to a number of in vitro characteristics, i.e. bile salt activation, heparin binding, pH- and temperature stability and bile salt protection against inactivation by proteases, no significant differences were observed when comparing the different BSSL variants with native milk BSSL.

3. EXPRESSION IN TRANSGENIC ANIMALS 3.1. CONSTRUCTION OF EXPRESSION VECTORS

To construct an expression vector for production of recombinant human BSSL variant in milk from transgenic animals, the following strategy was employed (FIG. 13).

Three plasmids containing different parts of the human BSSL gene (pS309, pS310 and pS311) were obtained using the methods described in Lidberg et al. (1992). The plasmid pS309 contains a SphI fragment covering the BSSL gene from the 5' untranscribed region to part of the fourth intron. The plasmid pS310 contains a SacI fragment covering a BSSL variant gene sequence from part of the first intron to a part of the sixth intron. The plasmid pS311, finally, contains a BamHI fragment covering the BSSL gene from a major part of the fifth intron and the rest of the intron/exon structure with dfeletions in exon 11. The deleted sequences are 231 bp which results in a sequence encoding a BSSL variant which has exactly 77 amino acids or seven repeats less than the full-length BSSL. The nucleotide sequence of the resulting BSSL variant ("Variant T") is shown in the Sequence Listing as SEQ ID NO: 8. The amino acid sequence of variant T is shown in the Sequence Listing as SEQ ID NO: 9.

Due to the highly repetitive sequence in exon 11 of the human BSSL gene, relatively high frequencies of rearrangements can be anticipated when this sequence is cloned into a plasmid and propagated in bacteria. Based on this assumption, one desired BSSL variant which contains a truncated exon 11, was identified, isolated and subjected to sequence analysis.

Another plasmid, pS283, containing a part of the human BSSL cDNA cloned into the plasmid pUC19 at the HindIII and SacI sites was used for fusion of the genomic sequences. Plasmid pS283 was also used to get a proper restriction enzyme site, KpnI, located in the 5' untranslated leader sequence of BSSL.

Plasmid pS283 was digested with NcoI and SacI and a fragment of about 2.7 kb was isolated by electrophoresis. Plasmid pS309 was digested with NcoI and BspEI and a fragment of about 2.3 kb containing the 5'-part of the BSSL gene was isolated. Plasmid pS310 was digested with BspEI and SacI and a fragment of about 2.7 kb containing a part of the middle region of the BSSL gene was isolated. These three fragments were ligated and transformed into competent E. coli, strain TG2, and transformants were isolated by ampicillin selection.

Plasmids were prepared from a number of transformants, and one plasmid, called pS312 (FIG. 14), containing the desired construct was used for further experiments.

To obtain a modification of pS311 in which the BamHI site located downstream of the stop codon was converted to a SalI site to facilitate further cloning, the following method was used: Plasmid pS311 was linearized by partial BamHI digestion. The linearized fragment was isolated and a synthetic DNA linker that converts BamHI to a SalI site (5'-GATCGTCGAC-3'), thereby destroying the BamHI site, was inserted. Since there were two potential positions for integration of the synthetic linker the resulting plasmids were analyzed by restriction enzyme cleavage. A plasmid with the linker inserted at the desired position downstream of exon 11 was isolated and designated pS313.

To obtain the final expression vector construct harbouring the human BSSL variant genomic sequences an existing expression vector, pS314, designed to mediate stage and tissue specific expression in the mammary gland cells under lactation periods was used. Plasmid pS314 contains a genomic fragment from the murine whey acidic protein (WAP) gene (Campbell et al., 1984) cloned as a NotI fragment. The genomic fragment has approximately 4.5 kb upstream regulatory sequences (URS) all the four murine WAP exons and all intron sequences and about 3 kb of sequence downstream of the last exon. A unique KpnI site is located in the first exon 24 bp upstream of the natural WAP translation initiation codon. Another unique restriction enzyme site is the SalI site located in exon 3.

The human BSSL variant genomic sequence was inserted between these sites, KpnI and SalI, by the following strategy: First, pS314 was digested with KpnI and SalI and a fragment representing the cleaved plasmid was electrophoretically isolated. Second, pS312 was digested with KpnI and BamHI and a approximately 4.7 kb fragment representing the 5'-part of the human BSSL gene was isolated. Third, pS313 was digested with BamHI and SalI and the 3'-part of the human BSSL gene was isolated. These three fragments were ligated, transformed into competent E. coli bacteria and transformants were isolated after ampicillin selection.

Plasmids were prepared from several transformants and carefully analyzed by restriction enzyme mapping and sequence analysis. One plasmid representing the desired expression vector was defined and designated pS317 (FIG. 15).

In order to remove the prokaryotic plasmid sequences, pS317 was digested with NotI. The recombinant vector element consisting of murine WAP sequence flanking the human BSSL variant genomic fragment was then isolated by agarose electrophoresis. The isolated fragment was further purified using electroelution, before it was injected into mouse embryos.

The recombinant gene for expression of human BSSL variant in milk from transgenic mice is shown in FIG. 16.

3.2. GENERATION OF TRANSGENIC ANIMALS

A NotI fragment was isolated from the plasmid pS317 according to section 3.1. This DNA fragment contained the murine WAP promoter linked to a genomic sequence encoding human BSSL variant. The isolated fragment, at a concentration of 3 ng/$\mu$l, was injected into the pronucleus of 350 C57B1/6J×CBA/2J-$f_2$ embryos obtained from donor mice primed with 5 IU pregnant mare's serum gonadotropin for superovulation. The C57B1/6J×CBA/2J-$f_1$ animals were obtained from Bomholtgård Breeding and Research Centre LTD, Ry, Denmark. After collection of the embryos from the oviductsm, they were separated from the cumulus cells by treatment with hyaluronidase in the medium M2 (Hogan et al., 1986). After washing the embryos were transferred to the medium M16 (Hogan et al., 1986) and kept in an incubator with 5% $CO_2$-atmosphere. The injections were performed in a microdrop of M2 under light paraffin oil using Narishigi hydraulic micromanipulators and a Nikon inverted microscope equipped with Nomarski optics. After injection, 267 healthy looking embryos were implanted into 12 pseudopregnant C57B1/6J×CBA/2j-$f_1$ recipients given 0.37 ml of 2.5% Avertin intraperitoneally. Mice that had integrated the transgene were identified with PCR analysis of DNA from tail biopsy specimens obtained three weeks after birth of the animals. Positive results were confirmed with Southern blot analysis.

For milk collection, female lactating animals were injected with 2 IU oxytocin intraperitoneally and 10 minutes later anaesthetized with 0.40 ml of 2.5% Avertin intraperitoneally. A milk collecting device was attached to the nipple via a siliconized tubing and milk was collected into a 1.5 ml Eppendorf tube by gentle massage of the mammary gland. The amount of milk varied, dependent on the day of lactation, between 0.1 and 0.5 ml per mouse and collection.

3.3. EXPRESSION OF BSSL VARIANT IN TRANSGENIC MICE

Transgenic mice were identified by analysis of DNA which has been prepared from excised tail samples. The tissue samples were incubated with proteinase K and phenol/chloroform extracted. The isolated DNA was used in polymerase chain reactions with primers which amplify specific fragments if the heterologous introduced DNA representing the expression vector fragment is present. The animals were also analyzed by DNA hybridization experiments to confirm PCR data and to test for possible rearrangements, structure of the integrated vector elements and to obtain information about the copy number of integrated vector elements.

In one set of experiments, 31 mice were analyzed with the two methods and the results demonstrated that 1 mice was carrying the heterologous DNA vector element derived from pS317. The result from the PCR analysis and the hybridization experiments were identical (FIG. 17). In total, 10 of 65 tested animals were found to be transgenic for pS317.

The mouse identified to carry vector DNA element (founder animal) was then mated and the F1 litter was analyzed for transgene by the same procedures.

RNA isolated from various tissues of pS317 transgenic females during lactation have been separated by agarose formaldehyde gel electrophoresis, blotted to membranes and hybridized with $^{32}$P-labelled BSSL cDNA as a probe. The obtained results show that the expression is restricted to the mammary gland during lactation (FIG. 18).

Milk samples were collected from the anesthetized founder animal treated with oxytocin to induce lactation and analyzed for the presence of recombinant human BSSL variant. This was done by SDS-PAGE, transfer to nitrocellulose membranes and incubation with polyclonal antibodies generated against native human BSSL. The obtained results demonstrated expression of recombinant human BSSL variant in milk from transgenic mice. FIG. 19 demonstrates presence of recombinant human BSSL variant in milk from transgenic mice. SDS-PAGE separation and immunoblotting of milk samples derived from various pS317 transgenic mice show efficient production of a recombinant BSSL variant with reduced apparent molecular weight in comparison to full-length recombinant BSSL derived from milk of a mouse transgenic for pS314. The plasmid pS314 is similar to pS317, with the exception that pS314 contains full-length human BSSL cDNA instead of the genomic variant. The doublet band which is apparent in all murine milk samples is representing murine BSSL, and thus shows the cross reactivity of the antiserum. This conclusion is further supported by the observation that this doublet band is apparent in lane 9 of FIG. 19, which contains purified murine BSSL.

Stable lines of transgenic animals are generated.

In a similar manner, other transgenic animals such as rabbits, cows or sheep capable of expressing human BSSL variants may be prepared.

DEPOSITS

The following plasmids have been deposited in accordance with the Budapest Treaty at DSM (Deutsche Sammlung von Mikroorganismen und Zellkulturen):

| Plasmid | Deposit No. | Date of deposit |
|---------|-------------|-----------------|
| pS309   | DSM 7101    | 12 June 1992    |
| pS310   | DSM 7102    |                 |
| pS311   | DSM 7103    |                 |
| pS317   | DSM 7104    |                 |
| pS147   | DSM 7495    | 26 February 1993 |
| pS257   | DSM 7496    |                 |
| pS299   | DSM 7497    |                 |
| pS258   | DSM 7501    | 3 March 1993    |
| pS259   | DSM 7502    |                 |

A. Map of the BPV based vector used for expression of the different BSSL variants.

B. A schematic representation of the different BSSL variants analyzed. FL denotes the full-length BSSL. The active site is indicated by a circle and the site for the potential N-linked carbohydrate is indicated by a triangle. The region containing the repeats is indicated as a striped area and the conserved C-terminal as a filled area.

FIG. 2

Southern blot analysis of DNA from cell lines expressing BSSL variants. DNA prepared from cell lines expressing full-length BSSL (FL), variant A (A), variant B (B), variant C (C) and variant N (N) were analyzed. 5 μg of the respective prepared cell derived DNA (left) and 1 ng of purified bacteria derived vector DNA (right), were digested with BamHI. The DNA samples were separated on an agarose gel, transferred to GeneScreen Plus membrane and hybridized with $^{32}$P-labelled human BSSL cDNA.

FIG. 3

Figure 1A:
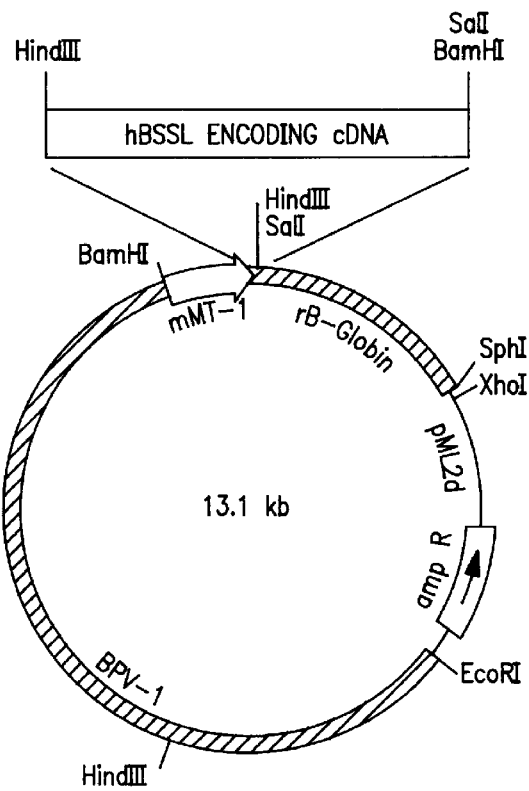
FIGS 1A and 1B
Figure 1B:
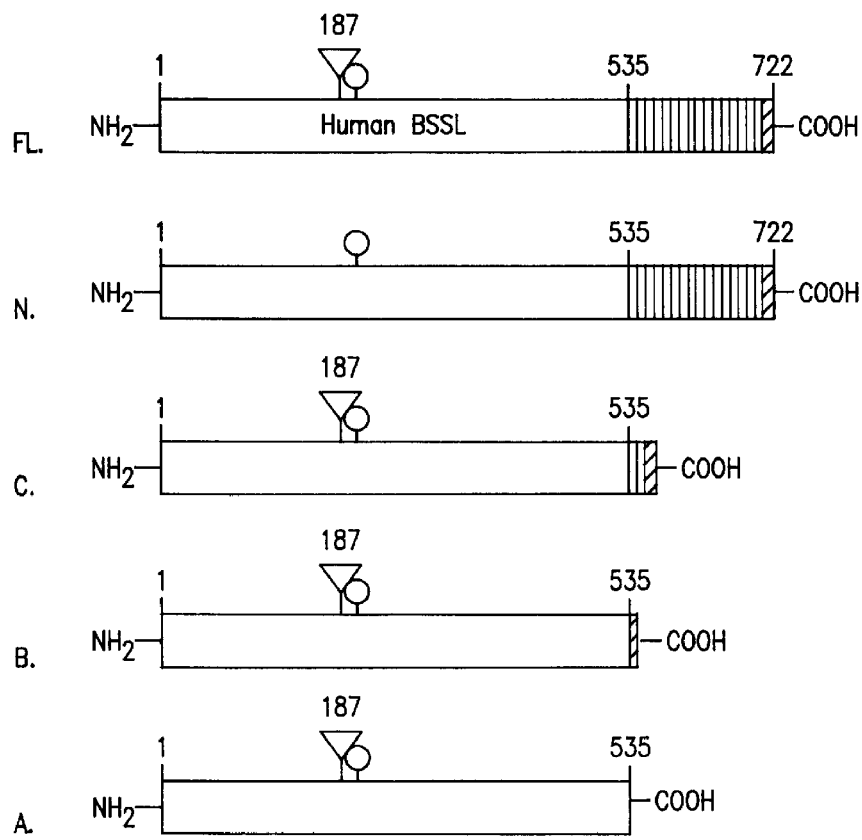

Northern blot analysis of RNA from isolated cell lines expressing recombinant BSSL variants. 10 μg of total RNA prepared from cell lines producing full-length BSSL (FL), variant A (A),variant B (B), variant C (C), variant N (N) were analyzed. RNA from a C127 cell line harboring a BPV-vector identical to the vector in FIG. 1, except for that it encodes a protein unrelated to BSSL, was used as negative control (−) (upper panel). Filters were hybridized with 32P-labelled BSSL cDNA. The filter was then rehybridized with a murine β-actin cDNA probe. The β-actin mRNA signals (lower panels) were used as an internal control for the amounts of RNA loaded onto each lane.

FIG. 4

Expression of BSSL activity in C127 cells transfected with full-length and mutated forms of human BSSL. C127 cells were transfected with different BSSL-constructs: full-length BSSL (FL), variant N (N), variant C (C), variant B (B), variant A (A). After the initial growth period individual clones were selected and allowed to grow until confluency. The number of selected clones (n) are indicated in the figure. Lipase activity was determined on the conditioned media. Values are expressed as μmol free fatty acid released×min$^{-1}$×ml of conditioned medium$^{-1}$.

FIG. 5

A. Western blotting of full-length and mutated recombinant BSSL. The amounts of lipase activity, expressed as μmol fatty acid released×min$^{-1}$, applied to the gel was: Full-length 0.2 (lane 1), variant N 0.16 (lane 2), variant C 0.6 (lane 3), variant B 0.8 (lane 4) and native BSSL 0.1 (lane 5). The antiserum used was raised in rabbit against BSSL purified from human milk. The position of size markers (Prestained SDS-PAGE Standards, Low Range, BioRad) are indicated to the left.

B. Western blot of N-glycosidase F treated variant B. Variant B was digested with N-glycosidase F as described in Experimental procedures. Lane 1 shows untreated and lane 2 treated variant B.

FIG. 6

Bile salt-dependency of full-length and mutated BSSL. Lipase activity was determined in the presence of varying concentrations of sodium cholate (solid lines) or sodium deoxycholate (broken lines) on conditioned media from full-length recombinant BSSL (*), variant A (□), variant B (▲), variant C (■), variant N (●) and purified human milk BSSL (○). For the A variant conditioned medium was concentrated on Blue Sepharose as described under Experimental procedures. The amount of the respective enzyme source was chosen to obtain the same level of maximal activity except for variant A which had a maximal activity of only one-tenth of the others. Control experiments showed that the growth media did not influence the level of activity or the bile salt dependency of native BSSL (data not shown).

FIG. 7

A. Northern blot of BSSL produced by different strains of E.coli using pGEMEX. The bacteria were induced by IPTG as described in experimental procedures.

Figure 2:
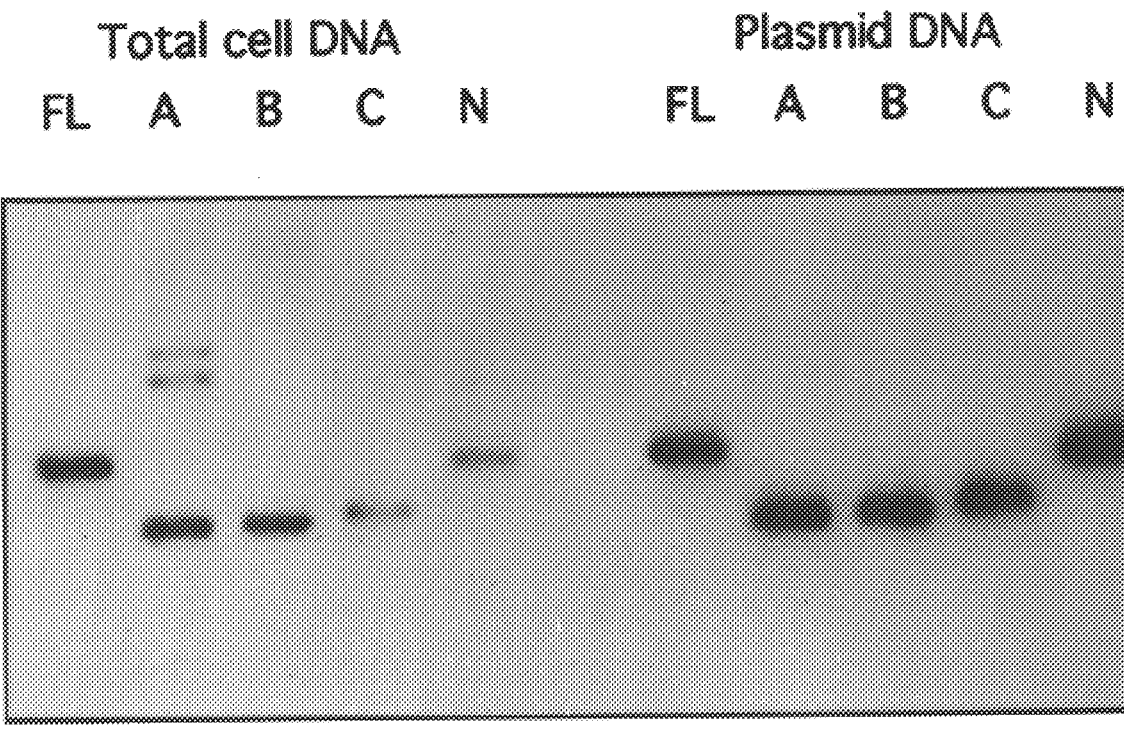
Figure 3:
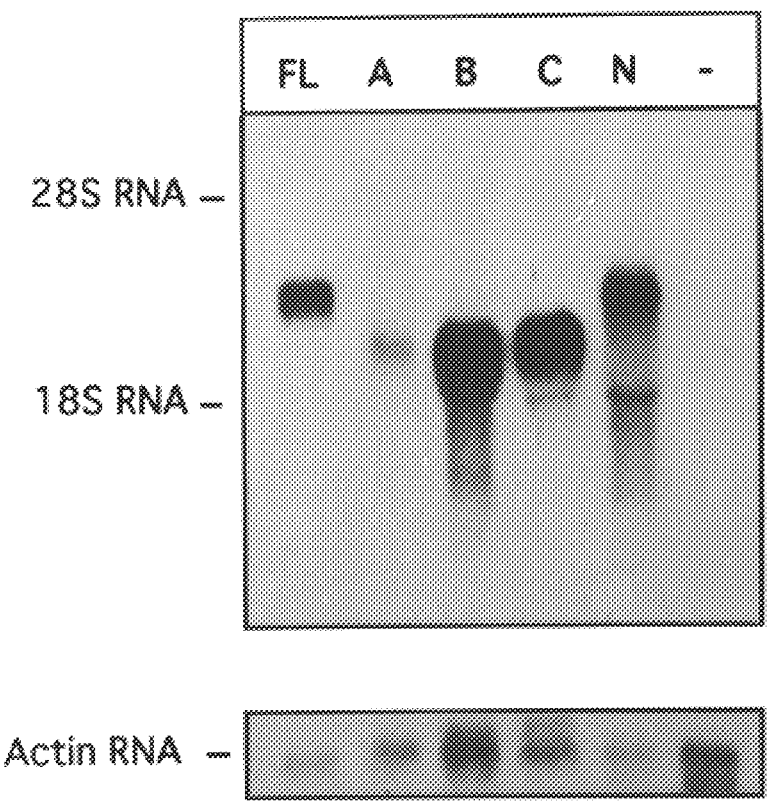
Figure 4A:
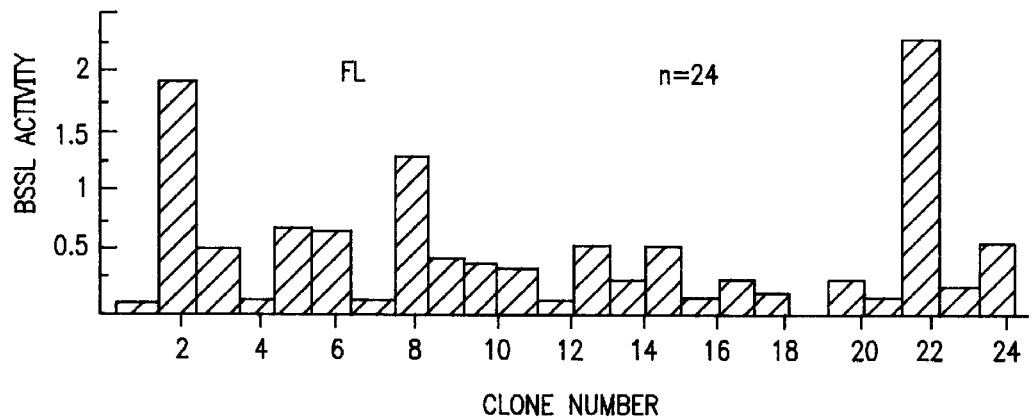
Figure 4B:
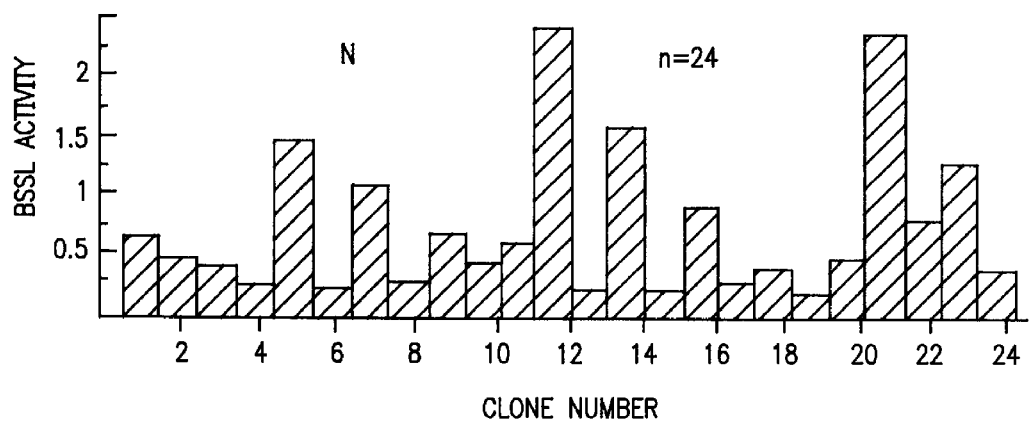
Figure 4C:
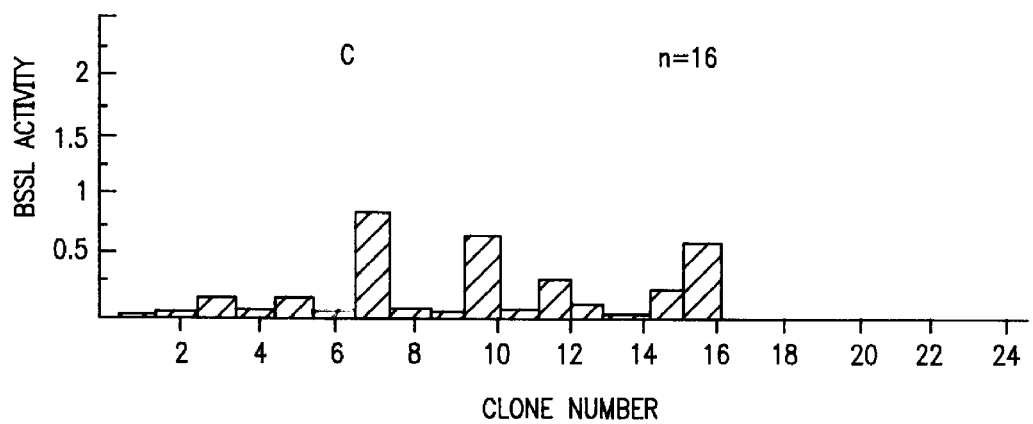
Figure 4D:
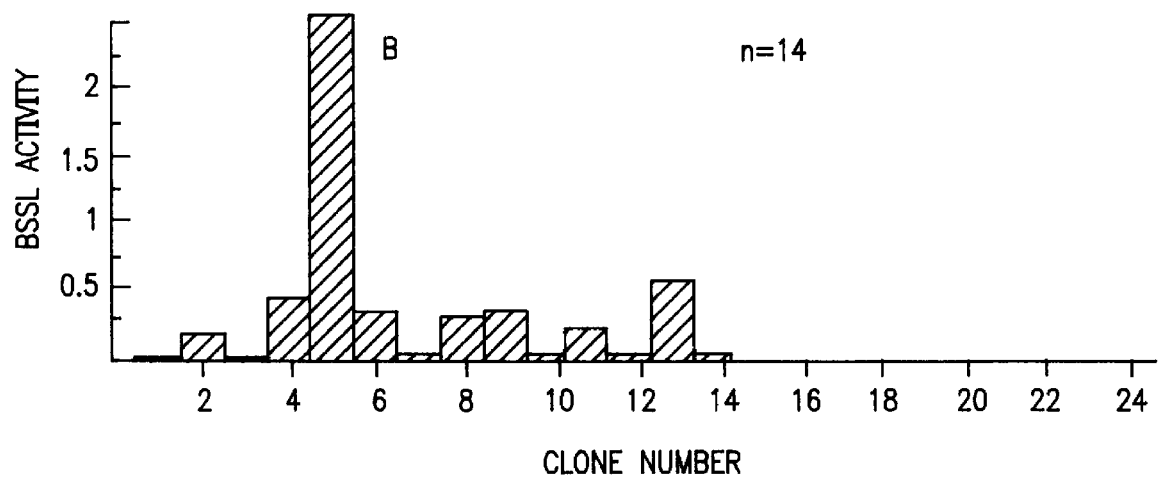
Figure 4E:
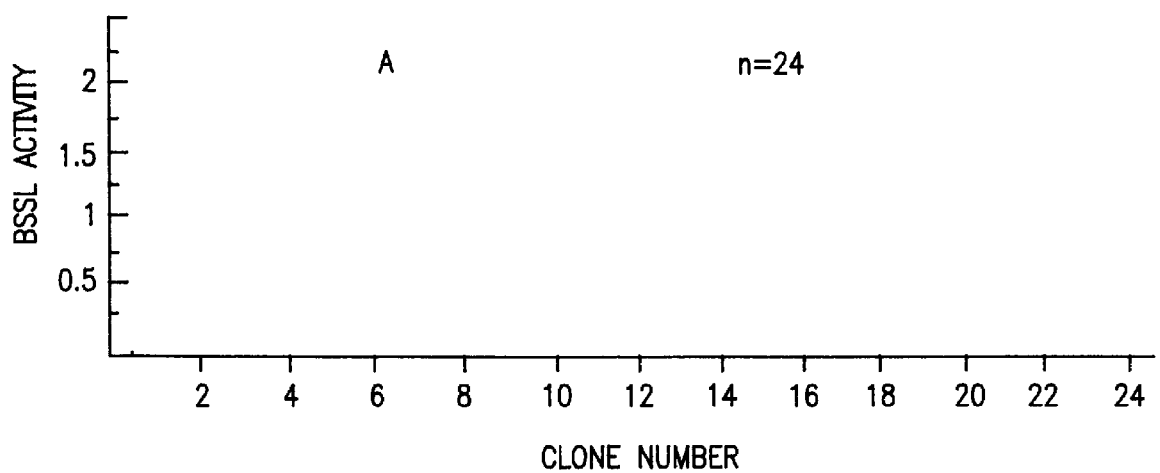
Figure 5A:
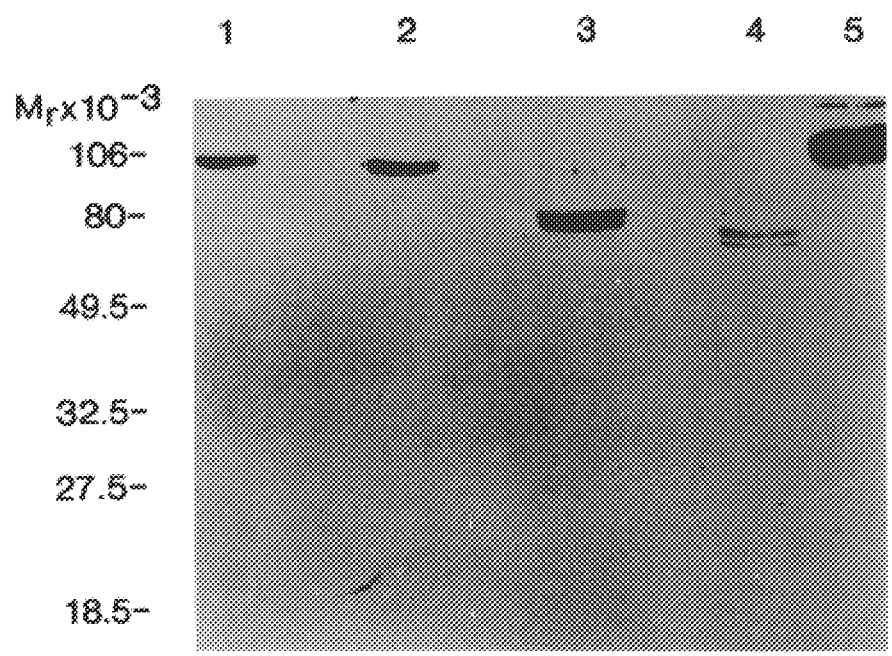
Figure 5B:
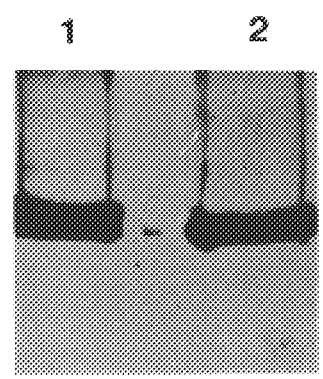
Figure 6:
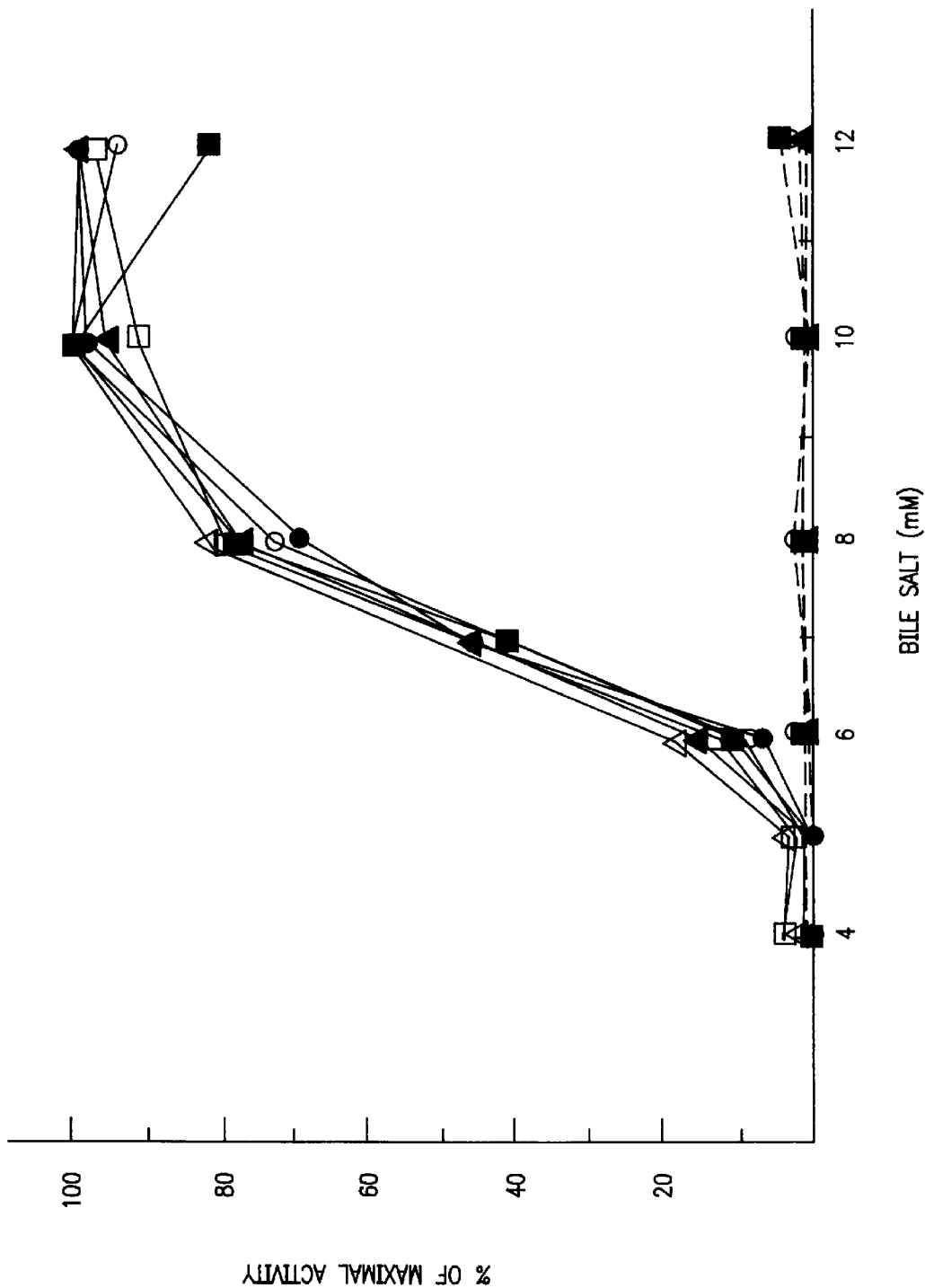
Figure 7A:
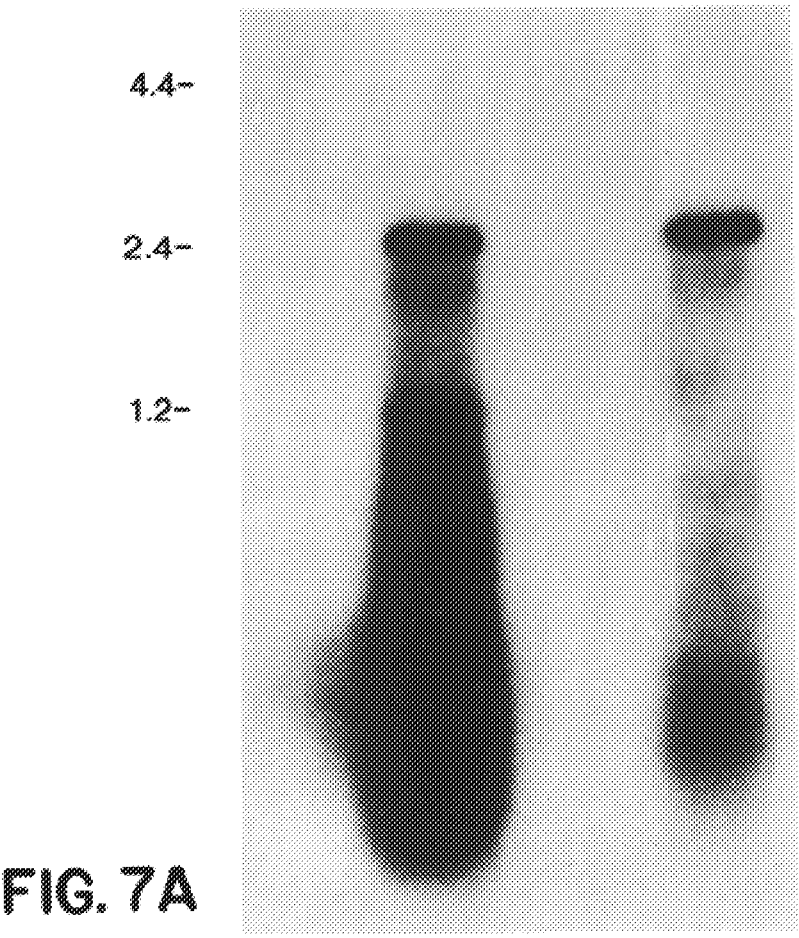
Figure 7B:
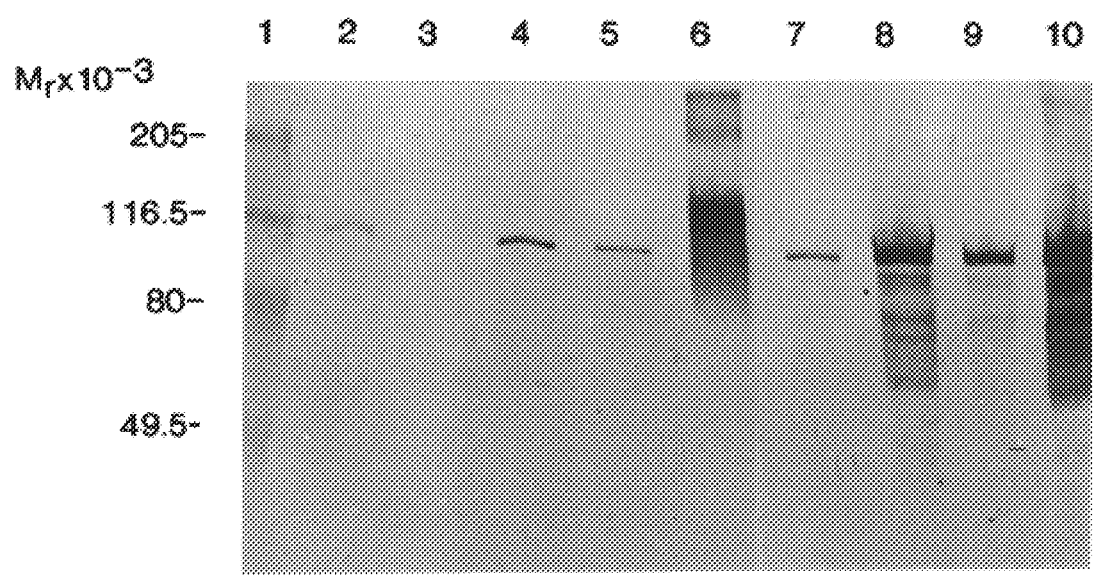
Figure 8:
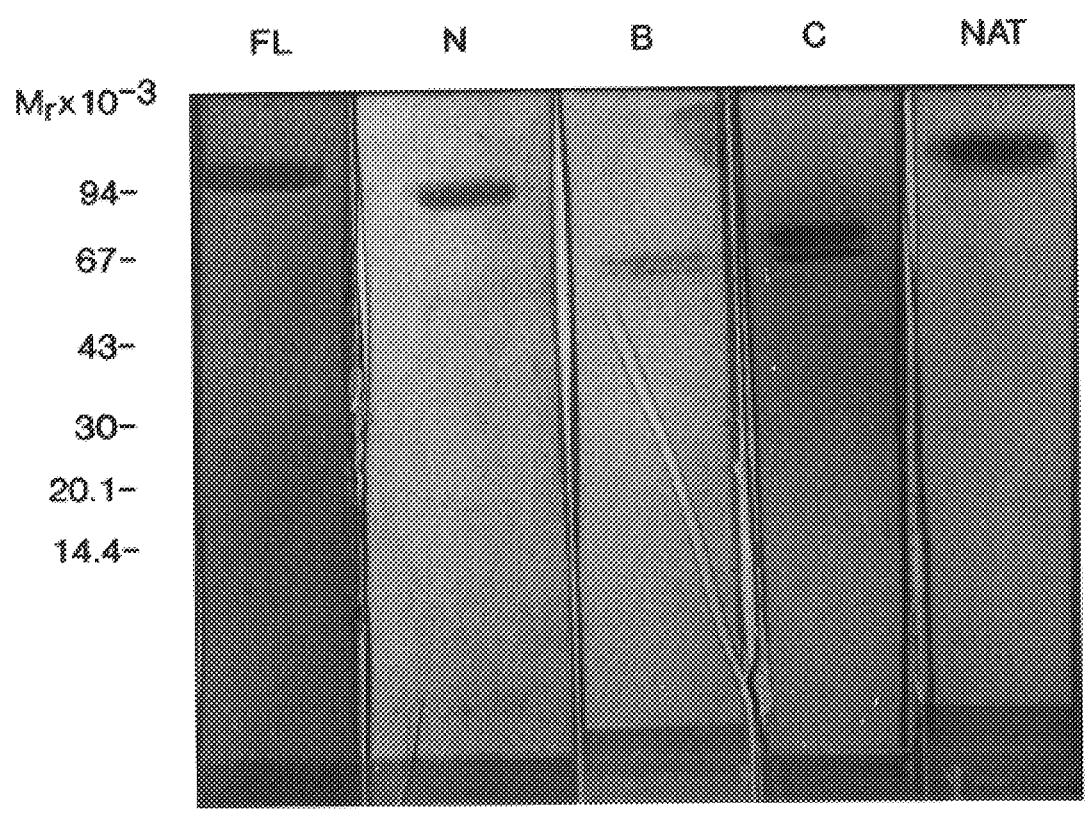

Experimental conditions were as described in the legend to FIG. 2. Lane 1, strain BL21(DE3)pLysS, not induced; Lane 2, strain BL21(DE3)pLysS, induced; Lane 3, strain JM109(DE3), not induced; Lane 4, strain JM109(DE3), induced.

B. Western blot, using antibodies to purified milk BSSL, of an 8–18% SDS-PAGE showing the expression of recombinant BSSL in different strains of E.coli using pGEMEX.

Bacteria were induced with IPTG, and cytoplasmic and periplasmic proteins prepared from lysate as described in experimental procedures. The amounts of bacterial proteins loaded in lane 2–5 (periplasmic preparations) and 7–10 (cytoplasmic preparations) represent the same culture volume making the stain proportional to the production level. Lane 1, Pharmacia molecular size markers; Lanes 2 and 8, strain JM109(DE3), induced; Lanes 3 and 7, strain JM109 (DE3), not induced; Lanes 4 and 10, strain BL21(DE3) pLysS, induced; Lanes 5 and 9, strain BL21(DE3)pLysS, not induced; Lane 6, 25 ng of purified native milk BSSL.

FIG. 8

SDSPAGE of purified recombinant BSSL and BSSL variants. Full-length recombinant BSSL (FL) and BSSL variants N, B, and C were purified as described. 3 µg of each was applied, except for variant B, of which 1.5 µg was used. 5 µg of purified native milk BSSL (NAT) was applied. The position of size markers are indicated to the left.

FIG. 9

Effect of sodium deoxycholate on the activation of recombinant BSSL and BSSL variants by sodium cholate. Purified preparations of recombinant full-length BSSL (●), recombinant BSSL variants B (○), C (■) and N (▲), and purified native milk BSSL (□) were assayed for lipase activity with different concentrations of sodium cholate in the absence (left panel) and in the presence of 5 mM (centre panel) or 10 mM (right panel) deoxycholate.

FIG. 10

Figure 9:
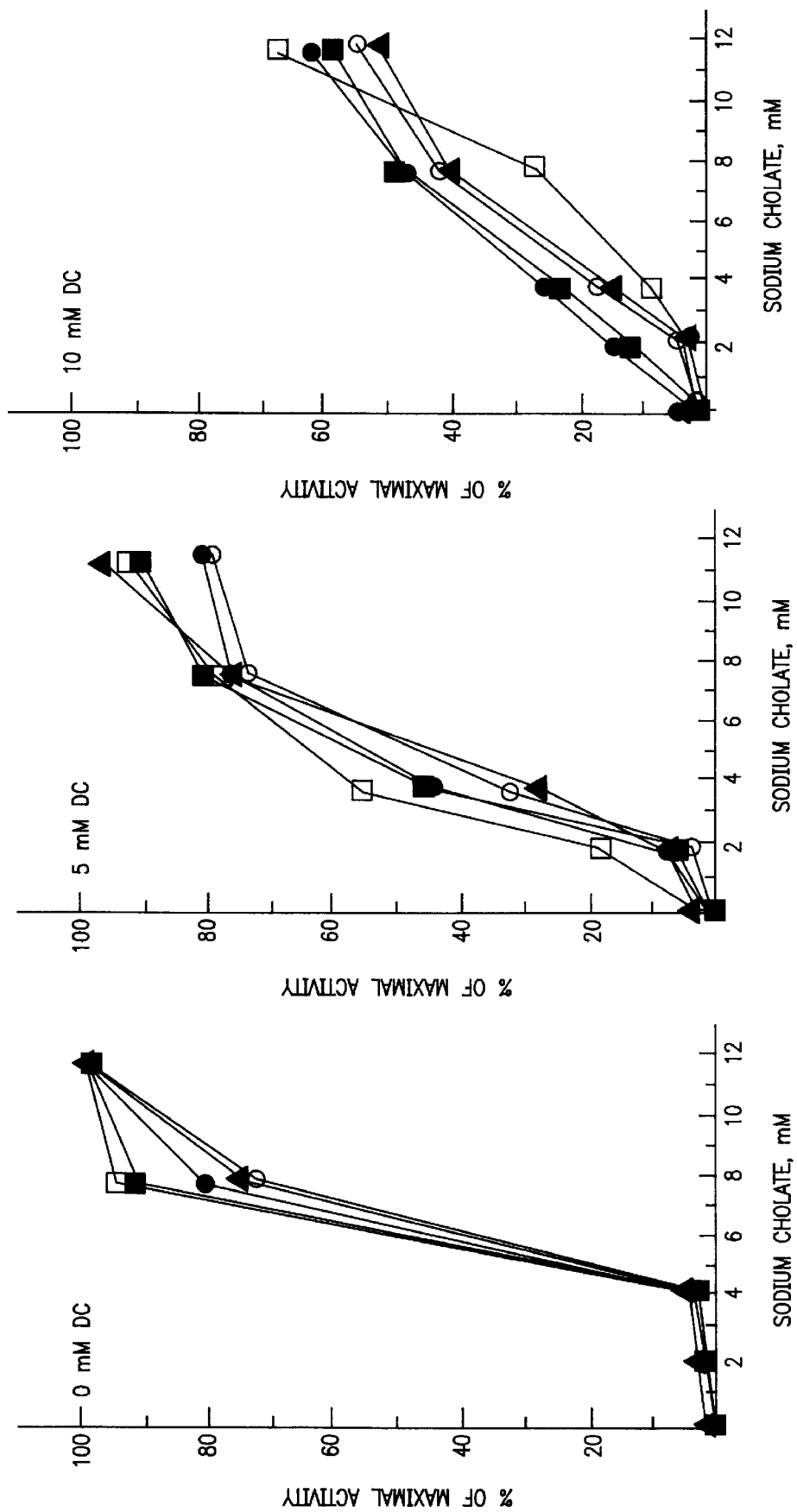
Figure 10:
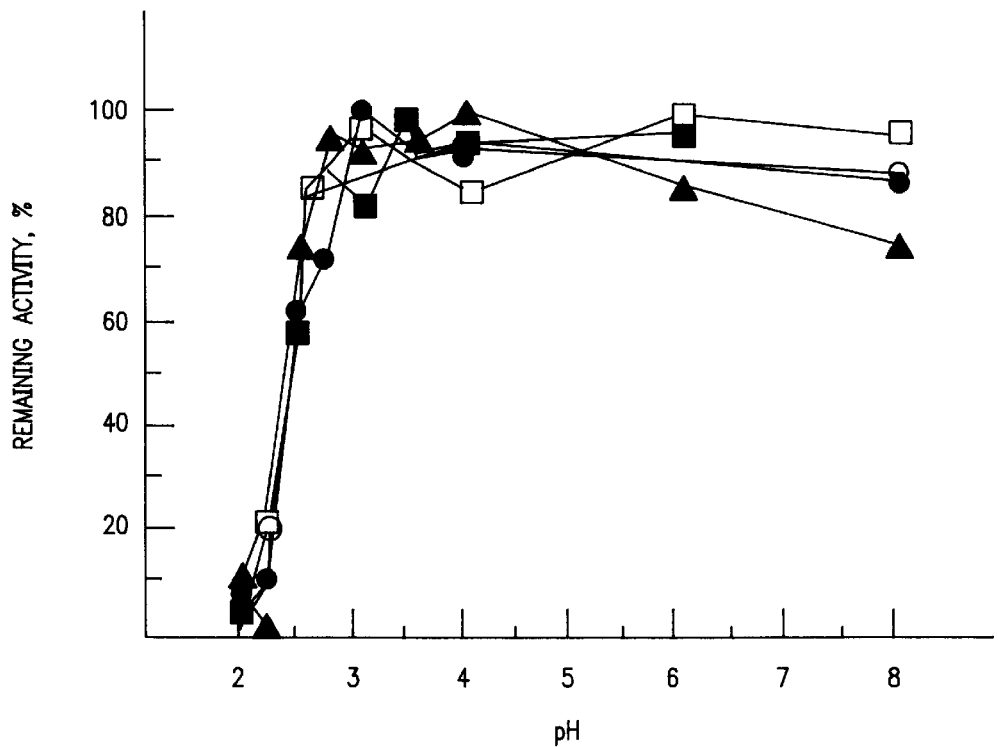
Figure 11:
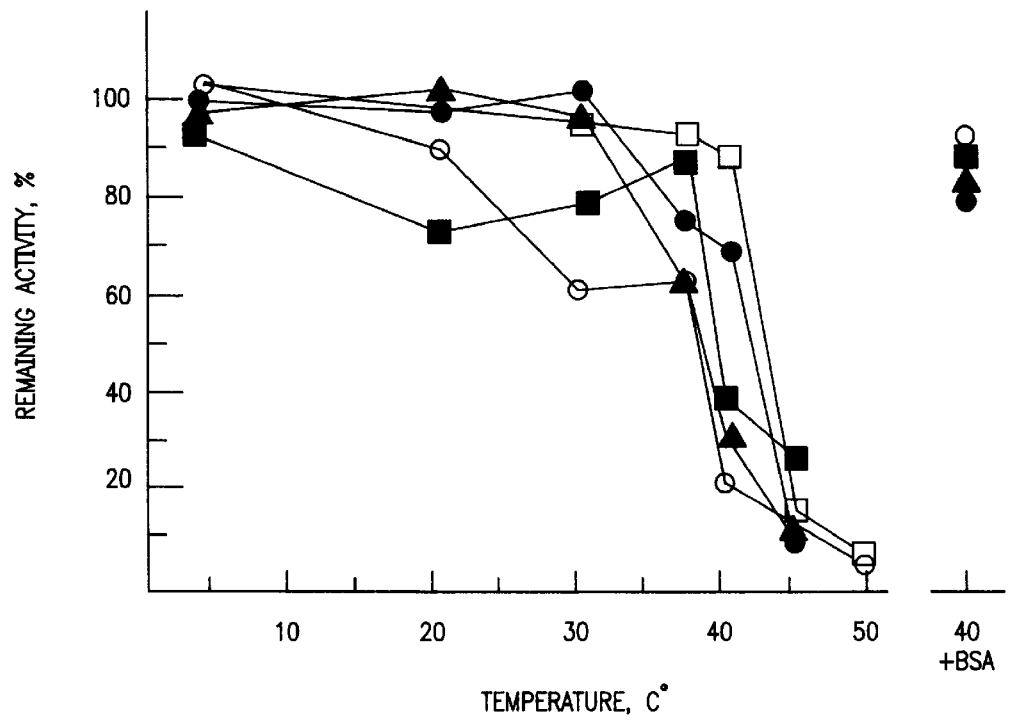
Figure 12:
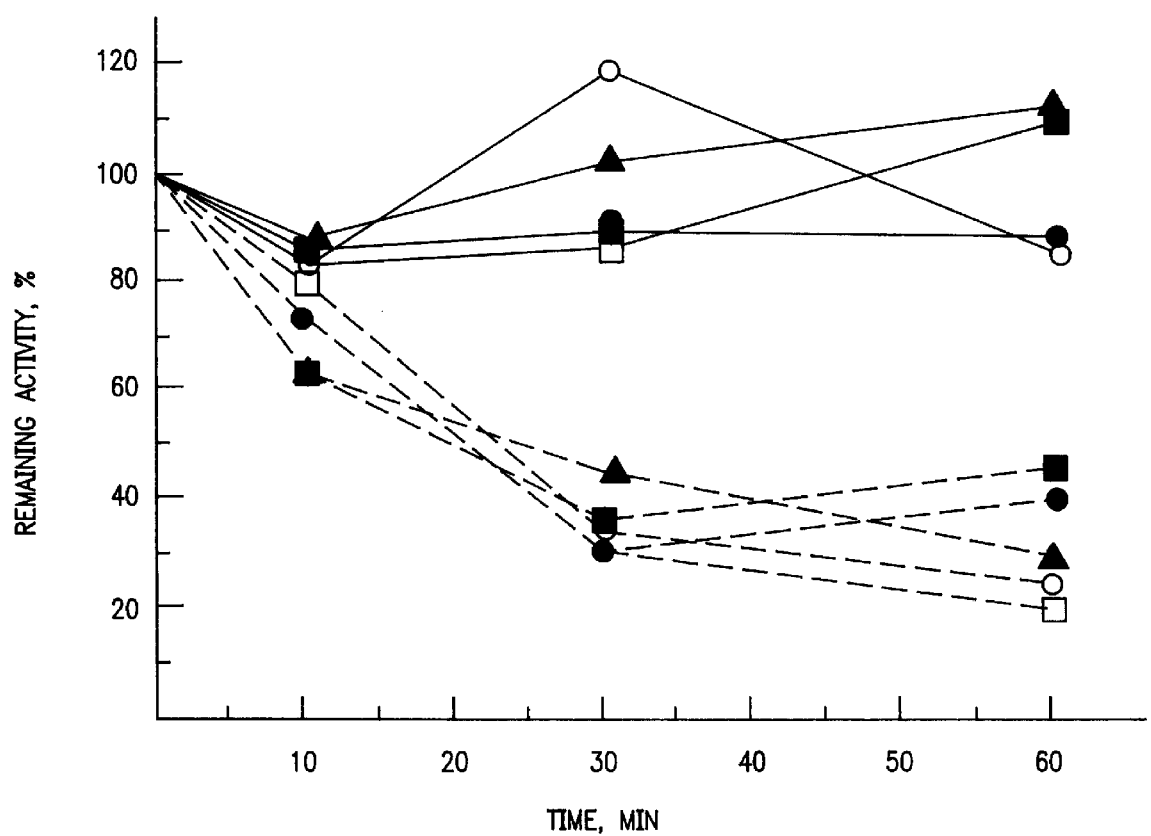
Figure 13:
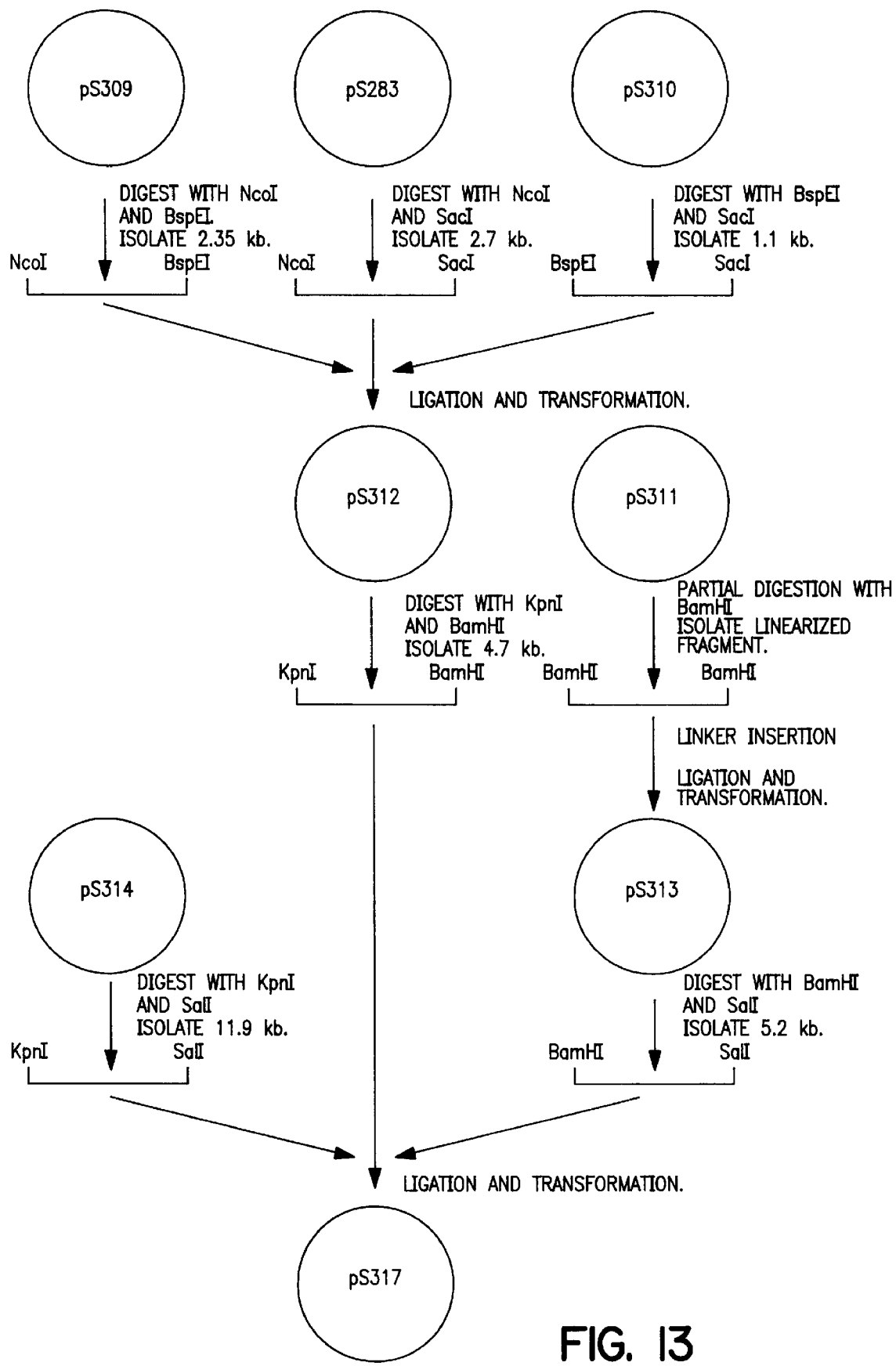
Figure 14:
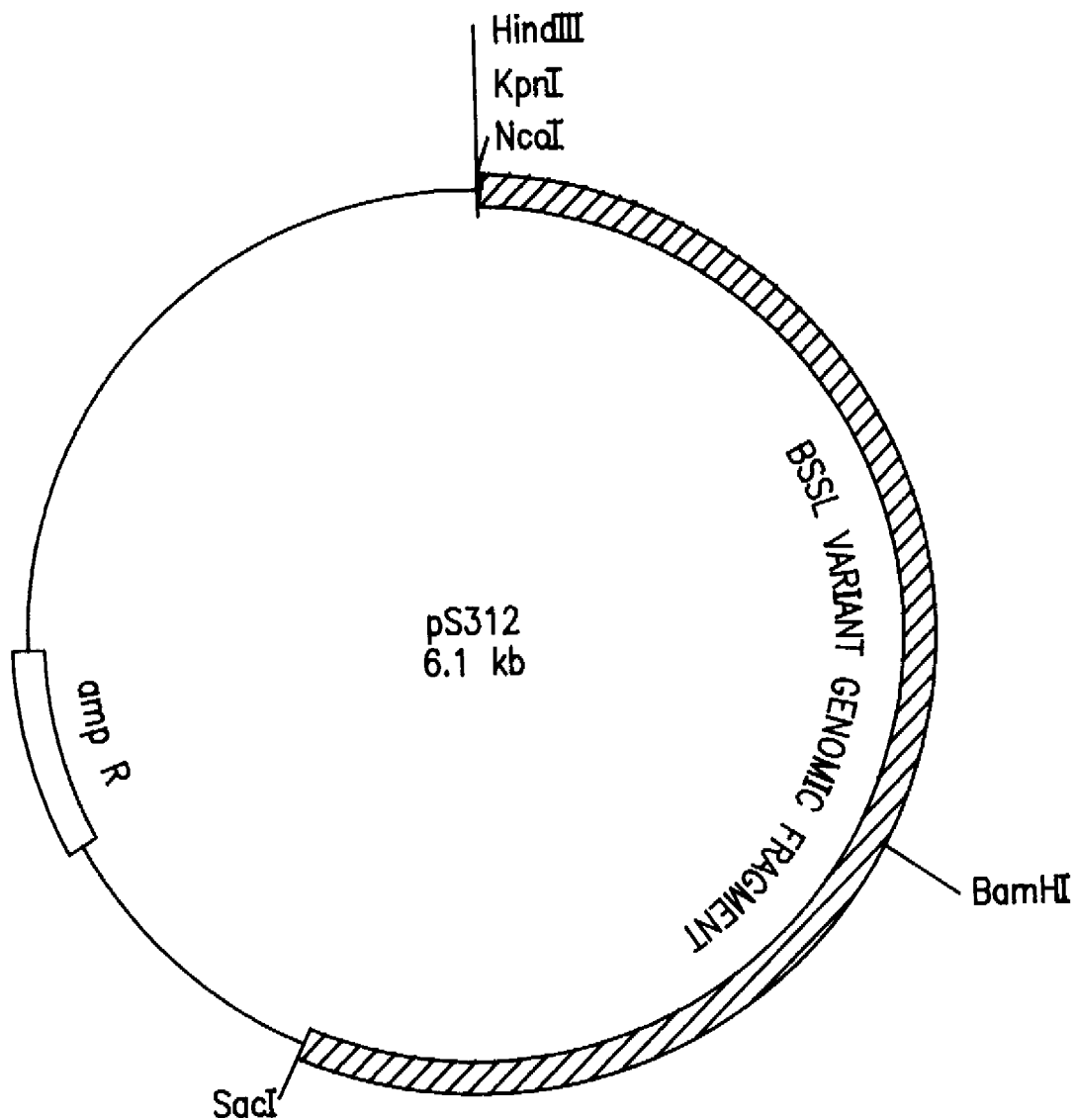
Figure 15:
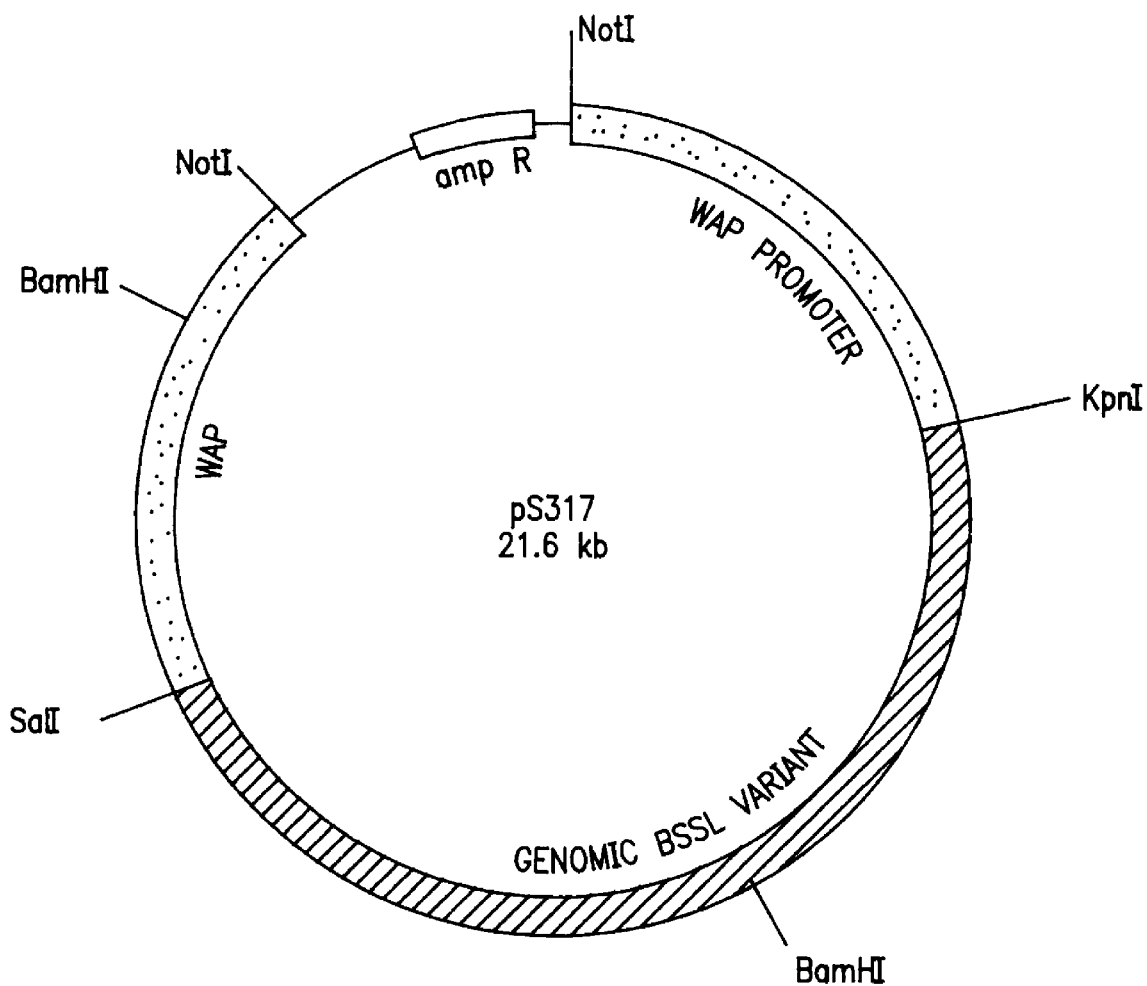
Figure 16:
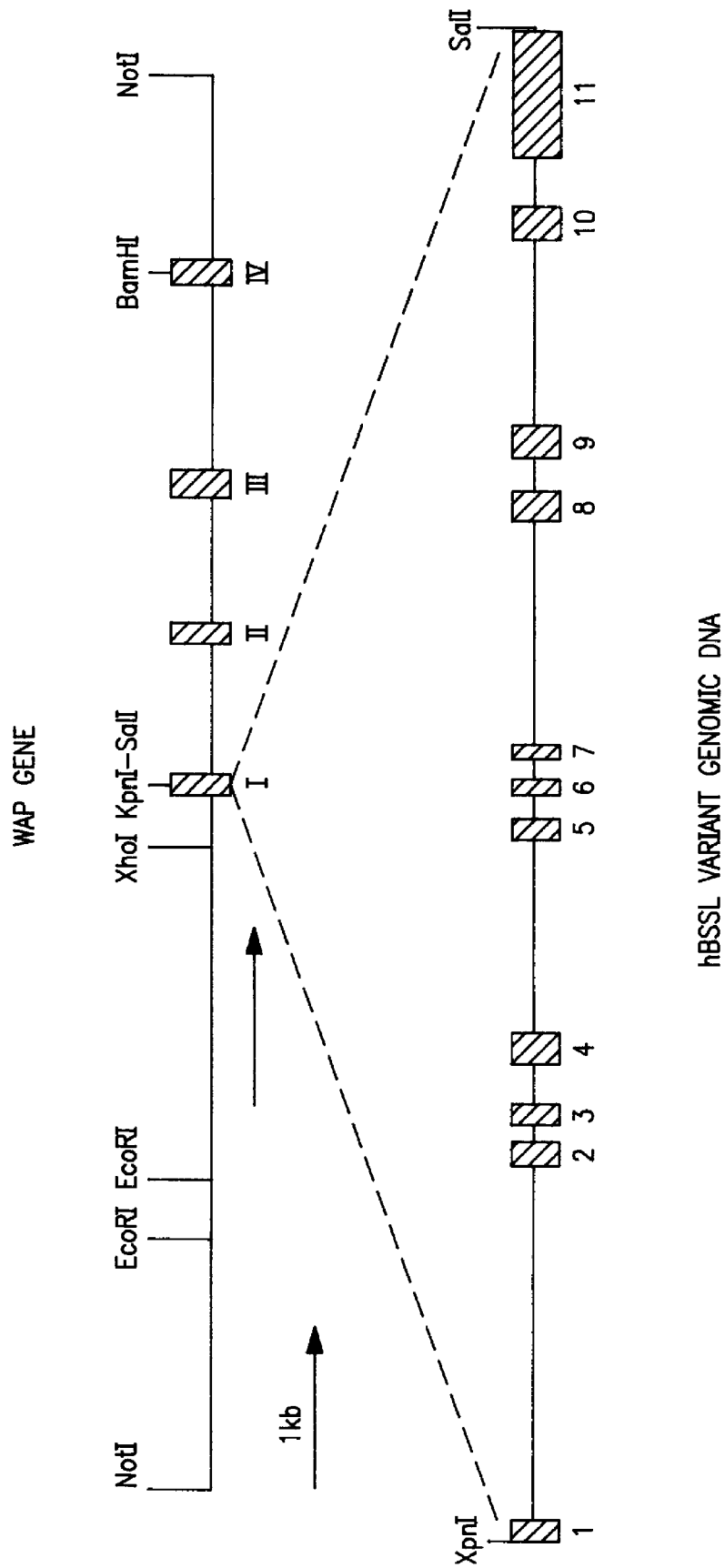
Figures 17A, 17B:
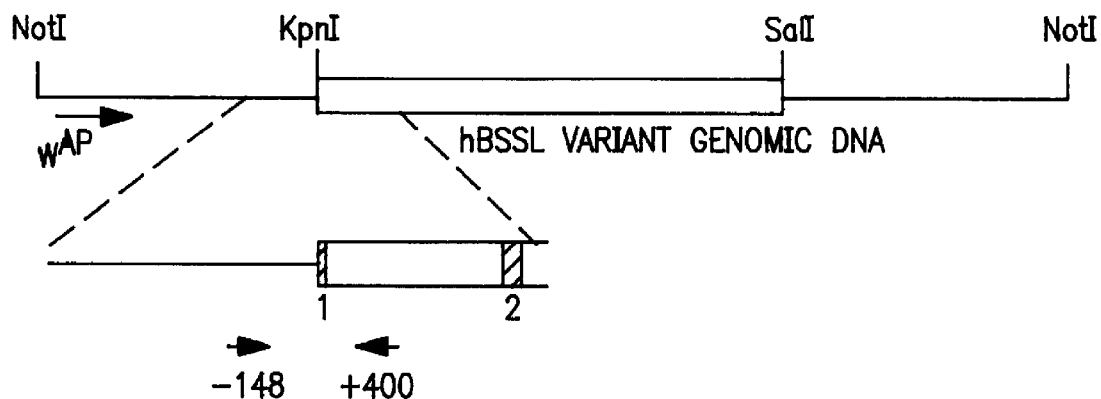
Figure 17C:
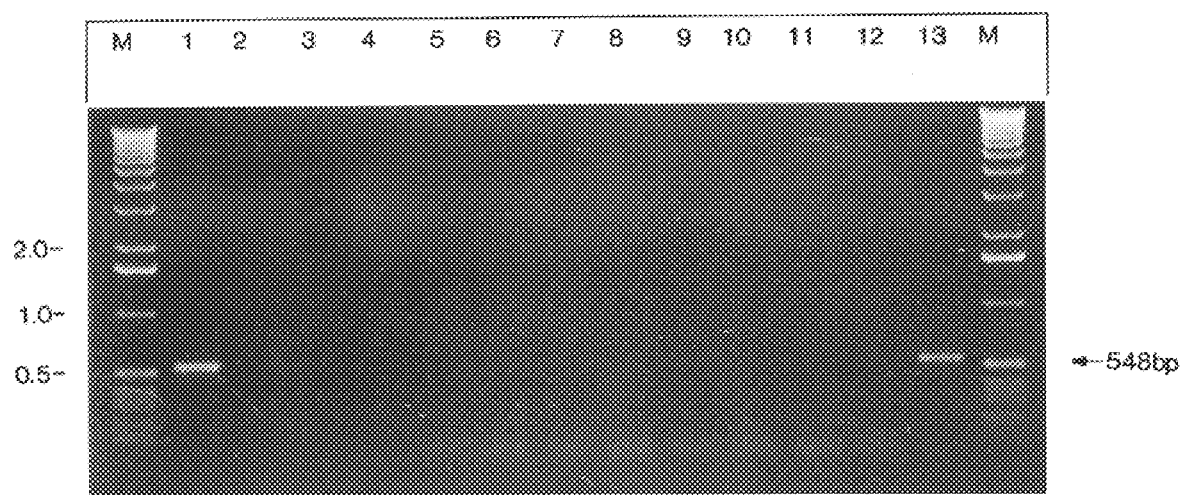
Figure 18:
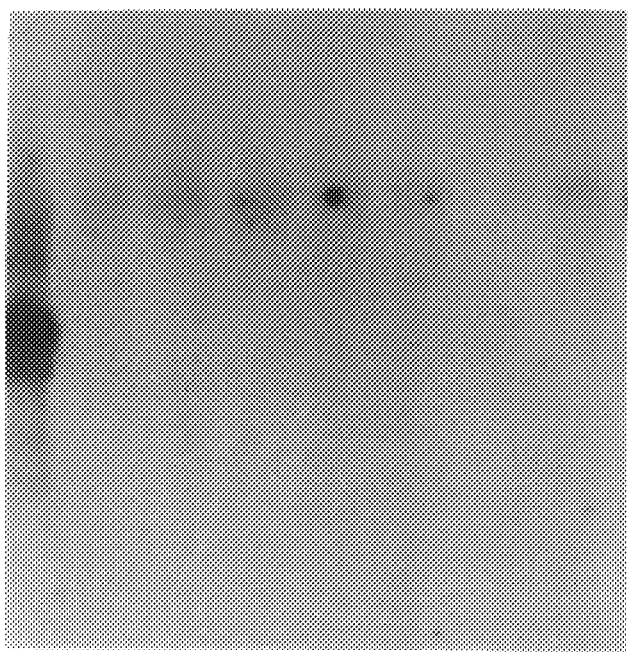
Figure 19:
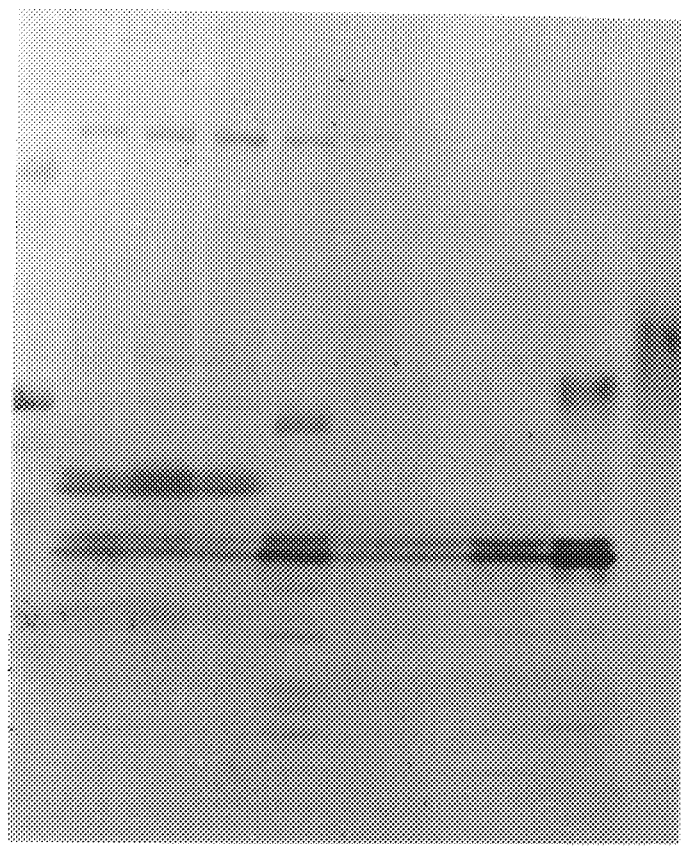

Stability of recombinant BSSL and BSSL variants at different pH. Native BSSL, recombinant full-length BSSL and BSSL variants were incubated at 37° C. in different buffers with pH 2–8. All buffers contained 1 mg/ml of bovine serum albumin. After 30 min aliquotes were withdrawn and assayed for lipase activity. For explanation of symbols, see the legend to FIG. 9.

FIG. 11

Heat stability of recombinant BSSL and BSSL variants. Purified recombinant full-length BSSL, BSSL variants and native milk BSSL were incubated at the temperatures indicated in 50 mM Tris-Cl buffer, pH 7.5. To one set of samples bovine serum albumin (BSA) was added to 1 mg/ml. After 30 min samples were withdrawn and assayed for lipase activity. Activities are expressed as percent of the activity for each sample at 0 min. For explanation of symbols, see the legend to FIG. 9.

FIG. 12

Effect of bile salts on the inactivation of recombinant BSSL and BSSL variants by trypsin. Purified recombinant full-length BSSL, BSSL variants and native milk BSSL (15 µl containing 1–4 µg) were added to 60 µl of 1.0 M Tris-Cl, pH 7.4 with 10 µg of trypsin (TPCK-trypsin, Boehringer-Mannheim) at 25° C. in the absence (broken lines) and in the presence (solid lines) of 10 mM sodium cholate. At the times indicated aliqoutes were withdrawn and assayed for lipase activity. Values are expressed as percent of values obtained in control incubations in the absence of trypsin. For explanation of symbols, see the legend to FIG. 9.

FIG. 13

Method for production of the plasmid pS317. For further details, see section 3.1.

FIG. 14

Schematic structure of the plasmid pS312.

FIG. 15

Schematic structure of the plasmid pS317.

FIG. 16

Physical map representing the physical introduction of human BSSL variant genomic structure in the first exon of the WAP gene as described in section 3.1.

FIGS. 17A–17C

A. Schematic representation of the localization of PCR-primers used for identification of transgenic animals. The 5'-primer is positioned within the WAP sequence starting at the position -148 bp upstream of the fusion between the WAP and BSSL variant. The 3'-primer is localized in the first BSSL variant intron ending 400 bp downstream of the fusion point.

B. The sequences of the PCR primers used.

C. Agarose gel showing a typical analysis of the PCR analysis of the potential founder animals. M: molecular weight markers. Lane 1: control PCR-product generated from the plasmid pS317. Lanes 2–13: PCR reactions done with DNA preparations from potential founder animals.

FIG. 18

Northern blot analysis of RNA prepared from various tissues isolated from a female mouse transgenic for pS317. The tissues were isolated at day four of lactation. 10 µg of total RNA from each tissue was analyzed by agarose-formaldehyde separation, transferred to membranes and hybridized with $^{32}$P-labelled human BSSL cDNA. The lanes contain Mg: mammary gland; Li: liver; Ki: kidney; Sp: spleen; He: heart; Lu: lung; Sg: salivary gland; Br: brain. RNA sizes in nucleotides are indicated to the left.

FIG. 19

Western blotting of milk obtained from pS317 transgenic mice, and mice transgenic for a full-length cDNA vector pS314 and control animals. The samples were separated by SDS-PAGE and transferred to Immobilon filters and immunoblotted with antiserum raised against native human BSSL. Lane 1: molecular weight markers; Lanes 2,3 and 4:2 µl milk from three F1 daughters (F1 30, 31, and 33) of pS317 founder F0 #91; Lane 5:2 µl milk from pS314 founder #90. Lanes 6, 7 and 8:2 µl milk from three non-BSSL transgenic animals; Lane 9: purified murine BSSL; Lane 10: purified human native BSSL.

REFERENCES

Abouakil, N., Rogalska, E., and Lombardo, D. (1989): Biochim. Biophys. Acta 1002, 225–230

Atkinson, S. A., Bryan, M. H., and Andersson, G. H. (1981): J. Pediatr. 99, 617–624

Ausubel, F. M., Brent, R., Kingston, R. E., Moore, D. D., Seidman, J. G., Smith, J. A., Struhl, K. (eds.) in: Current Protocols in Molecular Biology (John Wiley & Sons, New York; edition of 1992)

Baba, T., Downs, D., Jackson, K. W., Tang, J. and Wang, C. S. (1991): Biochemistry 30, 500–510.

Bernbäck, S., Bläckberg, L., and Hernell, O. (1990): J. Clin. Invest. 85, 1221–1226

Björksten, B., Burman, L. G., deChateau, P., Fredrikzon, B., Gothefors, L. & Hernell, O. (1980): Br. Med. J. 201, 267–272.

Bläckberg, L. & Hernell, O. (1981): Eur. J. Biochem 116, 221–225.

Bläckberg, L. and Hernell, O. (1983): FEBS Lett. 157, 337–341

Campbell, S. M., Rosen, J. M., Hennighausen, L. G., Strech-Jurk, U. and Sippel, A. E. (1984): Nucleic Acid Res. 12, 8685–8697.

Chappell, J. E., Clandinin, M. T., Kearney-Volpe, C., Reichman, B., and Swyer, P. W. (1986): J. Pediatr. 108, 439–447

Fontaine, R., Carter, C., and Hui, D. (1991): Biochemistry 30, 7008–1014

Graham, F. L., and Van der Eb, A. J. (1973): Virology 52, 456–467

Hamosh, M., Freed, L. M., York, C. M., Sturman, J. A., and Hamosh, P. (1986): Fed. Proc. 45, 1452

Han, J. H., Stratowa, C., and Rutter, W. J. (1987): Biochemistry 26, 1617–1625

Hennighausen, L., Ruiz, L. & Wall, R. (1990): Current Opinion in Biotechnology 1, 74–78.

Hernell, O. (1975): Eur. J. Clin. Invest. 5, 267–272

Hernell, O., Bläckberg, L., and Lindberg, T. in: Textbook of gastroenterology and nutrition in infancy (Lebenthal, E. ed) pp. 209–217 (Raven Press, New York 1989)

Hernell, O., Staggers, J. E. and Carey, M. C. (1990): Biochemistry 29, 2041–2056

Hernell, 0. and Bläckberg, L. in: Encyclopedia of human biology (Dulbecco, R. ed.) Vol. 3, pp. 47–56 (Academic Press, San Diego 1991)

Hernell, O., Bläckberg, L., Chen, Q., Sternby, B. and Nilsson, A. (1993): J. Pediatr. Gastroenterol. Nutr. (In press)

Hogan, B., Constantini, F. and Lacy, E. (1986): Manipulating the mouse embryo. A Laboratory Manual. Cold Spring Harbor Laboratory Press.

Hui, D. and Kissel, J. A. (1990): Febs Lett. 276, 131–134.

Kyger, E. M., Wiegand, R. C., and Lange, L. G. (1989): Biochem. Biophys. Res. Commun. 164, 1302–1309

Laemmli, U. K. (1970): Nature (London) 227, 680–685

Lidberg, U., Nilsson, J., Strömberg, K., Stenman, G., Sahlin, P., Enerbäck, S. G. and Bjursell, G. (1992): Genomics 13, 630–640

Lusky, M., and Botchan, M. R. (1984): Cell 36, 391–401

Nilsson, J., Bläckberg, L., Carlsson, P., Enerbäck, S., Hernell, O. and Bjursell, G. (1990): Eur. J. Biochem. 192, 543–550.

Pavlakis, G. N., and Hamer, D. H. (1983): Proc. Natl. Acad. Sci. USA 80, 397–401

Reue, K., Zambaux, J., Wong, H., Lee, G., Leete, T. H., Ronk, M., Shively, J. E., Sternby, B., Borgström, B., Ameis, D. and Schotz, M. C. (1991): J. Lipid. Res. 32, 267–276.

Sarver, N., Byrne, J. C., and Howell, P. M. (1982): Proc. Natl. Acad. Sci. USA 79, 7147–7151

Studier, F. W. and Moffat, B. A. (1986): J. Mol. Biol. 189, 113–130

Williamson, S., Finucane, E., Ellis, H., and Gamsu, H. R. (1978): Arch. Dis. Childhood 53, 555–563

We claim:

1. A nucleic acid encoding a variant BSSL polypeptide that retains Bile Salt Stimulated Lipase activity, wherein one or more, but not all, of the amino acids in the region corresponding to amino acids 536–722, inclusive, of SEQ ID NO: 3 have been deleted.

2. The nucleic acid according to claim 1, wherein said variant BSSL polypeptide has a phenylalanine at its c-terminus.

3. The nucleic acid according to claim 1, wherein said variant BSSL polypeptide comprises the sequence Gln-Met-Pro within 50 amino acids of its C-terminus.

4. The nucleic acid according to claim 1, wherein said variant BSSL polypeptide comprises the sequence shown as residues 712–722 of SEQ ID NO: 3 within 50 amino acids of its C-terminus.

5. The nucleic acid according to claim 1, wherein said variant BSSL polypeptide comprises fewer than 16 repeat units, said repeat units being those of 33 nucleotides each, designated as such in SEQ ID NO: 1 in the Sequence Listing.

6. The nucleic acid according to claim 11, wherein said variant BSSL polypeptide comprises the amino acid sequence of SEQ ID NO: 5, 6, or 9.

7. A nucleic acid encoding a variant BSSL polypeptide that retains Bile Salt Stimulated Lipase activity, wherein the amino acid sequence of the polypeptide is that shown as SEQ ID NO: 3 in the Sequence Listing except that the nucleic acid encodes for an amino acid other than asparagine at position 187 of the polypeptide.

8. A nucleic acid according to claim 7, wherein the variant BSSL polypeptide comprises the amino acid sequence of SEQ ID NO: 7 in the Sequence Listing.

9. A hybrid gene comprising a nucleic acid according to claim 1 or 2 operably linked to a sequence that mediates expression of said hybrid gene in a cell of interest.

10. A recombinant expression vector comprising a hybrid gene according to claim 9.

11. A recombinant expression vector according to claim 10, wherein said vector is the bovine papilloma virus vector pS258, pS259 or pS299.

12. A recombinant cell comprising the vector of claim 10.

13. A recombinant cell according to claim 12, wherein said cell is selected from the group consisting of the murine cell line C127 and *E coli*.

14. A method of producing a BSSL protein having Bile Salt stimulated Lipase activity comprising:
    (a) growing the recombinant cell according to claim 12 under conditions suitable for expression of said protein; and
    (b) recovering said protein from said cell.

15. The method or claim 14 wherein said recombinant expression vector is the bovine papilloma virus vector pS258, pS259 or pS299.

* * * * *

UNITED STATES PATENT AND TRADEMARK OFFICE
CERTIFICATE OF CORRECTION

PATENT NO. : 5,827,683
DATED : October 27, 1998
INVENTOR(S) : Blackberg et al.

It is certified that error appears in the above-identified patent and that said Letters Patent is hereby corrected as shown below:

Col. 67, line 39 (claim 1, line 1), change "11" to --1--;

Col. 68, line 26 (claim 9, line 2), change "2" to --7--; and

Col. 68, line 37 (claim 14, line 2), change "stimulated" to --Stimulated--.

Signed and Sealed this

Fourteenth Day of September, 1999

Attest:

Q. TODD DICKINSON

*Attesting Officer*    Acting Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 2428 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: mammary gland ( i x ) FEATURE:
        ( A ) NAME/KEY: CDS
        ( B ) LOCATION: 82..2319
        ( D ) OTHER INFORMATION: /product="bile-salt-stimulated lipase"

( i x ) FEATURE:
        ( A ) NAME/KEY: exon
        ( B ) LOCATION: 985..1173

( i x ) FEATURE:
        ( A ) NAME/KEY: exon
        ( B ) LOCATION: 1174..1377

( i x ) FEATURE:
        ( A ) NAME/KEY: exon
        ( B ) LOCATION: 1378..1575

( i x ) FEATURE:
        ( A ) NAME/KEY: exon
        ( B ) LOCATION: 1576..2415

( i x ) FEATURE:
      ( A ) NAME/KEY: mat_peptide
      ( B ) LOCATION: 151..2316

( i x ) FEATURE:
      ( A ) NAME/KEY: polyA_signal
      ( B ) LOCATION: 2397..2402

( i x ) FEATURE:
      ( A ) NAME/KEY: repeat_region
      ( B ) LOCATION: 1756..2283

( i x ) FEATURE:
      ( A ) NAME/KEY: 5'UTR
      ( B ) LOCATION: 1..81

( i x ) FEATURE:
      ( A ) NAME/KEY: repeat_unit
      ( B ) LOCATION: 1756..1788

( i x ) FEATURE:
      ( A ) NAME/KEY: repeat_unit
      ( B ) LOCATION: 1789..1821

( i x ) FEATURE:
      ( A ) NAME/KEY: repeat_unit
      ( B ) LOCATION: 1822..1854

( i x ) FEATURE:
      ( A ) NAME/KEY: repeat_unit
      ( B ) LOCATION: 1855..1887

( i x ) FEATURE:
      ( A ) NAME/KEY: repeat_unit
      ( B ) LOCATION: 1888..1920

( i x ) FEATURE:
      ( A ) NAME/KEY: repeat_unit
      ( B ) LOCATION: 1921..1953

( i x ) FEATURE:
      ( A ) NAME/KEY: repeat_unit
      ( B ) LOCATION: 1954..1986

( i x ) FEATURE:
      ( A ) NAME/KEY: repeat_unit
      ( B ) LOCATION: 1987..2019

( i x ) FEATURE:
      ( A ) NAME/KEY: repeat_unit
      ( B ) LOCATION: 2020..2052

( i x ) FEATURE:
      ( A ) NAME/KEY: repeat_unit
      ( B ) LOCATION: 2053..2085

( i x ) FEATURE:
      ( A ) NAME/KEY: repeat_unit
      ( B ) LOCATION: 2086..2118

( i x ) FEATURE:
      ( A ) NAME/KEY: repeat_unit
      ( B ) LOCATION: 2119..2151

( i x ) FEATURE:
      ( A ) NAME/KEY: repeat_unit
      ( B ) LOCATION: 2152..2184

( i x ) FEATURE:
      ( A ) NAME/KEY: repeat_unit
      ( B ) LOCATION: 2185..2217

( i x ) FEATURE:
      ( A ) NAME/KEY: repeat_unit
      ( B ) LOCATION: 2218..2250

( i x ) FEATURE:
      ( A ) NAME/KEY: repeat_unit
      ( B ) LOCATION: 2251..2283

( x i ) SEQUENCE DESCRIPTION: SEQ ID NO:1:

```
ACCTTCTGTA TCAGTTAAGT GTCAAGATGG AAGGAACAGC AGTCTCAAGA TAATGCAAAG        60

AGTTTATTCA TCCAGAGGCT G ATG CTC ACC ATG GGG CGC CTG CAA CTG GTT        111
                       Met Leu Thr Met Gly Arg Leu Gln Leu Val
                       -23         -20                     -15

GTG TTG GGC CTC ACC TGC TGC TGG GCA GTG GCG AGT GCC GCG AAG CTG        159
Val Leu Gly Leu Thr Cys Cys Trp Ala Val Ala Ser Ala Ala Lys Leu
            -10                 -5                   1

GGC GCC GTG TAC ACA GAA GGT GGG TTC GTG GAA GGC GTC AAT AAG AAG        207
Gly Ala Val Tyr Thr Glu Gly Gly Phe Val Glu Gly Val Asn Lys Lys
        5               10                  15

CTC GGC CTC CTG GGT GAC TCT GTG GAC ATC TTC AAG GGC ATC CCC TTC        255
Leu Gly Leu Leu Gly Asp Ser Val Asp Ile Phe Lys Gly Ile Pro Phe
 20              25                  30                      35

GCA GCT CCC ACC AAG GCC CTG GAA AAT CCT CAG CCA CAT CCT GGC TGG        303
Ala Ala Pro Thr Lys Ala Leu Glu Asn Pro Gln Pro His Pro Gly Trp
             40                  45                      50

CAA GGG ACC CTG AAG GCC AAG AAC TTC AAG AAG AGA TGC CTG CAG GCC        351
Gln Gly Thr Leu Lys Ala Lys Asn Phe Lys Lys Arg Cys Leu Gln Ala
                 55                  60                  65

ACC ATC ACC CAG GAC AGC ACC TAC GGG GAT GAA GAC TGC CTG TAC CTC        399
Thr Ile Thr Gln Asp Ser Thr Tyr Gly Asp Glu Asp Cys Leu Tyr Leu
             70                  75                  80

AAC ATT TGG GTG CCC CAG GGC AGG AAG CAA GTC TCC CGG GAC CTG CCC        447
Asn Ile Trp Val Pro Gln Gly Arg Lys Gln Val Ser Arg Asp Leu Pro
     85                  90                  95

GTT ATG ATC TGG ATC TAT GGA GGC GCC TTC CTC ATG GGG TCC GGC CAT        495
Val Met Ile Trp Ile Tyr Gly Gly Ala Phe Leu Met Gly Ser Gly His
100              105                 110                     115

GGG GCC AAC TTC CTC AAC AAC TAC CTG TAT GAC GGC GAG GAG ATC GCC        543
Gly Ala Asn Phe Leu Asn Asn Tyr Leu Tyr Asp Gly Glu Glu Ile Ala
                 120                 125                 130

ACA CGC GGA AAC GTC ATC GTG GTC ACC TTC AAC TAC CGT GTC GGC CCC        591
Thr Arg Gly Asn Val Ile Val Val Thr Phe Asn Tyr Arg Val Gly Pro
             135                 140                 145

CTT GGG TTC CTC AGC ACT GGG GAC GCC AAT CTG CCA GGT AAC TAT GGC        639
Leu Gly Phe Leu Ser Thr Gly Asp Ala Asn Leu Pro Gly Asn Tyr Gly
         150                 155                 160

CTT CGG GAT CAG CAC ATG GCC ATT GCT TGG GTG AAG AGG AAT ATC GCG        687
Leu Arg Asp Gln His Met Ala Ile Ala Trp Val Lys Arg Asn Ile Ala
 165                 170                 175

GCC TTC GGG GGG GAC CCC AAC AAC ATC ACG CTC TTC GGG GAG TCT GCT        735
Ala Phe Gly Gly Asp Pro Asn Asn Ile Thr Leu Phe Gly Glu Ser Ala
180              185                 190                     195

GGA GGT GCC AGC GTC TCT CTG CAG ACC CTC TCC CCC TAC AAC AAG GGC        783
Gly Gly Ala Ser Val Ser Leu Gln Thr Leu Ser Pro Tyr Asn Lys Gly
                 200                 205                 210

CTC ATC CGG CGA GCC ATC AGC CAG AGC GGC GTG GCC CTG AGT CCC TGG        831
Leu Ile Arg Arg Ala Ile Ser Gln Ser Gly Val Ala Leu Ser Pro Trp
             215                 220                 225

GTC ATC CAG AAA AAC CCA CTC TTC TGG GCC AAA AAG GTG GCT GAG AAG        879
Val Ile Gln Lys Asn Pro Leu Phe Trp Ala Lys Lys Val Ala Glu Lys
         230                 235                 240

GTG GGT TGC CCT GTG GGT GAT GCC GCC AGG ATG GCC CAG TGT CTG AAG        927
Val Gly Cys Pro Val Gly Asp Ala Ala Arg Met Ala Gln Cys Leu Lys
 245                 250                 255

GTT ACT GAT CCC CGA GCC CTG ACG CTG GCC TAT AAG GTG CCG CTG GCA        975
Val Thr Asp Pro Arg Ala Leu Thr Leu Ala Tyr Lys Val Pro Leu Ala
260              265                 270                     275
```

| | | | | | | | | | | | | | | | | |
|---|---|---|---|---|---|---|---|---|---|---|---|---|---|---|---|---|
| GGC | CTG | GAG | TAC | CCC | ATG | CTG | CAC | TAT | GTG | GGC | TTC | GTC | CCT | GTC | ATT | 1023 |
| Gly | Leu | Glu | Tyr | Pro | Met | Leu | His | Tyr | Val | Gly | Phe | Val | Pro | Val | Ile | |
| | | | | 280 | | | | 285 | | | | | 290 | | | |
| GAT | GGA | GAC | TTC | ATC | CCC | GCT | GAC | CCG | ATC | AAC | CTG | TAC | GCC | AAC | GCC | 1071 |
| Asp | Gly | Asp | Phe | Ile | Pro | Ala | Asp | Pro | Ile | Asn | Leu | Tyr | Ala | Asn | Ala | |
| | | 295 | | | | | | 300 | | | | | 305 | | | |
| GCC | GAC | ATC | GAC | TAT | ATA | GCA | GGC | ACC | AAC | AAC | ATG | GAC | GGC | CAC | ATC | 1119 |
| Ala | Asp | Ile | Asp | Tyr | Ile | Ala | Gly | Thr | Asn | Asn | Met | Asp | Gly | His | Ile | |
| | | 310 | | | | | 315 | | | | | 320 | | | | |
| TTC | GCC | AGC | ATC | GAC | ATG | CCT | GCC | ATC | AAC | AAG | GGC | AAC | AAG | AAA | GTC | 1167 |
| Phe | Ala | Ser | Ile | Asp | Met | Pro | Ala | Ile | Asn | Lys | Gly | Asn | Lys | Lys | Val | |
| | | 325 | | | | 330 | | | | 335 | | | | | | |
| ACG | GAG | GAG | GAC | TTC | TAC | AAG | CTG | GTC | AGT | GAG | TTC | ACA | ATC | ACC | AAG | 1215 |
| Thr | Glu | Glu | Asp | Phe | Tyr | Lys | Leu | Val | Ser | Glu | Phe | Thr | Ile | Thr | Lys | |
| 340 | | | | | 345 | | | | | 350 | | | | | 355 | |
| GGG | CTC | AGA | GGC | GCC | AAG | ACG | ACC | TTT | GAT | GTC | TAC | ACC | GAG | TCC | TGG | 1263 |
| Gly | Leu | Arg | Gly | Ala | Lys | Thr | Thr | Phe | Asp | Val | Tyr | Thr | Glu | Ser | Trp | |
| | | | | 360 | | | | | 365 | | | | | 370 | | |
| GCC | CAG | GAC | CCA | TCC | CAG | GAG | AAT | AAG | AAG | AAG | ACT | GTG | GTG | GAC | TTT | 1311 |
| Ala | Gln | Asp | Pro | Ser | Gln | Glu | Asn | Lys | Lys | Lys | Thr | Val | Val | Asp | Phe | |
| | | | 375 | | | | | 380 | | | | | 385 | | | |
| GAG | ACC | GAT | GTC | CTC | TTC | CTG | GTG | CCC | ACC | GAG | ATT | GCC | CTA | GCC | CAG | 1359 |
| Glu | Thr | Asp | Val | Leu | Phe | Leu | Val | Pro | Thr | Glu | Ile | Ala | Leu | Ala | Gln | |
| | | 390 | | | | | 395 | | | | | 400 | | | | |
| CAC | AGA | GCC | AAT | GCC | AAG | AGT | GCC | AAG | ACC | TAC | GCC | TAC | CTG | TTT | TCC | 1407 |
| His | Arg | Ala | Asn | Ala | Lys | Ser | Ala | Lys | Thr | Tyr | Ala | Tyr | Leu | Phe | Ser | |
| | 405 | | | | | 410 | | | | | 415 | | | | | |
| CAT | CCC | TCT | CGG | ATG | CCC | GTC | TAC | CCC | AAA | TGG | GTG | GGG | GCC | GAC | CAT | 1455 |
| His | Pro | Ser | Arg | Met | Pro | Val | Tyr | Pro | Lys | Trp | Val | Gly | Ala | Asp | His | |
| 420 | | | | | 425 | | | | 430 | | | | | 435 | | |
| GCA | GAT | GAC | ATT | CAG | TAC | GTT | TTC | GGG | AAG | CCC | TTC | GCC | ACC | CCC | ACG | 1503 |
| Ala | Asp | Asp | Ile | Gln | Tyr | Val | Phe | Gly | Lys | Pro | Phe | Ala | Thr | Pro | Thr | |
| | | | | 440 | | | | | 445 | | | | | 450 | | |
| GGC | TAC | CGG | CCC | CAA | GAC | AGG | ACA | GTC | TCT | AAG | GCC | ATG | ATC | GCC | TAC | 1551 |
| Gly | Tyr | Arg | Pro | Gln | Asp | Arg | Thr | Val | Ser | Lys | Ala | Met | Ile | Ala | Tyr | |
| | | | 455 | | | | | 460 | | | | | 465 | | | |
| TGG | ACC | AAC | TTT | GCC | AAA | ACA | GGG | GAC | CCC | AAC | ATG | GGC | GAC | TCG | GCT | 1599 |
| Trp | Thr | Asn | Phe | Ala | Lys | Thr | Gly | Asp | Pro | Asn | Met | Gly | Asp | Ser | Ala | |
| | | 470 | | | | | 475 | | | | | 480 | | | | |
| GTG | CCC | ACA | CAC | TGG | GAA | CCC | TAC | ACT | ACG | GAA | AAC | AGC | GGC | TAC | CTG | 1647 |
| Val | Pro | Thr | His | Trp | Glu | Pro | Tyr | Thr | Thr | Glu | Asn | Ser | Gly | Tyr | Leu | |
| | 485 | | | | | 490 | | | | | 495 | | | | | |
| GAG | ATC | ACC | AAG | AAG | ATG | GGC | AGC | AGC | TCC | ATG | AAG | CGG | AGC | CTG | AGA | 1695 |
| Glu | Ile | Thr | Lys | Lys | Met | Gly | Ser | Ser | Ser | Met | Lys | Arg | Ser | Leu | Arg | |
| 500 | | | | | 505 | | | | | 510 | | | | | 515 | |
| ACC | AAC | TTC | CTG | CGC | TAC | TGG | ACC | CTC | ACC | TAT | CTG | GCG | CTG | CCC | ACA | 1743 |
| Thr | Asn | Phe | Leu | Arg | Tyr | Trp | Thr | Leu | Thr | Tyr | Leu | Ala | Leu | Pro | Thr | |
| | | | | 520 | | | | | 525 | | | | | 530 | | |
| GTG | ACC | GAC | CAG | GAG | GCC | ACC | CCT | GTG | CCC | CCC | ACA | GGG | GAC | TCC | GAG | 1791 |
| Val | Thr | Asp | Gln | Glu | Ala | Thr | Pro | Val | Pro | Pro | Thr | Gly | Asp | Ser | Glu | |
| | | | | 535 | | | | | 540 | | | | | 545 | | |
| GCC | ACT | CCC | GTG | CCC | CCC | ACG | GGT | GAC | TCC | GAG | ACC | GCC | CCC | GTG | CCG | 1839 |
| Ala | Thr | Pro | Val | Pro | Pro | Thr | Gly | Asp | Ser | Glu | Thr | Ala | Pro | Val | Pro | |
| | | | 550 | | | | | 555 | | | | | 560 | | | |
| CCC | ACG | GGT | GAC | TCC | GGG | GCC | CCC | CCC | GTG | CCG | CCC | ACG | GGT | GAC | TCC | 1887 |
| Pro | Thr | Gly | Asp | Ser | Gly | Ala | Pro | Pro | Val | Pro | Pro | Thr | Gly | Asp | Ser | |
| | | 565 | | | | | 570 | | | | | 575 | | | | |
| GGG | GCC | CCC | CCC | GTG | CCG | CCC | ACG | GGT | GAC | TCC | GGG | GCC | CCC | CCC | GTG | 1935 |
| Gly | Ala | Pro | Pro | Val | Pro | Pro | Thr | Gly | Asp | Ser | Gly | Ala | Pro | Pro | Val | |
| | 580 | | | | 585 | | | | | 590 | | | | | 595 | |

```
CCG  CCC  ACG  GGT  GAC  TCC  GGG  GCC  CCC  CCC  GTG  CCG  CCC  ACG  GGT  GAC    1983
Pro  Pro  Thr  Gly  Asp  Ser  Gly  Ala  Pro  Pro  Val  Pro  Pro  Thr  Gly  Asp
               600                      605                      610

TCC  GGG  GCC  CCC  CCC  GTG  CCG  CCC  ACG  GGT  GAC  TCC  GGG  GCC  CCC  CCC    2031
Ser  Gly  Ala  Pro  Pro  Val  Pro  Pro  Thr  Gly  Asp  Ser  Gly  Ala  Pro  Pro
               615                      620                      625

GTG  CCG  CCC  ACG  GGT  GAC  TCC  GGC  GCC  CCC  GTG  CCG  CCC  ACG  GGT         2079
Val  Pro  Pro  Thr  Gly  Asp  Ser  Gly  Ala  Pro  Pro  Val  Pro  Pro  Thr  Gly
          630                      635                      640

GAC  GCC  GGG  CCC  CCC  CCC  GTG  CCG  CCC  ACG  GGT  GAC  TCC  GGC  GCC  CCC    2127
Asp  Ala  Gly  Pro  Pro  Pro  Val  Pro  Pro  Thr  Gly  Asp  Ser  Gly  Ala  Pro
          645                      650                      655

CCC  GTG  CCG  CCC  ACG  GGT  GAC  TCC  GGG  GCC  CCC  CCC  GTG  ACC  CCC  ACG    2175
Pro  Val  Pro  Pro  Thr  Gly  Asp  Ser  Gly  Ala  Pro  Pro  Val  Thr  Pro  Thr
660                      665                      670                      675

GGT  GAC  TCC  GAG  ACC  GCC  CCC  GTG  CCG  CCC  ACG  GGT  GAC  TCC  GGG  GCC    2223
Gly  Asp  Ser  Glu  Thr  Ala  Pro  Val  Pro  Pro  Thr  Gly  Asp  Ser  Gly  Ala
               680                      685                      690

CCC  CCT  GTG  CCC  CCC  ACG  GGT  GAC  TCT  GAG  GCT  GCC  CCT  GTG  CCC  CCC    2271
Pro  Pro  Val  Pro  Pro  Thr  Gly  Asp  Ser  Glu  Ala  Ala  Pro  Val  Pro  Pro
          695                      700                      705

ACA  GAT  GAC  TCC  AAG  GAA  GCT  CAG  ATG  CCT  GCA  GTC  ATT
Thr  Asp  Asp  Ser  Lys  Glu  Ala  Gln  Met  Pro  Ala  Val  Ile
          710                      715                      720

AGG  TTT  TAGCGTCCCA            2326
                                                   Arg  Phe

TGAGCCTTGG  TATCAAGAGG  CCACAAGAGT  GGGACCCCAG  GGGCTCCCCT  CCCATCTTGA             2386

GCTCTTCCTG  AATAAAGCCT  CATACCCCTA  AAAAAAAAAA  AA                                 2428
```

( 2 ) INFORMATION FOR SEQ ID NO:2:

( i ) SEQUENCE CHARACTERISTICS:
        ( A ) LENGTH: 745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Thr  Met  Gly  Arg  Leu  Gln  Leu  Val  Val  Leu  Gly  Leu  Thr  Cys
-23            -20                      -15                      -10

Cys  Trp  Ala  Val  Ala  Ser  Ala  Ala  Lys  Leu  Gly  Ala  Val  Tyr  Thr  Glu
          -5                       1                        5

Gly  Gly  Phe  Val  Glu  Gly  Val  Asn  Lys  Lys  Leu  Gly  Leu  Leu  Gly  Asp
10                  15                       20                            25

Ser  Val  Asp  Ile  Phe  Lys  Gly  Ile  Pro  Phe  Ala  Ala  Pro  Thr  Lys  Ala
               30                       35                            40

Leu  Glu  Asn  Pro  Gln  Pro  His  Pro  Gly  Trp  Gln  Gly  Thr  Leu  Lys  Ala
               45                       50                       55

Lys  Asn  Phe  Lys  Lys  Arg  Cys  Leu  Gln  Ala  Thr  Ile  Thr  Gln  Asp  Ser
          60                       65                       70

Thr  Tyr  Gly  Asp  Glu  Asp  Cys  Leu  Tyr  Leu  Asn  Ile  Trp  Val  Pro  Gln
     75                       80                       85

Gly  Arg  Lys  Gln  Val  Ser  Arg  Asp  Leu  Pro  Val  Met  Ile  Trp  Ile  Tyr
90                  95                       100                           105

Gly  Gly  Ala  Phe  Leu  Met  Gly  Ser  Gly  His  Gly  Ala  Asn  Phe  Leu  Asn
                    110                      115                      120
```

```
Asn  Tyr  Leu  Tyr  Asp  Gly  Glu  Glu  Ile  Ala  Thr  Arg  Gly  Asn  Val  Ile
               125                     130                    135

Val  Val  Thr  Phe  Asn  Tyr  Arg  Val  Gly  Pro  Leu  Gly  Phe  Leu  Ser  Thr
               140                     145                    150

Gly  Asp  Ala  Asn  Leu  Pro  Gly  Asn  Tyr  Gly  Leu  Arg  Asp  Gln  His  Met
          155                     160                    165

Ala  Ile  Ala  Trp  Val  Lys  Arg  Asn  Ile  Ala  Ala  Phe  Gly  Gly  Asp  Pro
170                     175                    180                    185

Asn  Asn  Ile  Thr  Leu  Phe  Gly  Glu  Ser  Ala  Gly  Gly  Ala  Ser  Val  Ser
               190                     195                    200

Leu  Gln  Thr  Leu  Ser  Pro  Tyr  Asn  Lys  Gly  Leu  Ile  Arg  Arg  Ala  Ile
               205                     210                    215

Ser  Gln  Ser  Gly  Val  Ala  Leu  Ser  Pro  Trp  Val  Ile  Gln  Lys  Asn  Pro
          220                     225                    230

Leu  Phe  Trp  Ala  Lys  Lys  Val  Ala  Glu  Lys  Val  Gly  Cys  Pro  Val  Gly
          235                     240                    245

Asp  Ala  Ala  Arg  Met  Ala  Gln  Cys  Leu  Lys  Val  Thr  Asp  Pro  Arg  Ala
250                     255                    260                    265

Leu  Thr  Leu  Ala  Tyr  Lys  Val  Pro  Leu  Ala  Gly  Leu  Glu  Tyr  Pro  Met
               270                     275                    280

Leu  His  Tyr  Val  Gly  Phe  Val  Pro  Val  Ile  Asp  Gly  Asp  Phe  Ile  Pro
               285                     290                    295

Ala  Asp  Pro  Ile  Asn  Leu  Tyr  Ala  Asn  Ala  Ala  Asp  Ile  Asp  Tyr  Ile
          300                     305                    310

Ala  Gly  Thr  Asn  Asn  Met  Asp  Gly  His  Ile  Phe  Ala  Ser  Ile  Asp  Met
          315                     320                    325

Pro  Ala  Ile  Asn  Lys  Gly  Asn  Lys  Lys  Val  Thr  Glu  Glu  Asp  Phe  Tyr
330                     335                    340                    345

Lys  Leu  Val  Ser  Glu  Phe  Thr  Ile  Thr  Lys  Gly  Leu  Arg  Gly  Ala  Lys
               350                     355                    360

Thr  Thr  Phe  Asp  Val  Tyr  Thr  Glu  Ser  Trp  Ala  Gln  Asp  Pro  Ser  Gln
               365                     370                    375

Glu  Asn  Lys  Lys  Lys  Thr  Val  Val  Asp  Phe  Glu  Thr  Asp  Val  Leu  Phe
          380                     385                    390

Leu  Val  Pro  Thr  Glu  Ile  Ala  Leu  Ala  Gln  His  Arg  Ala  Asn  Ala  Lys
     395                     400                    405

Ser  Ala  Lys  Thr  Tyr  Ala  Tyr  Leu  Phe  Ser  His  Pro  Ser  Arg  Met  Pro
410                     415                    420                    425

Val  Tyr  Pro  Lys  Trp  Val  Gly  Ala  Asp  His  Ala  Asp  Asp  Ile  Gln  Tyr
               430                     435                    440

Val  Phe  Gly  Lys  Pro  Phe  Ala  Thr  Pro  Thr  Gly  Tyr  Arg  Pro  Gln  Asp
          445                     450                    455

Arg  Thr  Val  Ser  Lys  Ala  Met  Ile  Ala  Tyr  Trp  Thr  Asn  Phe  Ala  Lys
          460                     465                    470

Thr  Gly  Asp  Pro  Asn  Met  Gly  Asp  Ser  Ala  Val  Pro  Thr  His  Trp  Glu
     475                     480                    485

Pro  Tyr  Thr  Thr  Glu  Asn  Ser  Gly  Tyr  Leu  Glu  Ile  Thr  Lys  Lys  Met
490                     495                    500                    505

Gly  Ser  Ser  Ser  Met  Lys  Arg  Ser  Leu  Arg  Thr  Asn  Phe  Leu  Arg  Tyr
               510                     515                    520

Trp  Thr  Leu  Thr  Tyr  Leu  Ala  Leu  Pro  Thr  Val  Thr  Asp  Gln  Glu  Ala
               525                     530                    535

Thr  Pro  Val  Pro  Pro  Thr  Gly  Asp  Ser  Glu  Ala  Thr  Pro  Val  Pro  Pro
          540                     545                    550
```

| Thr | Gly | Asp | Ser | Glu | Thr | Ala | Pro | Val | Pro | Pro | Thr | Gly | Asp | Ser | Gly |
|---|---|---|---|---|---|---|---|---|---|---|---|---|---|---|---|
| | 555 | | | | 560 | | | | | 565 | | | | | |

| Ala | Pro | Pro | Val | Pro | Pro | Thr | Gly | Asp | Ser | Gly | Ala | Pro | Pro | Val | Pro |
|---|---|---|---|---|---|---|---|---|---|---|---|---|---|---|---|
| 570 | | | | | 575 | | | | 580 | | | | | | 585 |

| Pro | Thr | Gly | Asp | Ser | Gly | Ala | Pro | Pro | Val | Pro | Pro | Thr | Gly | Asp | Ser |
|---|---|---|---|---|---|---|---|---|---|---|---|---|---|---|---|
| | | | | 590 | | | | | 595 | | | | | | 600 |

| Gly | Ala | Pro | Pro | Val | Pro | Pro | Thr | Gly | Asp | Ser | Gly | Ala | Pro | Pro | Val |
|---|---|---|---|---|---|---|---|---|---|---|---|---|---|---|---|
| | | | 605 | | | | | 610 | | | | | 615 | | |

| Pro | Pro | Thr | Gly | Asp | Ser | Gly | Ala | Pro | Pro | Val | Pro | Pro | Thr | Gly | Asp |
|---|---|---|---|---|---|---|---|---|---|---|---|---|---|---|---|
| | | 620 | | | | | 625 | | | | | 630 | | | |

| Ser | Gly | Ala | Pro | Pro | Val | Pro | Pro | Thr | Gly | Asp | Ala | Gly | Pro | Pro | Pro |
|---|---|---|---|---|---|---|---|---|---|---|---|---|---|---|---|
| | 635 | | | | 640 | | | | | 645 | | | | | |

| Val | Pro | Pro | Thr | Gly | Asp | Ser | Gly | Ala | Pro | Pro | Val | Pro | Pro | Thr | Gly |
|---|---|---|---|---|---|---|---|---|---|---|---|---|---|---|---|
| 650 | | | | | 655 | | | | | 660 | | | | | 665 |

| Asp | Ser | Gly | Ala | Pro | Pro | Val | Thr | Pro | Thr | Gly | Asp | Ser | Glu | Thr | Ala |
|---|---|---|---|---|---|---|---|---|---|---|---|---|---|---|---|
| | | | | 670 | | | | | 675 | | | | | 680 | |

| Pro | Val | Pro | Pro | Thr | Gly | Asp | Ser | Gly | Ala | Pro | Pro | Val | Pro | Pro | Thr |
|---|---|---|---|---|---|---|---|---|---|---|---|---|---|---|---|
| | | | 685 | | | | | 690 | | | | | 695 | | |

| Gly | Asp | Ser | Glu | Ala | Ala | Pro | Val | Pro | Pro | Thr | Asp | Asp | Ser | Lys | Glu |
|---|---|---|---|---|---|---|---|---|---|---|---|---|---|---|---|
| | | 700 | | | | | 705 | | | | | 710 | | | |

| Ala | Gln | Met | Pro | Ala | Val | Ile | Arg | Phe |
|---|---|---|---|---|---|---|---|---|
| | 715 | | | | | 720 | | |

( 2 ) INFORMATION FOR SEQ ID NO:3:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( x i ) SEQUENCE DESCRIPTION: SEQ ID NO:3:

| Ala | Lys | Leu | Gly | Ala | Val | Tyr | Thr | Glu | Gly | Gly | Phe | Val | Glu | Gly | Val |
|---|---|---|---|---|---|---|---|---|---|---|---|---|---|---|---|
| 1 | | | | 5 | | | | | 10 | | | | | 15 | |

| Asn | Lys | Lys | Leu | Gly | Leu | Leu | Gly | Asp | Ser | Val | Asp | Ile | Phe | Lys | Gly |
|---|---|---|---|---|---|---|---|---|---|---|---|---|---|---|---|
| | | | 20 | | | | | 25 | | | | | 30 | | |

| Ile | Pro | Phe | Ala | Ala | Pro | Thr | Lys | Ala | Leu | Glu | Asn | Pro | Gln | Pro | His |
|---|---|---|---|---|---|---|---|---|---|---|---|---|---|---|---|
| | | 35 | | | | | 40 | | | | | 45 | | | |

| Pro | Gly | Trp | Gln | Gly | Thr | Leu | Lys | Ala | Lys | Asn | Phe | Lys | Lys | Arg | Cys |
|---|---|---|---|---|---|---|---|---|---|---|---|---|---|---|---|
| | 50 | | | | | 55 | | | | | 60 | | | | |

| Leu | Gln | Ala | Thr | Ile | Thr | Gln | Asp | Ser | Thr | Tyr | Gly | Asp | Glu | Asp | Cys |
|---|---|---|---|---|---|---|---|---|---|---|---|---|---|---|---|
| 65 | | | | | 70 | | | | | 75 | | | | | 80 |

| Leu | Tyr | Leu | Asn | Ile | Trp | Val | Pro | Gln | Gly | Arg | Lys | Gln | Val | Ser | Arg |
|---|---|---|---|---|---|---|---|---|---|---|---|---|---|---|---|
| | | | | 85 | | | | | 90 | | | | | 95 | |

| Asp | Leu | Pro | Val | Met | Ile | Trp | Ile | Tyr | Gly | Gly | Ala | Phe | Leu | Met | Gly |
|---|---|---|---|---|---|---|---|---|---|---|---|---|---|---|---|
| | | | 100 | | | | | 105 | | | | | 110 | | |

| Ser | Gly | His | Gly | Ala | Asn | Phe | Leu | Asn | Asn | Tyr | Leu | Tyr | Asp | Gly | Glu |
|---|---|---|---|---|---|---|---|---|---|---|---|---|---|---|---|
| | | 115 | | | | | 120 | | | | | 125 | | | |

| Glu | Ile | Ala | Thr | Arg | Gly | Asn | Val | Ile | Val | Val | Thr | Phe | Asn | Tyr | Arg |
|---|---|---|---|---|---|---|---|---|---|---|---|---|---|---|---|
| | | 130 | | | | | 135 | | | | | 140 | | | |

| Val | Gly | Pro | Leu | Gly | Phe | Leu | Ser | Thr | Gly | Asp | Ala | Asn | Leu | Pro | Gly |
|---|---|---|---|---|---|---|---|---|---|---|---|---|---|---|---|

```
145                    150                    155                    160
Asn  Tyr  Gly  Leu  Arg  Asp  Gln  His  Met  Ala  Ile  Ala  Trp  Val  Lys  Arg
                         165                      170                      175
Asn  Ile  Ala  Ala  Phe  Gly  Gly  Asp  Pro  Asn  Asn  Ile  Thr  Leu  Phe  Gly
               180                      185                      190
Glu  Ser  Ala  Gly  Gly  Ala  Ser  Val  Ser  Leu  Gln  Thr  Leu  Ser  Pro  Tyr
          195                      200                      205
Asn  Lys  Gly  Leu  Ile  Arg  Arg  Ala  Ile  Ser  Gln  Ser  Gly  Val  Ala  Leu
     210                      215                      220
Ser  Pro  Trp  Val  Ile  Gln  Lys  Asn  Pro  Leu  Phe  Trp  Ala  Lys  Lys  Val
225                      230                      235                      240
Ala  Glu  Lys  Val  Gly  Cys  Pro  Val  Gly  Asp  Ala  Ala  Arg  Met  Ala  Gln
                    245                      250                      255
Cys  Leu  Lys  Val  Thr  Asp  Pro  Arg  Ala  Leu  Thr  Leu  Ala  Tyr  Lys  Val
                260                      265                      270
Pro  Leu  Ala  Gly  Leu  Glu  Tyr  Pro  Met  Leu  His  Tyr  Val  Gly  Phe  Val
          275                      280                      285
Pro  Val  Ile  Asp  Gly  Asp  Phe  Ile  Pro  Ala  Asp  Pro  Ile  Asn  Leu  Tyr
          290                      295                      300
Ala  Asn  Ala  Ala  Asp  Ile  Asp  Tyr  Ile  Ala  Gly  Thr  Asn  Asn  Met  Asp
305                      310                      315                      320
Gly  His  Ile  Phe  Ala  Ser  Ile  Asp  Met  Pro  Ala  Ile  Asn  Lys  Gly  Asn
                    325                      330                      335
Lys  Lys  Val  Thr  Glu  Glu  Asp  Phe  Tyr  Lys  Leu  Val  Ser  Glu  Phe  Thr
                340                      345                      350
Ile  Thr  Lys  Gly  Leu  Arg  Gly  Ala  Lys  Thr  Thr  Phe  Asp  Val  Tyr  Thr
          355                      360                      365
Glu  Ser  Trp  Ala  Gln  Asp  Pro  Ser  Gln  Glu  Asn  Lys  Lys  Lys  Thr  Val
     370                      375                      380
Val  Asp  Phe  Glu  Thr  Asp  Val  Leu  Phe  Leu  Val  Pro  Thr  Glu  Ile  Ala
385                      390                      395                      400
Leu  Ala  Gln  His  Arg  Ala  Asn  Ala  Lys  Ser  Ala  Lys  Thr  Tyr  Ala  Tyr
                    405                      410                      415
Leu  Phe  Ser  His  Pro  Ser  Arg  Met  Pro  Val  Tyr  Pro  Lys  Trp  Val  Gly
                420                      425                      430
Ala  Asp  His  Ala  Asp  Asp  Ile  Gln  Tyr  Val  Phe  Gly  Lys  Pro  Phe  Ala
          435                      440                      445
Thr  Pro  Thr  Gly  Tyr  Arg  Pro  Gln  Asp  Arg  Thr  Val  Ser  Lys  Ala  Met
     450                      455                      460
Ile  Ala  Tyr  Trp  Thr  Asn  Phe  Ala  Lys  Thr  Gly  Asp  Pro  Asn  Met  Gly
465                      470                      475                      480
Asp  Ser  Ala  Val  Pro  Thr  His  Trp  Glu  Pro  Tyr  Thr  Thr  Glu  Asn  Ser
                    485                      490                      495
Gly  Tyr  Leu  Glu  Ile  Thr  Lys  Lys  Met  Gly  Ser  Ser  Ser  Met  Lys  Arg
                500                      505                      510
Ser  Leu  Arg  Thr  Asn  Phe  Leu  Arg  Tyr  Trp  Thr  Leu  Thr  Tyr  Leu  Ala
          515                      520                      525
Leu  Pro  Thr  Val  Thr  Asp  Gln  Glu  Ala  Thr  Pro  Val  Pro  Pro  Thr  Gly
     530                      535                      540
Asp  Ser  Glu  Ala  Thr  Pro  Val  Pro  Pro  Thr  Gly  Asp  Ser  Glu  Thr  Ala
545                      550                      555                      560
Pro  Val  Pro  Pro  Thr  Gly  Asp  Ser  Gly  Ala  Pro  Pro  Val  Pro  Pro  Thr
                    565                      570                      575
```

| Gly | Asp | Ser | Gly | Ala | Pro | Pro | Val | Pro | Pro | Thr | Gly | Asp | Ser | Gly | Ala |
| | | | 580 | | | | 585 | | | | | | 590 | | |
| Pro | Pro | Val | Pro | Pro | Thr | Gly | Asp | Ser | Gly | Ala | Pro | Pro | Val | Pro | Pro |
| | | 595 | | | | | 600 | | | | | 605 | | | |
| Thr | Gly | Asp | Ser | Gly | Ala | Pro | Val | Pro | Pro | Thr | Gly | Asp | Ser | Gly |
| | 610 | | | | | 615 | | | | | 620 | | | | |
| Ala | Pro | Pro | Val | Pro | Pro | Thr | Gly | Asp | Ser | Gly | Ala | Pro | Pro | Val | Pro |
| 625 | | | | | 630 | | | | | | 635 | | | | 640 |
| Pro | Thr | Gly | Asp | Ala | Gly | Pro | Pro | Pro | Val | Pro | Pro | Thr | Gly | Asp | Ser |
| | | | | 645 | | | | | 650 | | | | | 655 | |
| Gly | Ala | Pro | Pro | Val | Pro | Pro | Thr | Gly | Asp | Ser | Gly | Ala | Pro | Pro | Val |
| | | | 660 | | | | | 665 | | | | | 670 | | |
| Thr | Pro | Thr | Gly | Asp | Ser | Glu | Thr | Ala | Pro | Val | Pro | Pro | Thr | Gly | Asp |
| | | 675 | | | | | 680 | | | | | 685 | | | |
| Ser | Gly | Ala | Pro | Pro | Val | Pro | Pro | Thr | Gly | Asp | Ser | Glu | Ala | Ala | Pro |
| | 690 | | | | | 695 | | | | | 700 | | | | |
| Val | Pro | Pro | Thr | Asp | Asp | Ser | Lys | Glu | Ala | Gln | Met | Pro | Ala | Val | Ile |
| 705 | | | | 710 | | | | | | 715 | | | | | 720 |
| Arg | Phe | | | | | | | | | | | | | | |

( 2 ) INFORMATION FOR SEQ ID NO:4:

( i ) SEQUENCE CHARACTERISTICS:
        ( A ) LENGTH: 535 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..535
        ( D ) OTHER INFORMATION: /label=Variant_A ( x i ) SEQUENCE DESCRIPTION: SEQ ID NO:4:

| Ala | Lys | Leu | Gly | Ala | Val | Tyr | Thr | Glu | Gly | Gly | Phe | Val | Glu | Gly | Val |
| 1 | | | | 5 | | | | | 10 | | | | | 15 | |
| Asn | Lys | Lys | Leu | Gly | Leu | Leu | Gly | Asp | Ser | Val | Asp | Ile | Phe | Lys | Gly |
| | | | 20 | | | | | 25 | | | | | 30 | | |
| Ile | Pro | Phe | Ala | Ala | Pro | Thr | Lys | Ala | Leu | Glu | Asn | Pro | Gln | Pro | His |
| | | 35 | | | | | 40 | | | | | 45 | | | |
| Pro | Gly | Trp | Gln | Gly | Thr | Leu | Lys | Ala | Lys | Asn | Phe | Lys | Lys | Arg | Cys |
| | 50 | | | | | 55 | | | | | 60 | | | | |
| Leu | Gln | Ala | Thr | Ile | Thr | Gln | Asp | Ser | Thr | Tyr | Gly | Asp | Glu | Asp | Cys |
| 65 | | | | 70 | | | | | 75 | | | | | | 80 |
| Leu | Tyr | Leu | Asn | Ile | Trp | Val | Pro | Gln | Gly | Arg | Lys | Gln | Val | Ser | Arg |
| | | | | 85 | | | | | 90 | | | | | 95 | |
| Asp | Leu | Pro | Val | Met | Ile | Trp | Ile | Tyr | Gly | Gly | Ala | Phe | Leu | Met | Gly |
| | | | 100 | | | | | 105 | | | | | 110 | | |
| Ser | Gly | His | Gly | Ala | Asn | Phe | Leu | Asn | Asn | Tyr | Leu | Tyr | Asp | Gly | Glu |
| | | 115 | | | | | 120 | | | | | 125 | | | |
| Glu | Ile | Ala | Thr | Arg | Gly | Asn | Val | Ile | Val | Val | Thr | Phe | Asn | Tyr | Arg |
| | | 130 | | | | | 135 | | | | | 140 | | | |
| Val | Gly | Pro | Leu | Gly | Phe | Leu | Ser | Thr | Gly | Asp | Ala | Asn | Leu | Pro | Gly |

-continued

```
        145                      150                      155                      160
Asn  Tyr  Gly  Leu  Arg  Asp  Gln  His  Met  Ala  Ile  Ala  Trp  Val  Lys  Arg
                    165                      170                      175

Asn  Ile  Ala  Ala  Phe  Gly  Gly  Asp  Pro  Asn  Asn  Ile  Thr  Leu  Phe  Gly
               180                      185                      190

Glu  Ser  Ala  Gly  Gly  Ala  Ser  Val  Ser  Leu  Gln  Thr  Leu  Ser  Pro  Tyr
          195                      200                      205

Asn  Lys  Gly  Leu  Ile  Arg  Arg  Ala  Ile  Ser  Gln  Ser  Gly  Val  Ala  Leu
     210                      215                      220

Ser  Pro  Trp  Val  Ile  Gln  Lys  Asn  Pro  Leu  Phe  Trp  Ala  Lys  Lys  Val
225                      230                      235                      240

Ala  Glu  Lys  Val  Gly  Cys  Pro  Val  Gly  Asp  Ala  Ala  Arg  Met  Ala  Gln
                    245                      250                      255

Cys  Leu  Lys  Val  Thr  Asp  Pro  Arg  Ala  Leu  Thr  Leu  Ala  Tyr  Lys  Val
               260                      265                      270

Pro  Leu  Ala  Gly  Leu  Glu  Tyr  Pro  Met  Leu  His  Tyr  Val  Gly  Phe  Val
          275                      280                      285

Pro  Val  Ile  Asp  Gly  Asp  Phe  Ile  Pro  Ala  Asp  Pro  Ile  Asn  Leu  Tyr
     290                      295                      300

Ala  Asn  Ala  Ala  Asp  Ile  Asp  Tyr  Ile  Ala  Gly  Thr  Asn  Asn  Met  Asp
305                      310                      315                      320

Gly  His  Ile  Phe  Ala  Ser  Ile  Asp  Met  Pro  Ala  Ile  Asn  Lys  Gly  Asn
                    325                      330                      335

Lys  Lys  Val  Thr  Glu  Glu  Asp  Phe  Tyr  Lys  Leu  Val  Ser  Glu  Phe  Thr
               340                      345                      350

Ile  Thr  Lys  Gly  Leu  Arg  Gly  Ala  Lys  Thr  Thr  Phe  Asp  Val  Tyr  Thr
          355                      360                      365

Glu  Ser  Trp  Ala  Gln  Asp  Pro  Ser  Gln  Glu  Asn  Lys  Lys  Lys  Thr  Val
     370                      375                      380

Val  Asp  Phe  Glu  Thr  Asp  Val  Leu  Phe  Leu  Val  Pro  Thr  Glu  Ile  Ala
385                      390                      395                      400

Leu  Ala  Gln  His  Arg  Ala  Asn  Ala  Lys  Ser  Ala  Lys  Thr  Tyr  Ala  Tyr
                    405                      410                      415

Leu  Phe  Ser  His  Pro  Ser  Arg  Met  Pro  Val  Tyr  Pro  Lys  Trp  Val  Gly
               420                      425                      430

Ala  Asp  His  Ala  Asp  Asp  Ile  Gln  Tyr  Val  Phe  Gly  Lys  Pro  Phe  Ala
          435                      440                      445

Thr  Pro  Thr  Gly  Tyr  Arg  Pro  Gln  Asp  Arg  Thr  Val  Ser  Lys  Ala  Met
     450                      455                      460

Ile  Ala  Tyr  Trp  Thr  Asn  Phe  Ala  Lys  Thr  Gly  Asp  Pro  Asn  Met  Gly
465                      470                      475                      480

Asp  Ser  Ala  Val  Pro  Thr  His  Trp  Glu  Pro  Tyr  Thr  Thr  Glu  Asn  Ser
                    485                      490                      495

Gly  Tyr  Leu  Glu  Ile  Thr  Lys  Lys  Met  Gly  Ser  Ser  Ser  Met  Lys  Arg
               500                      505                      510

Ser  Leu  Arg  Thr  Asn  Phe  Leu  Arg  Tyr  Trp  Thr  Leu  Thr  Tyr  Leu  Ala
          515                      520                      525

Leu  Pro  Thr  Val  Thr  Asp  Gln
     530                      535
```

( 2 ) INFORMATION FOR SEQ ID NO:5:

( i ) SEQUENCE CHARACTERISTICS:
        ( A ) LENGTH: 546 amino acids
        ( B ) TYPE: amino acid (D) TOPOLOGY: linear (ii) MOLECULE TYPE: protein (iii) HYPOTHETICAL: NO (vi) ORIGINAL SOURCE:
    (A) ORGANISM: Homo sapiens
    (F) TISSUE TYPE: Mammary gland (ix) FEATURE:
    (A) NAME/KEY: Peptide
    (B) LOCATION: 1..546
    (D) OTHER INFORMATION: /label=Variant_B (xi) SEQUENCE DESCRIPTION: SEQ ID NO:5:

```
Ala Lys Leu Gly Ala Val Tyr Thr Glu Gly Gly Phe Val Glu Gly Val
 1               5                  10                  15

Asn Lys Lys Leu Gly Leu Leu Gly Asp Ser Val Asp Ile Phe Lys Gly
            20                  25                  30

Ile Pro Phe Ala Ala Pro Thr Lys Ala Leu Glu Asn Pro Gln Pro His
             35                  40                  45

Pro Gly Trp Gln Gly Thr Leu Lys Ala Lys Asn Phe Lys Lys Arg Cys
         50                  55                  60

Leu Gln Ala Thr Ile Thr Gln Asp Ser Thr Tyr Gly Asp Glu Asp Cys
 65                  70                  75                  80

Leu Tyr Leu Asn Ile Trp Val Pro Gln Gly Arg Lys Gln Val Ser Arg
                 85                  90                  95

Asp Leu Pro Val Met Ile Trp Ile Tyr Gly Gly Ala Phe Leu Met Gly
             100                 105                 110

Ser Gly His Gly Ala Asn Phe Leu Asn Asn Tyr Leu Tyr Asp Gly Glu
         115                 120                 125

Glu Ile Ala Thr Arg Gly Asn Val Ile Val Val Thr Phe Asn Tyr Arg
130                 135                 140

Val Gly Pro Leu Gly Phe Leu Ser Thr Gly Asp Ala Asn Leu Pro Gly
145                 150                 155                 160

Asn Tyr Gly Leu Arg Asp Gln His Met Ala Ile Ala Trp Val Lys Arg
                 165                 170                 175

Asn Ile Ala Ala Phe Gly Gly Asp Pro Asn Asn Ile Thr Leu Phe Gly
             180                 185                 190

Glu Ser Ala Gly Gly Ala Ser Val Ser Leu Gln Thr Leu Ser Pro Tyr
         195                 200                 205

Asn Lys Gly Leu Ile Arg Arg Ala Ile Ser Gln Ser Gly Val Ala Leu
    210                 215                 220

Ser Pro Trp Val Ile Gln Lys Asn Pro Leu Phe Trp Ala Lys Lys Val
225                 230                 235                 240

Ala Glu Lys Val Gly Cys Pro Val Gly Asp Ala Ala Arg Met Ala Gln
                 245                 250                 255

Cys Leu Lys Val Thr Asp Pro Arg Ala Leu Thr Leu Ala Tyr Lys Val
             260                 265                 270

Pro Leu Ala Gly Leu Glu Tyr Pro Met Leu His Tyr Val Gly Phe Val
         275                 280                 285

Pro Val Ile Asp Gly Asp Phe Ile Pro Ala Asp Pro Ile Asn Leu Tyr
    290                 295                 300

Ala Asn Ala Ala Asp Ile Asp Tyr Ile Ala Gly Thr Asn Asn Met Asp
305                 310                 315                 320

Gly His Ile Phe Ala Ser Ile Asp Met Pro Ala Ile Asn Lys Gly Asn
                 325                 330                 335
```

```
Lys  Lys  Val  Thr  Glu  Glu  Asp  Phe  Tyr  Lys  Leu  Val  Ser  Glu  Phe  Thr
               340                      345                     350

Ile  Thr  Lys  Gly  Leu  Arg  Gly  Ala  Lys  Thr  Thr  Phe  Asp  Val  Tyr  Thr
               355                      360                     365

Glu  Ser  Trp  Ala  Gln  Asp  Ser  Gln  Glu  Asn  Lys  Lys  Thr  Val
     370                      375                     380

Val  Asp  Phe  Glu  Thr  Asp  Val  Leu  Phe  Leu  Val  Pro  Thr  Glu  Ile  Ala
385                           390                     395                     400

Leu  Ala  Gln  His  Arg  Ala  Asn  Ala  Lys  Ser  Ala  Lys  Thr  Tyr  Ala  Tyr
                    405                      410                     415

Leu  Phe  Ser  His  Pro  Ser  Arg  Met  Pro  Val  Tyr  Pro  Lys  Trp  Val  Gly
                    420                      425                     430

Ala  Asp  His  Ala  Asp  Asp  Ile  Gln  Tyr  Val  Phe  Gly  Lys  Pro  Phe  Ala
               435                      440                     445

Thr  Pro  Thr  Gly  Tyr  Arg  Pro  Gln  Asp  Arg  Thr  Val  Ser  Lys  Ala  Met
     450                      455                     460

Ile  Ala  Tyr  Trp  Thr  Asn  Phe  Ala  Lys  Thr  Gly  Asp  Pro  Asn  Met  Gly
465                      470                     475                     480

Asp  Ser  Ala  Val  Pro  Thr  His  Trp  Glu  Pro  Tyr  Thr  Thr  Glu  Asn  Ser
               485                      490                     495

Gly  Tyr  Leu  Glu  Ile  Thr  Lys  Lys  Met  Gly  Ser  Ser  Ser  Met  Lys  Arg
               500                      505                     510

Ser  Leu  Arg  Thr  Asn  Phe  Leu  Arg  Tyr  Trp  Thr  Leu  Thr  Tyr  Leu  Ala
               515                      520                     525

Leu  Pro  Thr  Val  Thr  Asp  Gln  Lys  Glu  Ala  Gln  Met  Pro  Ala  Val  Ile
     530                      535                     540

Arg  Phe
545
```

( 2 ) INFORMATION FOR SEQ ID NO:6:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens
        ( F ) TISSUE TYPE: Mammary gland ( i x ) FEATURE:
        ( A ) NAME/KEY: Peptide
        ( B ) LOCATION: 1..568
        ( D ) OTHER INFORMATION: /label=Variant_C ( x i ) SEQUENCE DESCRIPTION: SEQ ID NO:6:

```
Ala  Lys  Leu  Gly  Ala  Val  Tyr  Thr  Glu  Gly  Gly  Phe  Val  Glu  Gly  Val
1                   5                        10                      15

Asn  Lys  Lys  Leu  Gly  Leu  Leu  Gly  Asp  Ser  Val  Asp  Ile  Phe  Lys  Gly
               20                       25                      30

Ile  Pro  Phe  Ala  Ala  Pro  Thr  Lys  Ala  Leu  Glu  Asn  Pro  Gln  Pro  His
               35                       40                      45

Pro  Gly  Trp  Gln  Gly  Thr  Leu  Lys  Ala  Lys  Asn  Phe  Lys  Lys  Arg  Cys
     50                       55                      60

Leu  Gln  Ala  Thr  Ile  Thr  Gln  Asp  Ser  Thr  Tyr  Gly  Asp  Glu  Asp  Cys
65                       70                      75                      80
```

-continued

|     |     |     |     |     |     |     |     |     |     |     |     |     |     |     |
|-----|-----|-----|-----|-----|-----|-----|-----|-----|-----|-----|-----|-----|-----|-----|
| Leu | Tyr | Leu | Asn | Ile | Trp | Val | Pro | Gln | Gly | Arg | Lys | Gln | Val | Ser | Arg |
|     |     |     |     | 85  |     |     |     |     | 90  |     |     |     |     | 95  |
| Asp | Leu | Pro | Val | Met | Ile | Trp | Ile | Tyr | Gly | Gly | Ala | Phe | Leu | Met | Gly |
|     |     |     | 100 |     |     |     | 105 |     |     |     |     | 110 |     |     |
| Ser | Gly | His | Gly | Ala | Asn | Phe | Leu | Asn | Asn | Tyr | Leu | Tyr | Asp | Gly | Glu |
|     |     | 115 |     |     |     |     | 120 |     |     |     |     | 125 |     |     |
| Glu | Ile | Ala | Thr | Arg | Gly | Asn | Val | Ile | Val | Thr | Phe | Asn | Tyr | Arg |
|     | 130 |     |     |     |     | 135 |     |     |     | 140 |     |     |     |     |
| Val | Gly | Pro | Leu | Gly | Phe | Leu | Ser | Thr | Gly | Asp | Ala | Asn | Leu | Pro | Gly |
| 145 |     |     |     | 150 |     |     |     |     | 155 |     |     |     |     | 160 |
| Asn | Tyr | Gly | Leu | Arg | Asp | Gln | His | Met | Ala | Ile | Ala | Trp | Val | Lys | Arg |
|     |     |     |     | 165 |     |     |     | 170 |     |     |     |     | 175 |     |
| Asn | Ile | Ala | Ala | Phe | Gly | Gly | Asp | Pro | Asn | Asn | Ile | Thr | Leu | Phe | Gly |
|     |     |     | 180 |     |     |     | 185 |     |     |     |     | 190 |     |     |
| Glu | Ser | Ala | Gly | Gly | Ala | Ser | Val | Ser | Leu | Gln | Thr | Leu | Ser | Pro | Tyr |
|     |     | 195 |     |     |     |     | 200 |     |     |     |     | 205 |     |     |
| Asn | Lys | Gly | Leu | Ile | Arg | Arg | Ala | Ile | Ser | Gln | Ser | Gly | Val | Ala | Leu |
|     | 210 |     |     |     |     | 215 |     |     |     |     | 220 |     |     |     |
| Ser | Pro | Trp | Val | Ile | Gln | Lys | Asn | Pro | Leu | Phe | Trp | Ala | Lys | Lys | Val |
| 225 |     |     |     |     | 230 |     |     |     |     | 235 |     |     |     |     | 240 |
| Ala | Glu | Lys | Val | Gly | Cys | Pro | Val | Gly | Asp | Ala | Ala | Arg | Met | Ala | Gln |
|     |     |     |     | 245 |     |     |     |     | 250 |     |     |     | 255 |     |
| Cys | Leu | Lys | Val | Thr | Asp | Pro | Arg | Ala | Leu | Thr | Leu | Ala | Tyr | Lys | Val |
|     |     |     | 260 |     |     |     |     | 265 |     |     |     | 270 |     |     |
| Pro | Leu | Ala | Gly | Leu | Glu | Tyr | Pro | Met | Leu | His | Tyr | Val | Gly | Phe | Val |
|     |     | 275 |     |     |     |     | 280 |     |     |     | 285 |     |     |     |
| Pro | Val | Ile | Asp | Gly | Asp | Phe | Ile | Pro | Ala | Asp | Pro | Ile | Asn | Leu | Tyr |
|     | 290 |     |     |     |     | 295 |     |     |     |     | 300 |     |     |     |
| Ala | Asn | Ala | Ala | Asp | Ile | Asp | Tyr | Ile | Ala | Gly | Thr | Asn | Asn | Met | Asp |
| 305 |     |     |     |     | 310 |     |     |     |     | 315 |     |     |     |     | 320 |
| Gly | His | Ile | Phe | Ala | Ser | Ile | Asp | Met | Pro | Ala | Ile | Asn | Lys | Gly | Asn |
|     |     |     |     | 325 |     |     |     |     | 330 |     |     |     |     | 335 |
| Lys | Lys | Val | Thr | Glu | Glu | Asp | Phe | Tyr | Lys | Leu | Val | Ser | Glu | Phe | Thr |
|     |     |     | 340 |     |     |     |     | 345 |     |     |     |     | 350 |     |
| Ile | Thr | Lys | Gly | Leu | Arg | Gly | Ala | Lys | Thr | Thr | Phe | Asp | Val | Tyr | Thr |
|     |     | 355 |     |     |     |     | 360 |     |     |     |     | 365 |     |     |
| Glu | Ser | Trp | Ala | Gln | Asp | Pro | Ser | Gln | Glu | Asn | Lys | Lys | Lys | Thr | Val |
|     | 370 |     |     |     |     | 375 |     |     |     |     | 380 |     |     |     |
| Val | Asp | Phe | Glu | Thr | Asp | Val | Leu | Phe | Leu | Val | Pro | Thr | Glu | Ile | Ala |
| 385 |     |     |     |     | 390 |     |     |     |     | 395 |     |     |     |     | 400 |
| Leu | Ala | Gln | His | Arg | Ala | Asn | Ala | Lys | Ser | Ala | Lys | Thr | Tyr | Ala | Tyr |
|     |     |     |     | 405 |     |     |     |     | 410 |     |     |     | 415 |     |
| Leu | Phe | Ser | His | Pro | Ser | Arg | Met | Pro | Val | Tyr | Pro | Lys | Trp | Val | Gly |
|     |     |     | 420 |     |     |     |     | 425 |     |     |     | 430 |     |     |
| Ala | Asp | His | Ala | Asp | Asp | Ile | Gln | Tyr | Val | Phe | Gly | Lys | Pro | Phe | Ala |
|     |     | 435 |     |     |     |     | 440 |     |     |     | 445 |     |     |     |
| Thr | Pro | Thr | Gly | Tyr | Arg | Pro | Gln | Asp | Arg | Thr | Val | Ser | Lys | Ala | Met |
|     | 450 |     |     |     |     | 455 |     |     |     | 460 |     |     |     |     |
| Ile | Ala | Tyr | Trp | Thr | Asn | Phe | Ala | Lys | Thr | Gly | Asp | Pro | Asn | Met | Gly |
| 465 |     |     |     |     | 470 |     |     |     |     | 475 |     |     |     |     | 480 |
| Asp | Ser | Ala | Val | Pro | Thr | His | Trp | Glu | Pro | Tyr | Thr | Thr | Glu | Asn | Ser |
|     |     |     |     | 485 |     |     |     |     | 490 |     |     |     | 495 |     |
| Gly | Tyr | Leu | Glu | Ile | Thr | Lys | Lys | Met | Gly | Ser | Ser | Ser | Met | Lys | Arg |
|     |     |     | 500 |     |     |     |     | 505 |     |     |     | 510 |     |     |

| | | | | | | | | | | | | | | |
|---|---|---|---|---|---|---|---|---|---|---|---|---|---|---|
|Ser|Leu|Arg<br>515|Thr|Asn|Phe|Leu|Arg<br>520|Tyr|Trp|Thr|Leu<br>525|Thr|Tyr|Leu|Ala|
|Leu|Pro<br>530|Thr|Val|Thr|Asp|Gln<br>535|Ala|Pro|Pro|Val<br>540|Pro|Pro|Thr|Gly|
|Asp|Ser|Gly|Ala|Pro|Pro<br>550|Val|Pro|Pro|Thr|Gly<br>555|Asp|Ser|Lys|Glu|Ala<br>560|
|Gln|Met|Pro|Ala|Val<br>565|Ile|Arg|Phe|

(2) INFORMATION FOR SEQ ID NO:7:

(i) SEQUENCE CHARACTERISTICS:
        (A) LENGTH: 722 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Homo sapiens
        (F) TISSUE TYPE: Mammary gland (ix) FEATURE:
        (A) NAME/KEY: Peptide
        (B) LOCATION: 1..722
        (D) OTHER INFORMATION: /label=Variant_N (xi) SEQUENCE DESCRIPTION: SEQ ID NO:7:

| | | | | | | | | | | | | | | |
|---|---|---|---|---|---|---|---|---|---|---|---|---|---|---|
|Ala<br>1|Lys|Leu|Gly|Ala<br>5|Val|Tyr|Thr|Glu|Gly<br>10|Gly|Phe|Val|Glu|Gly<br>15|Val|
|Asn|Lys|Lys|Leu<br>20|Gly|Leu|Leu|Gly|Asp<br>25|Ser|Val|Asp|Ile|Phe<br>30|Lys|Gly|
|Ile|Pro|Phe<br>35|Ala|Ala|Pro|Thr|Lys<br>40|Ala|Leu|Glu|Asn|Pro<br>45|Gln|Pro|His|
|Pro|Gly<br>50|Trp|Gln|Gly|Thr|Leu<br>55|Lys|Ala|Lys|Asn|Phe<br>60|Lys|Lys|Arg|Cys|
|Leu<br>65|Gln|Ala|Thr|Ile|Thr<br>70|Gln|Asp|Ser|Thr|Tyr<br>75|Gly|Asp|Glu|Asp|Cys<br>80|
|Leu|Tyr|Leu|Asn|Ile<br>85|Trp|Val|Pro|Gln|Gly<br>90|Arg|Lys|Gln|Val|Ser<br>95|Arg|
|Asp|Leu|Pro|Val<br>100|Met|Ile|Trp|Ile|Tyr<br>105|Gly|Gly|Ala|Phe|Leu<br>110|Met|Gly|
|Ser|Gly|His<br>115|Gly|Ala|Asn|Phe|Leu<br>120|Asn|Asn|Tyr|Leu|Tyr<br>125|Asp|Gly|Glu|
|Glu|Ile<br>130|Ala|Thr|Arg|Gly|Asn<br>135|Val|Ile|Val|Val|Thr<br>140|Phe|Asn|Tyr|Arg|
|Val<br>145|Gly|Pro|Leu|Gly|Phe<br>150|Leu|Ser|Thr|Gly|Asp<br>155|Ala|Asn|Leu|Pro|Gly<br>160|
|Asn|Tyr|Gly|Leu|Arg<br>165|Asp|Gln|His|Met|Ala<br>170|Ile|Ala|Trp|Val|Lys<br>175|Arg|
|Asn|Ile|Ala|Ala<br>180|Phe|Gly|Gly|Asp|Pro<br>185|Asn|Gln|Ile|Thr|Leu<br>190|Phe|Gly|
|Glu|Ser|Ala<br>195|Gly|Gly|Ala|Ser|Val<br>200|Ser|Leu|Gln|Thr|Leu<br>205|Ser|Pro|Tyr|
|Asn|Lys|Gly<br>210|Leu|Ile|Arg|Arg|Ala<br>215|Ile|Ser|Gln|Ser|Gly<br>220|Val|Ala|Leu|
|Ser<br>225|Pro|Trp|Val|Ile|Gln<br>230|Lys|Asn|Pro|Leu|Phe<br>235|Trp|Ala|Lys|Lys|Val<br>240|

-continued

```
Ala  Glu  Lys  Val  Gly  Cys  Pro  Val  Gly  Asp  Ala  Ala  Arg  Met  Ala  Gln
               245                      250                      255

Cys  Leu  Lys  Val  Thr  Asp  Pro  Arg  Ala  Leu  Thr  Leu  Ala  Tyr  Lys  Val
               260                      265                      270

Pro  Leu  Ala  Gly  Leu  Glu  Tyr  Pro  Met  Leu  His  Tyr  Val  Gly  Phe  Val
               275                      280                      285

Pro  Val  Ile  Asp  Gly  Asp  Phe  Ile  Pro  Ala  Asp  Pro  Ile  Asn  Leu  Tyr
               290                      295                      300

Ala  Asn  Ala  Ala  Asp  Ile  Asp  Tyr  Ile  Ala  Gly  Thr  Asn  Asn  Met  Asp
305                      310                      315                      320

Gly  His  Ile  Phe  Ala  Ser  Ile  Asp  Met  Pro  Ala  Ile  Asn  Lys  Gly  Asn
               325                      330                      335

Lys  Lys  Val  Thr  Glu  Glu  Asp  Phe  Tyr  Lys  Leu  Val  Ser  Glu  Phe  Thr
               340                      345                      350

Ile  Thr  Lys  Gly  Leu  Arg  Gly  Ala  Lys  Thr  Thr  Phe  Asp  Val  Tyr  Thr
               355                      360                      365

Glu  Ser  Trp  Ala  Gln  Asp  Pro  Ser  Gln  Glu  Asn  Lys  Lys  Lys  Thr  Val
               370                      375                      380

Val  Asp  Phe  Glu  Thr  Asp  Val  Leu  Phe  Leu  Val  Pro  Thr  Glu  Ile  Ala
385                      390                      395                      400

Leu  Ala  Gln  His  Arg  Ala  Asn  Ala  Lys  Ser  Ala  Lys  Thr  Tyr  Ala  Tyr
               405                      410                      415

Leu  Phe  Ser  His  Pro  Ser  Arg  Met  Pro  Val  Tyr  Pro  Lys  Trp  Val  Gly
               420                      425                      430

Ala  Asp  His  Ala  Asp  Asp  Ile  Gln  Tyr  Val  Phe  Gly  Lys  Pro  Phe  Ala
               435                      440                      445

Thr  Pro  Thr  Gly  Tyr  Arg  Pro  Gln  Asp  Arg  Thr  Val  Ser  Lys  Ala  Met
     450                      455                      460

Ile  Ala  Tyr  Trp  Thr  Asn  Phe  Ala  Lys  Thr  Gly  Asp  Pro  Asn  Met  Gly
465                      470                      475                      480

Asp  Ser  Ala  Val  Pro  Thr  His  Trp  Glu  Pro  Tyr  Thr  Thr  Glu  Asn  Ser
               485                      490                      495

Gly  Tyr  Leu  Glu  Ile  Thr  Lys  Lys  Met  Gly  Ser  Ser  Ser  Met  Lys  Arg
               500                      505                      510

Ser  Leu  Arg  Thr  Asn  Phe  Leu  Arg  Tyr  Trp  Thr  Leu  Thr  Tyr  Leu  Ala
               515                      520                      525

Leu  Pro  Thr  Val  Thr  Asp  Gln  Glu  Ala  Thr  Pro  Val  Pro  Pro  Thr  Gly
     530                      535                      540

Asp  Ser  Glu  Ala  Thr  Pro  Val  Pro  Pro  Thr  Gly  Asp  Ser  Glu  Thr  Ala
545                      550                      555                      560

Pro  Val  Pro  Pro  Thr  Gly  Asp  Ser  Gly  Ala  Pro  Pro  Val  Pro  Pro  Thr
               565                      570                      575

Gly  Asp  Ser  Gly  Ala  Pro  Pro  Val  Pro  Pro  Thr  Gly  Asp  Ser  Gly  Ala
               580                      585                      590

Pro  Pro  Val  Pro  Pro  Thr  Gly  Asp  Ser  Gly  Ala  Pro  Pro  Val  Pro  Pro
               595                      600                      605

Thr  Gly  Asp  Ser  Gly  Ala  Pro  Pro  Val  Pro  Pro  Thr  Gly  Asp  Ser  Gly
     610                      615                      620

Ala  Pro  Pro  Val  Pro  Pro  Thr  Gly  Asp  Ser  Gly  Ala  Pro  Pro  Val  Pro
625                      630                      635                      640

Pro  Thr  Gly  Asp  Ala  Gly  Pro  Pro  Val  Pro  Pro  Thr  Gly  Asp  Ser
               645                      650                      655

Gly  Ala  Pro  Pro  Val  Pro  Pro  Thr  Gly  Asp  Ser  Gly  Ala  Pro  Pro  Val
```

```
                              660                    665                        670
        Thr   Pro   Thr   Gly   Asp   Ser   Glu   Thr   Ala   Pro   Val   Pro   Pro   Thr   Gly   Asp
                    675                          680                      685
        Ser   Gly   Ala   Pro   Pro   Val   Pro   Pro   Thr   Gly   Asp   Ser   Glu   Ala   Ala   Pro
              690                          695                      700
        Val   Pro   Pro   Thr   Asp   Asp   Ser   Lys   Glu   Ala   Gln   Met   Pro   Ala   Val   Ile
        705                          710                      715                              720
        Arg   Phe
```

( 2 ) INFORMATION FOR SEQ ID NO:8:

( i ) SEQUENCE CHARACTERISTICS:
        ( A ) LENGTH: 2184 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: mammary gland ( i x ) FEATURE:
        ( A ) NAME/KEY: CDS
        ( B ) LOCATION: 82..2088
        ( D ) OTHER INFORMATION: /label=Variant_T ( i x ) FEATURE:
        ( A ) NAME/KEY: mat_peptide
        ( B ) LOCATION: 151..2085

( i x ) FEATURE:
        ( A ) NAME/KEY: repeat_region
        ( B ) LOCATION: 1756..2052

( i x ) FEATURE:
        ( A ) NAME/KEY: repeat_unit
        ( B ) LOCATION: 1756..1788

( i x ) FEATURE:
        ( A ) NAME/KEY: repeat_unit
        ( B ) LOCATION: 1789..1821

( i x ) FEATURE:
        ( A ) NAME/KEY: repeat_unit
        ( B ) LOCATION: 1822..1854

( i x ) FEATURE:
        ( A ) NAME/KEY: repeat_unit
        ( B ) LOCATION: 1855..1887

( i x ) FEATURE:
        ( A ) NAME/KEY: repeat_unit
        ( B ) LOCATION: 1888..1920

( i x ) FEATURE:
        ( A ) NAME/KEY: repeat_unit
        ( B ) LOCATION: 1921..1953

( i x ) FEATURE:
        ( A ) NAME/KEY: repeat_unit
        ( B ) LOCATION: 1954..1986

( i x ) FEATURE:
        ( A ) NAME/KEY: repeat_unit
        ( B ) LOCATION: 1987..2019

( i x ) FEATURE:
        ( A ) NAME/KEY: repeat_unit
        ( B ) LOCATION: 2020..2052

(xi) SEQUENCE DESCRIPTION: SEQ ID NO:8:

```
ACCTTCTGTA TCAGTTAAGT GTCAAGATGG AAGGAACAGC AGTCTCAAGA TAATGCAAAG            60

AGTTTATTCA TCCAGAGGCT G ATG CTC ACC ATG GGG CGC CTG CAA CTG GTT           111
                       Met Leu Thr Met Gly Arg Leu Gln Leu Val
                       -23         -20                     -15

GTG TTG GGC CTC ACC TGC TGC TGG GCA GTG GCG AGT GCC GCG AAG CTG           159
Val Leu Gly Leu Thr Cys Cys Trp Ala Val Ala Ser Ala Ala Lys Leu
            -10                  -5                       1

GGC GCC GTG TAC ACA GAA GGT GGG TTC GTG GAA GGC GTC AAT AAG AAG           207
Gly Ala Val Tyr Thr Glu Gly Gly Phe Val Glu Gly Val Asn Lys Lys
         5               10                  15

CTC GGC CTC CTG GGT GAC TCT GTG GAC ATC TTC AAG GGC ATC CCC TTC           255
Leu Gly Leu Leu Gly Asp Ser Val Asp Ile Phe Lys Gly Ile Pro Phe
 20              25                  30                      35

GCA GCT CCC ACC AAG GCC CTG GAA AAT CCT CAG CCA CAT CCT GGC TGG           303
Ala Ala Pro Thr Lys Ala Leu Glu Asn Pro Gln Pro His Pro Gly Trp
                 40                  45                      50

CAA GGG ACC CTG AAG GCC AAG AAC TTC AAG AAG AGA TGC CTG CAG GCC           351
Gln Gly Thr Leu Lys Ala Lys Asn Phe Lys Lys Arg Cys Leu Gln Ala
             55                  60                  65

ACC ATC ACC CAG GAC AGC ACC TAC GGG GAT GAA GAC TGC CTG TAC CTC           399
Thr Ile Thr Gln Asp Ser Thr Tyr Gly Asp Glu Asp Cys Leu Tyr Leu
         70                  75                  80

AAC ATT TGG GTG CCC CAG GGC AGG AAG CAA GTC TCC CGG GAC CTG CCC           447
Asn Ile Trp Val Pro Gln Gly Arg Lys Gln Val Ser Arg Asp Leu Pro
 85                  90                  95

GTT ATG ATC TGG ATC TAT GGA GGC GCC TTC CTC ATG GGG TCC GGC CAT           495
Val Met Ile Trp Ile Tyr Gly Gly Ala Phe Leu Met Gly Ser Gly His
100             105                 110                     115

GGG GCC AAC TTC CTC AAC AAC TAC CTG TAT GAC GGC GAG GAG ATC GCC           543
Gly Ala Asn Phe Leu Asn Asn Tyr Leu Tyr Asp Gly Glu Glu Ile Ala
                120                 125                     130

ACA CGC GGA AAC GTC ATC GTG GTC ACC TTC AAC TAC CGT GTC GGC CCC           591
Thr Arg Gly Asn Val Ile Val Val Thr Phe Asn Tyr Arg Val Gly Pro
            135                 140                 145

CTT GGG TTC CTC AGC ACT GGG GAC GCC AAT CTG CCA GGT AAC TAT GGC           639
Leu Gly Phe Leu Ser Thr Gly Asp Ala Asn Leu Pro Gly Asn Tyr Gly
        150                 155                 160

CTT CGG GAT CAG CAC ATG GCC ATT GCT TGG GTG AAG AGG AAT ATC GCG           687
Leu Arg Asp Gln His Met Ala Ile Ala Trp Val Lys Arg Asn Ile Ala
    165                 170                 175

GCC TTC GGG GGG GAC CCC AAC AAC ATC ACG CTC TTC GGG GAG TCT GCT           735
Ala Phe Gly Gly Asp Pro Asn Asn Ile Thr Leu Phe Gly Glu Ser Ala
180                 185                 190                 195

GGA GGT GCC AGC GTC TCT CTG CAG ACC CTC TCC CCC TAC AAC AAG GGC           783
Gly Gly Ala Ser Val Ser Leu Gln Thr Leu Ser Pro Tyr Asn Lys Gly
                200                 205                 210

CTC ATC CGG CGA GCC ATC AGC CAG AGC GGC GTG GCC CTG AGT CCC TGG           831
Leu Ile Arg Arg Ala Ile Ser Gln Ser Gly Val Ala Leu Ser Pro Trp
            215                 220                 225

GTC ATC CAG AAA AAC CCA CTC TTC TGG GCC AAA AAG GTG GCT GAG AAG           879
Val Ile Gln Lys Asn Pro Leu Phe Trp Ala Lys Lys Val Ala Glu Lys
        230                 235                 240

GTG GGT TGC CCT GTG GGT GAT GCC GCC AGG ATG GCC CAG TGT CTG AAG           927
Val Gly Cys Pro Val Gly Asp Ala Ala Arg Met Ala Gln Cys Leu Lys
    245                 250                 255

GTT ACT GAT CCC CGA GCC CTG ACG CTG GCC TAT AAG GTG CCG CTG GCA           975
Val Thr Asp Pro Arg Ala Leu Thr Leu Ala Tyr Lys Val Pro Leu Ala
260                 265                 270                 275
```

| | | | | | | | | | | | | | | | | |
|---|---|---|---|---|---|---|---|---|---|---|---|---|---|---|---|---|
| GGC | CTG | GAG | TAC | CCC | ATG | CTG | CAC | TAT | GTG | GGC | TTC | GTC | CCT | GTC | ATT | 1023 |
| Gly | Leu | Glu | Tyr 280 | Pro | Met | Leu | His | Tyr 285 | Val | Gly | Phe | Val | Pro 290 | Val | Ile | |
| GAT | GGA | GAC | TTC | ATC | CCC | GCT | GAC | CCG | ATC | AAC | CTG | TAC | GCC | AAC | GCC | 1071 |
| Asp | Gly | Asp | Phe 295 | Ile | Pro | Ala | Asp | Pro 300 | Ile | Asn | Leu | Tyr | Ala 305 | Asn | Ala | |
| GCC | GAC | ATC | GAC | TAT | ATA | GCA | GGC | ACC | AAC | AAC | ATG | GAC | GGC | CAC | ATC | 1119 |
| Ala | Asp | Ile 310 | Asp | Tyr | Ile | Ala | Gly 315 | Thr | Asn | Asn | Met | Asp 320 | Gly | His | Ile | |
| TTC | GCC | AGC | ATC | GAC | ATG | CCT | GCC | ATC | AAC | AAG | GGC | AAC | AAG | AAA | GTC | 1167 |
| Phe | Ala | Ser 325 | Ile | Asp | Met | Pro | Ala 330 | Ile | Asn | Lys | Gly | Asn 335 | Lys | Lys | Val | |
| ACG | GAG | GAG | GAC | TTC | TAC | AAG | CTG | GTC | AGT | GAG | TTC | ACA | ATC | ACC | AAG | 1215 |
| Thr 340 | Glu | Glu | Asp | Phe | Tyr 345 | Lys | Leu | Val | Ser | Glu 350 | Phe | Thr | Ile | Thr | Lys 355 | |
| GGG | CTC | AGA | GGC | GCC | AAG | ACG | ACC | TTT | GAT | GTC | TAC | ACC | GAG | TCC | TGG | 1263 |
| Gly | Leu | Arg | Gly | Ala 360 | Lys | Thr | Thr | Phe | Asp 365 | Val | Tyr | Thr | Glu | Ser 370 | Trp | |
| GCC | CAG | GAC | CCA | TCC | CAG | GAG | AAT | AAG | AAG | AAG | ACT | GTG | GTG | GAC | TTT | 1311 |
| Ala | Gln | Asp | Pro 375 | Ser | Gln | Glu | Asn | Lys 380 | Lys | Lys | Thr | Val | Val 385 | Asp | Phe | |
| GAG | ACC | GAT | GTC | CTC | TTC | CTG | GTG | CCC | ACC | GAG | ATT | GCC | CTA | GCC | CAG | 1359 |
| Glu | Thr | Asp 390 | Val | Leu | Phe | Leu | Val 395 | Pro | Thr | Glu | Ile | Ala 400 | Leu | Ala | Gln | |
| CAC | AGA | GCC | AAT | GCC | AAG | AGT | GCC | AAG | ACC | TAC | GCC | TAC | CTG | TTT | TCC | 1407 |
| His | Arg 405 | Ala | Asn | Ala | Lys | Ser 410 | Ala | Lys | Thr | Tyr | Ala 415 | Tyr | Leu | Phe | Ser | |
| CAT | CCC | TCT | CGG | ATG | CCC | GTC | TAC | CCC | AAA | TGG | GTG | GGG | GCC | GAC | CAT | 1455 |
| His 420 | Pro | Ser | Arg | Met | Pro 425 | Val | Tyr | Pro | Lys | Trp 430 | Val | Gly | Ala | Asp | His 435 | |
| GCA | GAT | GAC | ATT | CAG | TAC | GTT | TTC | GGG | AAG | CCC | TTC | GCC | ACC | CCC | ACG | 1503 |
| Ala | Asp | Asp | Ile | Gln 440 | Tyr | Val | Phe | Gly | Lys 445 | Pro | Phe | Ala | Thr | Pro 450 | Thr | |
| GGC | TAC | CGG | CCC | CAA | GAC | AGG | ACA | GTC | TCT | AAG | GCC | ATG | ATC | GCC | TAC | 1551 |
| Gly | Tyr | Arg | Pro 455 | Gln | Asp | Arg | Thr | Val 460 | Ser | Lys | Ala | Met | Ile 465 | Ala | Tyr | |
| TGG | ACC | AAC | TTT | GCC | AAA | ACA | GGG | GAC | CCC | AAC | ATG | GGC | GAC | TCG | GCT | 1599 |
| Trp | Thr | Asn 470 | Phe | Ala | Lys | Thr | Gly 475 | Asp | Pro | Asn | Met | Gly 480 | Asp | Ser | Ala | |
| GTG | CCC | ACA | CAC | TGG | GAA | CCC | TAC | ACT | ACG | GAA | AAC | AGC | GGC | TAC | CTG | 1647 |
| Val | Pro 485 | Thr | His | Trp | Glu | Pro 490 | Tyr | Thr | Thr | Glu | Asn 495 | Ser | Gly | Tyr | Leu | |
| GAG | ATC | ACC | AAG | AAG | ATG | GGC | AGC | AGC | TCC | ATG | AAG | CGG | AGC | CTG | AGA | 1695 |
| Glu | Ile | Thr | Lys | Lys 505 | Met | Gly | Ser | Ser | Ser 510 | Met | Lys | Arg | Ser | Leu | Arg 515 | |
| Glu 500 | | | | | | | | | | | | | | | | |
| ACC | AAC | TTC | CTG | CGC | TAC | TGG | ACC | CTC | ACC | TAT | CTG | GCG | CTG | CCC | ACA | 1743 |
| Thr | Asn | Phe | Leu | Arg 520 | Tyr | Trp | Thr | Leu | Thr 525 | Tyr | Leu | Ala | Leu | Pro 530 | Thr | |
| GTG | ACC | GAC | CAG | GAG | GCC | ACC | CCT | GTG | CCC | CCC | ACA | GGG | GAC | TCC | GAG | 1791 |
| Val | Thr | Asp | Gln | Glu 535 | Ala | Thr | Pro | Val | Pro 540 | Pro | Thr | Gly | Asp | Ser 545 | Glu | |
| GCC | ACT | CCC | GTG | CCC | CCC | ACG | GGT | GAC | TCC | GAG | ACC | GCC | CCC | GTG | CCG | 1839 |
| Ala | Thr | Pro 550 | Val | Pro | Pro | Thr | Gly 555 | Asp | Ser | Glu | Thr | Ala 560 | Pro | Val | Pro | |
| CCC | ACG | GGT | GAC | TCC | GGG | GCC | CCC | CCC | GTG | CCG | CCC | ACG | GGT | GAC | TCC | 1887 |
| Pro | Thr | Gly 565 | Asp | Ser | Gly | Ala | Pro 570 | Pro | Val | Pro | Pro | Thr 575 | Gly | Asp | Ser | |
| GGG | GCC | CCC | CCC | GTG | CCG | CCC | ACG | GGT | GAC | TCC | GGG | GCC | CCC | CCC | GTG | 1935 |
| Gly | Ala 580 | Pro | Pro | Val | Pro 585 | Pro | Thr | Gly | Asp | Ser 590 | Gly | Ala | Pro | Pro 595 | Val | |

| | | | | | | | | | | | | | | | |
|---|---|---|---|---|---|---|---|---|---|---|---|---|---|---|---|
| CCG | CCC | ACG | GGT | GAC | TCC | GGG | GCC | CCC | CCC | GTG | CCG | CCC | ACG | GGT | GAC |
| Pro | Pro | Thr | Gly | Asp | Ser | Gly | Ala | Pro | Pro | Val | Pro | Pro | Thr | Gly | Asp |
| | | | 600 | | | | | 605 | | | | | | 610 | |

1983

| | | | | | | | | | | | | | | | |
|---|---|---|---|---|---|---|---|---|---|---|---|---|---|---|---|
| TCC | GGG | GCC | CCC | CCC | GTG | CCG | CCC | ACG | GGT | GAC | TCC | GGG | GCC | CCC | CCT |
| Ser | Gly | Ala | Pro | Pro | Val | Pro | Pro | Thr | Gly | Asp | Ser | Gly | Ala | Pro | Pro |
| | | | 615 | | | | | 620 | | | | | | 625 | |

2031

| | | | | | | | | | | | | | | | |
|---|---|---|---|---|---|---|---|---|---|---|---|---|---|---|---|
| GTG | CCC | CCC | ACA | GAT | GAC | TCC | AAG | GAA | GCT | CAG | ATG | CCT | GCA | GTC | ATT |
| Val | Pro | Pro | Thr | Asp | Asp | Ser | Lys | Glu | Ala | Gln | Met | Pro | Ala | Val | Ile |
| | | 630 | | | | | 635 | | | | | 640 | | | |

2079

AGG TTT TAGCGTCCCA TGAGCCTTGG TATCAAGAGG CCACAAGAGT GGGACCCCAG  2135
Arg Phe
    645

GGGCTCCCCT CCCATCTTGA GCTCTTCCTG AATAAAGCCT CATACCCCT  2184

( 2 ) INFORMATION FOR SEQ ID NO:9:

( i ) SEQUENCE CHARACTERISTICS:
        ( A ) LENGTH: 668 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Leu | Thr | Met | Gly | Arg | Leu | Gln | Leu | Val | Val | Leu | Gly | Leu | Thr | Cys |
| -23 | | | -20 | | | | -15 | | | | -10 | | | | |
| Cys | Trp | Ala | Val | Ala | Ser | Ala | Ala | Lys | Leu | Gly | Ala | Val | Tyr | Thr | Glu |
| | | -5 | | | | | 1 | | | | 5 | | | | |
| Gly | Gly | Phe | Val | Glu | Gly | Val | Asn | Lys | Lys | Leu | Gly | Leu | Leu | Gly | Asp |
| 10 | | | | 15 | | | | 20 | | | | | 25 | | |
| Ser | Val | Asp | Ile | Phe | Lys | Gly | Ile | Pro | Phe | Ala | Ala | Pro | Thr | Lys | Ala |
| | | | 30 | | | | 35 | | | | 40 | | | | |
| Leu | Glu | Asn | Pro | Gln | Pro | His | Pro | Gly | Trp | Gln | Gly | Thr | Leu | Lys | Ala |
| | | | 45 | | | | 50 | | | | 55 | | | | |
| Lys | Asn | Phe | Lys | Lys | Arg | Cys | Leu | Gln | Ala | Thr | Ile | Thr | Gln | Asp | Ser |
| | | 60 | | | | 65 | | | | 70 | | | | | |
| Thr | Tyr | Gly | Asp | Glu | Asp | Cys | Leu | Tyr | Leu | Asn | Ile | Trp | Val | Pro | Gln |
| | 75 | | | | 80 | | | | 85 | | | | | | |
| Gly | Arg | Lys | Gln | Val | Ser | Arg | Asp | Leu | Pro | Val | Met | Ile | Trp | Ile | Tyr |
| 90 | | | | 95 | | | | 100 | | | | | | 105 | |
| Gly | Gly | Ala | Phe | Leu | Met | Gly | Ser | Gly | His | Gly | Ala | Asn | Phe | Leu | Asn |
| | | | 110 | | | | 115 | | | | 120 | | | | |
| Asn | Tyr | Leu | Tyr | Asp | Gly | Glu | Glu | Ile | Ala | Thr | Arg | Gly | Asn | Val | Ile |
| | | | 125 | | | | 130 | | | | 135 | | | | |
| Val | Val | Thr | Phe | Asn | Tyr | Arg | Val | Gly | Pro | Leu | Gly | Phe | Leu | Ser | Thr |
| | | 140 | | | | 145 | | | | 150 | | | | | |
| Gly | Asp | Ala | Asn | Leu | Pro | Gly | Asn | Tyr | Gly | Leu | Arg | Asp | Gln | His | Met |
| | 155 | | | | 160 | | | | 165 | | | | | | |
| Ala | Ile | Ala | Trp | Val | Lys | Arg | Asn | Ile | Ala | Ala | Phe | Gly | Gly | Asp | Pro |
| 170 | | | | 175 | | | | 180 | | | | | | 185 | |
| Asn | Asn | Ile | Thr | Leu | Phe | Gly | Glu | Ser | Ala | Gly | Gly | Ala | Ser | Val | Ser |
| | | | 190 | | | | 195 | | | | 200 | | | | |
| Leu | Gln | Thr | Leu | Ser | Pro | Tyr | Asn | Lys | Gly | Leu | Ile | Arg | Arg | Ala | Ile |
| | | | 205 | | | | 210 | | | | 215 | | | | |
| Ser | Gln | Ser | Gly | Val | Ala | Leu | Ser | Pro | Trp | Val | Ile | Gln | Lys | Asn | Pro |
| | | 220 | | | | 225 | | | | 230 | | | | | |
| Leu | Phe | Trp | Ala | Lys | Lys | Val | Ala | Glu | Lys | Val | Gly | Cys | Pro | Val | Gly |

|     |     |     |     | 235 |     |     |     |     | 240 |     |     |     |     | 245 |     |
| --- | --- | --- | --- | --- | --- | --- | --- | --- | --- | --- | --- | --- | --- | --- | --- |
| Asp 250 | Ala | Ala | Arg | Met | Ala 255 | Gln | Cys | Leu | Lys | Val 260 | Thr | Asp | Pro | Arg | Ala 265 |
| Leu | Thr | Leu | Ala | Tyr 270 | Lys | Val | Pro | Leu | Ala 275 | Gly | Leu | Glu | Tyr | Pro 280 | Met |
| Leu | His | Tyr | Val 285 | Gly | Phe | Val | Pro | Val 290 | Ile | Asp | Gly | Asp | Phe 295 | Ile | Pro |
| Ala | Asp | Pro 300 | Ile | Asn | Leu | Tyr | Ala 305 | Asn | Ala | Ala | Asp | Ile 310 | Asp | Tyr | Ile |
| Ala | Gly 315 | Thr | Asn | Asn | Met | Asp 320 | Gly | His | Ile | Phe | Ala 325 | Ser | Ile | Asp | Met |
| Pro 330 | Ala | Ile | Asn | Lys | Gly 335 | Asn | Lys | Lys | Val | Thr 340 | Glu | Glu | Asp | Phe | Tyr 345 |
| Lys | Leu | Val | Ser | Glu 350 | Phe | Thr | Ile | Thr | Lys 355 | Gly | Leu | Arg | Gly | Ala 360 | Lys |
| Thr | Thr | Phe | Asp 365 | Val | Tyr | Thr | Glu | Ser 370 | Trp | Ala | Gln | Asp | Pro 375 | Ser | Gln |
| Glu | Asn | Lys 380 | Lys | Lys | Thr | Val | Val 385 | Asp | Phe | Glu | Thr | Asp 390 | Val | Leu | Phe |
| Leu | Val 395 | Pro | Thr | Glu | Ile | Ala 400 | Leu | Ala | Gln | His | Arg 405 | Ala | Asn | Ala | Lys |
| Ser 410 | Ala | Lys | Thr | Tyr | Ala 415 | Tyr | Leu | Phe | Ser | His 420 | Pro | Ser | Arg | Met | Pro 425 |
| Val | Tyr | Pro | Lys | Trp 430 | Val | Gly | Ala | Asp | His 435 | Ala | Asp | Asp | Ile | Gln 440 | Tyr |
| Val | Phe | Gly | Lys 445 | Pro | Phe | Ala | Thr | Pro 450 | Thr | Gly | Tyr | Arg | Pro 455 | Gln | Asp |
| Arg | Thr | Val 460 | Ser | Lys | Ala | Met | Ile 465 | Ala | Tyr | Trp | Thr | Asn 470 | Phe | Ala | Lys |
| Thr | Gly 475 | Asp | Pro | Asn | Met | Gly 480 | Asp | Ser | Ala | Val | Pro 485 | Thr | His | Trp | Glu |
| Pro 490 | Tyr | Thr | Thr | Glu | Asn 495 | Ser | Gly | Tyr | Leu | Glu 500 | Ile | Thr | Lys | Lys | Met 505 |
| Gly | Ser | Ser | Ser | Met 510 | Lys | Arg | Ser | Leu | Arg 515 | Thr | Asn | Phe | Leu | Arg 520 | Tyr |
| Trp | Thr | Leu | Thr 525 | Tyr | Leu | Ala | Leu | Pro 530 | Thr | Val | Thr | Asp | Gln 535 | Glu | Ala |
| Thr | Pro | Val 540 | Pro | Pro | Thr | Gly | Asp 545 | Ser | Glu | Ala | Thr | Pro 550 | Val | Pro | Pro |
| Thr | Gly 555 | Asp | Ser | Glu | Thr | Ala 560 | Pro | Val | Pro | Pro | Thr 565 | Gly | Asp | Ser | Gly |
| Ala 570 | Pro | Pro | Val | Pro | Pro 575 | Thr | Gly | Asp | Ser | Gly 580 | Ala | Pro | Pro | Val | Pro 585 |
| Pro | Thr | Gly | Asp | Ser 590 | Gly | Ala | Pro | Pro | Val 595 | Pro | Pro | Thr | Gly | Asp 600 | Ser |
| Gly | Ala | Pro | Pro 605 | Val | Pro | Pro | Thr | Gly 610 | Asp | Ser | Gly | Ala | Pro 615 | Pro | Val |
| Pro | Pro | Thr 620 | Gly | Asp | Ser | Gly | Ala 625 | Pro | Pro | Val | Pro | Pro 630 | Thr | Asp | Asp |
| Ser | Lys 635 | Glu | Ala | Gln | Met | Pro 640 | Ala | Val | Ile | Arg | Phe 645 |     |     |     |     |

( 2 ) INFORMATION FOR SEQ ID NO:10:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

CGGGATCCGA AGCCCTTCGC CACCCCCACG        30

( 2 ) INFORMATION FOR SEQ ID NO:11:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CGAAGCTTGT CGACTTACTA CTGATCAGTC ACTGTGGGCA GCGCCAG        47

( 2 ) INFORMATION FOR SEQ ID NO:12:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

GGGAATTCTG GCCATTGCTT GGGTGAAGAG GAATATCGCG GCCTTCGGGG GGGACCCAA        60

CCAGATCACG CTCTTCGGGG AGTCT        85

( 2 ) INFORMATION FOR SEQ ID NO:13:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

CGGGATCCCA CATAGTGCAG CATGGGGTAC TCCAGGCC        38

( 2 ) INFORMATION FOR SEQ ID NO:14:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

GATCAGGGGG CCCCCCCCGT GCCGCCCACG GGTGACTCCG GG        42

( 2 ) INFORMATION FOR SEQ ID NO:15:

( i ) SEQUENCE CHARACTERISTICS:
    ( A ) LENGTH: 43 base pairs
    ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

GCCCCCCCG TGCCGCCCAC GGGTGACTCC AAGGAAGCTC AGA 43

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TGCCTGCAGT CATTAGGTTT TAGTAAGTCG ACA 33

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AGCTTGTCGA CTTACTAAAA CCTAATGACT G 31

( 2 ) INFORMATION FOR SEQ ID NO:18:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CAGGCATCTG AGCTTCCTTG GAGTCACCCG TGGGCGGCAC GGGGGGGGCC CCGGA 55

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GTCACCCGTG GGCGGCACGG GGGGGCCCC CT 32

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:20:

GATCAGAAGG AAGCTCAGA 19

(2) INFORMATION FOR SEQ ID NO:21:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:21:

CAGGCATCTG AGCTTCCTTC T 21